United States Patent
Sklar et al.

(10) Patent No.: US 10,376,313 B2
(45) Date of Patent: *Aug. 13, 2019

(54) SYSTEM AND METHOD FOR ADVANCING, ORIENTING, AND IMMOBILIZING ON INTERNAL BODY TISSUE A CATHETER OR OTHER THERAPEUTIC DEVICE

(71) Applicant: Ablacor Medical Corporation, Needham, MA (US)

(72) Inventors: Martin J. Sklar, Needham, MA (US); Howard Ring, Newton, MA (US)

(73) Assignee: Ablacor Medical Corporation, Needham, MA (US)

( * ) Notice: Subject to any disclaimer, the term of this patent is extended or adjusted under 35 U.S.C. 154(b) by 172 days.

This patent is subject to a terminal disclaimer.

(21) Appl. No.: 15/419,233

(22) Filed: Jan. 30, 2017

(65) Prior Publication Data

US 2017/0135763 A1    May 18, 2017

Related U.S. Application Data

(63) Continuation of application No. 13/934,351, filed on Jul. 3, 2013, now Pat. No. 9,554,851, which is a
(Continued)

(51) Int. Cl.
*A61B 18/18* (2006.01)
*A61M 25/01* (2006.01)
(Continued)

(52) U.S. Cl.
CPC .............. *A61B 18/18* (2013.01); *A61B 5/053* (2013.01); *A61B 5/4836* (2013.01);
(Continued)

(58) Field of Classification Search
CPC . A61B 18/1492; A61B 18/18; A61B 18/1815; A61B 2017/003;
(Continued)

(56) References Cited

U.S. PATENT DOCUMENTS 5,125,928 A    6/1992 Parins et al.
5,562,722 A    10/1996 Racz et al.
(Continued)

FOREIGN PATENT DOCUMENTS

WO    2005/046461 A1    5/2005

OTHER PUBLICATIONS

International Preliminary Report on Patentability dated Nov. 15, 2012 for International Application No. PCT/US2011/035348 (7 Pages).
(Continued)

*Primary Examiner* — Michael F Peffley
*Assistant Examiner* — Amanda L Zink
(74) *Attorney, Agent, or Firm* — Brown Rudnick LLP; Adam M. Schoen

(57) ABSTRACT

This invention provides a system and method that allows a therapeutic device, such as an atrial fibrillation microwave ablation catheter or ablation tip to be guided to a remote location within a body cavity and then accurately immobilized on the tissue, including that of a moving organ, such as the heart. In various embodiments, the system and method also enables accurate movement and steering along the tissue, while in engagement therewith. Such movement and engagement entails the use of vacuum or microneedle structures on at least two interconnected and articulated immobilizers that selectively engage to and release from the tissue to allow a crawling or traversing walking across the organ as the therapeutic catheter/tool tip applies treatment (AGE devices). In further embodiments that lack a movement capability (AID devices), the immobilizers allow a predetermined position for the introduced device to be maintained against the tissue while a treatment is applied to the location adjacent thereto. In the exemplary AID devices, variety of steering mechanisms and mechanisms for exposing and
(Continued)

anchoring a catheter against the underlying tissue can be employed. In the exemplary AGE devices, a variety of articulation and steering mechanisms, including those based upon pneumatic/hydraulic bellows, lead screws and electromagnetic actuators can be employed.

10 Claims, 46 Drawing Sheets

Related U.S. Application Data continuation of application No. 11/694,002, filed on Mar. 30, 2007, now Pat. No. 8,535,304.

(60) Provisional application No. 60/744,016, filed on Mar. 31, 2006.

(51) Int. Cl.
*A61B 5/053* (2006.01)
*A61B 5/00* (2006.01)
*A61B 18/14* (2006.01)
*A61B 34/00* (2016.01)
*A61B 17/00* (2006.01)
*A61B 18/00* (2006.01)
*A61M 25/02* (2006.01)

(52) U.S. Cl.
CPC ...... *A61B 18/1492* (2013.01); *A61B 18/1815* (2013.01); *A61B 34/71* (2016.02); *A61B 34/72* (2016.02); *A61M 25/0113* (2013.01); *A61B 2017/003* (2013.01); *A61B 2018/00291* (2013.01); *A61B 2018/1861* (2013.01); *A61M 25/0147* (2013.01); *A61M 25/0155* (2013.01); *A61M 25/0158* (2013.01); *A61M 2025/0213* (2013.01)

(58) Field of Classification Search
CPC .. A61B 2018/00291; A61B 2018/1861; A61B 34/71; A61B 34/72; A61B 5/053; A61B 5/4836; A61M 2025/0213; A61M 25/0113; A61M 25/0147; A61M 25/0155; A61M 25/0158
See application file for complete search history.

(56) References Cited

U.S. PATENT DOCUMENTS

| | | | |
|---|---|---|---|
| 5,876,399 A | 3/1999 | Chia et al. | |
| 5,906,591 A | 5/1999 | Dario et al. | |
| 5,971,983 A | 10/1999 | Lesh | |
| 6,063,081 A | 5/2000 | Mulier et al. | |
| 6,200,311 B1 | 3/2001 | Danek et al. | |
| 6,254,599 B1 | 7/2001 | Lesh et al. | |
| 6,305,378 B1 | 10/2001 | Lesh | |
| 6,416,511 B1 | 7/2002 | Lesh et al. | |
| 6,463,332 B1 | 10/2002 | Aldrich | |
| 6,471,697 B1 | 10/2002 | Lesh | |
| 6,517,477 B1 | 2/2003 | Wendlandt | |
| 6,527,769 B2 | 3/2003 | Langberg et al. | |
| 6,529,756 B1 | 3/2003 | Phan et al. | |
| 6,595,989 B1* | 7/2003 | Schaer | A61B 17/22004 606/41 |
| 6,645,199 B1* | 11/2003 | Jenkins | A61B 18/1492 606/41 |
| 6,652,517 B1 | 11/2003 | Hall et al. | |
| 6,752,805 B2 | 6/2004 | Maguire et al. | |
| 6,764,486 B2 | 7/2004 | Natale | |
| 6,770,070 B1 | 8/2004 | Balbierz | |
| 6,771,533 B2 | 8/2004 | Witcraft et al. | |
| 6,773,433 B2* | 8/2004 | Stewart | A61B 18/1492 606/41 |
| 6,855,144 B2 | 2/2005 | Lesh | |
| 6,872,205 B2 | 3/2005 | Lesh et al. | |
| 6,893,438 B2 | 5/2005 | Hall et al. | |
| 6,893,442 B2 | 5/2005 | Whayne | |
| 6,955,173 B2 | 10/2005 | Lesh | |
| 6,964,660 B2 | 11/2005 | Maguire et al. | |
| 6,979,331 B2 | 12/2005 | Hintringer et al. | |
| 7,008,418 B2 | 3/2006 | Hall et al. | |
| 7,063,698 B2 | 6/2006 | Whayne et al. | |
| 7,066,880 B2 | 6/2006 | Wendlandt | |
| 7,083,614 B2* | 8/2006 | Fjield | A61B 17/2202 128/898 |
| 7,156,816 B2 | 1/2007 | Schwartz et al. | |
| 7,578,819 B2* | 8/2009 | Bleich | A61B 17/1626 600/554 |
| 7,655,005 B2 | 2/2010 | Bhola | |
| 7,753,906 B2 | 7/2010 | Esposito | |
| 2002/0107478 A1 | 8/2002 | Wendlandt | |
| 2002/0111617 A1* | 8/2002 | Cosman | A61B 18/1485 606/41 |
| 2002/0156499 A1 | 10/2002 | Konya et al. | |
| 2002/0173774 A1 | 11/2002 | Olsen | |
| 2003/0060821 A1* | 3/2003 | Hall | A61B 18/1492 606/41 |
| 2003/0065250 A1 | 4/2003 | Chiel | |
| 2003/0069578 A1 | 4/2003 | Hall et al. | |
| 2003/0069587 A1 | 4/2003 | Schorgl et al. | |
| 2003/0088305 A1* | 5/2003 | Van Schie | A61F 2/06 623/1.12 |
| 2003/0093072 A1* | 5/2003 | Friedman | A61B 18/1492 606/41 |
| 2003/0120270 A1 | 6/2003 | Acker | |
| 2003/0167056 A1* | 9/2003 | Jahns | A61B 18/1492 606/41 |
| 2004/0034347 A1 | 2/2004 | Hall et al. | |
| 2004/0193021 A1 | 9/2004 | Zdeblick et al. | |
| 2004/0236320 A1 | 11/2004 | Protsenko et al. | |
| 2004/0267337 A1 | 12/2004 | Hayzelden | |
| 2005/0154376 A1* | 7/2005 | Riviere | A61B 1/00156 606/1 |
| 2005/0182392 A1 | 8/2005 | Brucker et al. | |
| 2005/0222557 A1 | 10/2005 | Baxter et al. | |
| 2005/0235996 A1* | 10/2005 | Hooser | A61M 16/0463 128/207.14 |
| 2005/0240116 A1* | 10/2005 | Saadat | A61B 5/015 600/549 |
| 2005/0273095 A1 | 12/2005 | Taimisto et al. | |
| 2006/0025756 A1 | 2/2006 | Francischelli et al. | |
| 2006/0084960 A1 | 4/2006 | Mester et al. | |
| 2006/0106298 A1 | 5/2006 | Ahmed et al. | |
| 2006/0200124 A1 | 9/2006 | Whayne et al. | |
| 2006/0206113 A1 | 9/2006 | Whayne et al. | |
| 2006/0235381 A1 | 10/2006 | Whayne et al. | |
| 2006/0247607 A1 | 11/2006 | Cornelius et al. | |
| 2007/0249999 A1 | 10/2007 | Sklar et al. | |
| 2007/0265609 A1 | 11/2007 | Thapliyal et al. | |
| 2007/0265610 A1 | 11/2007 | Thapliyal et al. | |
| 2008/0249518 A1 | 10/2008 | Warnking et al. | |
| 2008/0281322 A1 | 11/2008 | Sherman et al. | |
| 2009/0221996 A1 | 9/2009 | Lesh | |
| 2009/0312755 A1 | 12/2009 | Thapliyal et al. | |
| 2010/0042110 A1 | 2/2010 | Kelley et al. | |
| 2010/0049099 A1 | 2/2010 | Thapliyal et al. | |
| 2010/0198041 A1 | 8/2010 | Christian et al. | |

OTHER PUBLICATIONS

Patronik, et al., "A Miniature Cable-Driven Robot for Crawling on the Heart," Engineering in Medicine and Biology, May 2, 2005, pp. 5771-5774, Publisher: National Science Foundation, Published in Shanghai, China (4 Pages).

Patronik, et al., "Crawling on the Heart: A Mobile Robotic Device for Minimally Invasive Cardiac Interventions," Sep. 1, 2004, Publisher: Springer-Verlag 2004, Published in Pittsburgh, PA (8 Pages).

Patronik, et al., "Development of a Tethered Epicardial Crawler for Minimally Invasive Cardiac Therapies," Apr. 1, 2004, pp. 239-240, Publisher: IEEE, Published in Pittsburg, PA (2 Pages).

(56) References Cited

OTHER PUBLICATIONS

Razjouyan, et al., "Enhancing the Locomotion of an In Vivo Robot for Cardiac Surgery," Apr. 1, 2006, pp. 97-98, Published in Pittsburg, PA (2 Pages).
Riviere, et al., "Prototype Epicardial Crawling Device for Intrapericardial Intervention on the Beating Heart," The Heart Surgery Forum, Sep. 16, 2004, pp. E639-E643, vol. 7, No. 6, Publisher: Forum Multimedia Publishing, LLC, Published in Pittsburgh, PA (5 Pages).
Supplementary European Search Report for Application No. 11778338. 1, dated Oct. 22, 2013, (5 Pages).

* cited by examiner

SYSTEM AND METHOD FOR ADVANCING, ORIENTING, AND IMMOBILIZING ON INTERNAL BODY TISSUE A CATHETER OR OTHER THERAPEUTIC DEVICE

RELATED APPLICATIONS

This application is a continuation of U.S. Nonprovisional application Ser. No. 13/934,351, filed Jul. 3, 2013 (now issued as U.S. Pat. No. 9,554,851), which is a continuation of U.S. Nonprovisional application Ser. No. 11/694,002, filed Mar. 30, 2007 (now issued as U.S. Pat. No. 8,535,304), which claims the benefit of U.S. Provisional Application Ser. No. 60/744,016, filed Mar. 31, 2006, entitled INSTRUMENT TRANSPORTATION AND POSITIONING CATHETER, and U.S. Provisional Application Ser. No. 60/868,951, filed Dec. 7, 2006, entitled ABLATION GUIDANCE SYSTEM FOR MINIMALLY INVASIVE ATRIAL FIBRILLATION SURGERY, the entire disclosure of each application being herein incorporated by reference.

FIELD OF THE INVENTION

This invention relates to systems and methods for performing minimally invasive surgery and more particularly to systems and methods for manipulating therapeutic or diagnostic devices relative to organs and other tissues within a human body cavity.

BACKGROUND OF THE INVENTION

Minimally invasive surgery is becoming the preferred technique for accessing internal organs and systems in an ever increasing number of procedures. Its advantages are manifold. For example, recovery times are greatly decreased due to smaller incisions and less damage to internal structures while gaining access to the procedure site. Also, the risk of post-operative infection is somewhat reduced as the internal tissues are less exposed to non-sterile environments. In addition, the procedure is often simplified and expedited due to the lack of complex incisions and post-procedure suturing of large incisions.

Typically, in minimally invasive procedures, instruments are inserted into the body through steerable catheters that are initially inserted and brought adjacent to the affected organ or other procedure site. However, standard catheters do not stabilize the instrument in place while it is being used by the surgeon. Similarly, standard catheters can only be coarsely steered and are not generally capable of following a serpentine path.

Some specialized mechanisms for stabilizing particular instruments have been devised for procedures that require a close and immobile relationship between the instrument and the tissue being operated upon. For example, Bertolero et al., U.S. Pat. No. 6,849,075 teaches a cardiac ablation device that employs a plurality vacuum orifices to hold an ablation electrode in position on the heart. However, this reference does not provide a mechanism to move the electrode along a serpentine path on the heart or other organ, as may be required in certain procedures, most notably cardiac ablation, as described below. Likewise, there is no mechanism in Bertolero to bring, for example, a microwave ablation catheter into selective contact with heart tissue, as may be required for effective ablation.

An alternate approach suggested for transporting and positioning minimally invasive surgical instruments inside the body is taught by Riviere, et al. in Published U.S. patent application Ser. No. 10/982,670, using a walking robot. The robot comprises two pedestals connected by a spring. The distal pedestal includes a tool, typically a scope for viewing the affected area. The foot of each pedestal has vacuum orifices, with a separate vacuum line running to each pedestal. A pair of pull wires is connected to each pedestal, allowing control of the relative position between the distal pedestal and the proximal pedestal. By properly sequencing the application of vacuum and the tension on the pull wires, a surgeon can cause the robot to "inchworm" across the surface of an organ. Surgical instruments are attached to the front of the distal pedestal.

The Riviere robot employs a large vacuum region that interfaces best with flat organ tissue that is reasonably resilient. Under certain conditions its hold down could become dislodged or allow lateral slippage of the corresponding tool—particularly where the tissue surface is non-flat or roughened. To remedy such slippage, the vacuum applied to each pedestal may be increased. However, under other conditions tissue could be damaged by too intense local vacuum.

Moreover, these and other available devices lack the ability to perform more complex procedures, such as drug delivery, dissection and biopsy. Accordingly, it is highly desirable to provide improved mechanisms and devices for minimally invasive surgical procedures that afford improved function as well as superior mobility, immobilization once positioned, and control of an ablation device or other attached tool.

SUMMARY OF THE INVENTION

This invention overcomes the disadvantages of the prior art by providing a system and method that allows a therapeutic device, such as an atrial fibrillation microwave ablation catheter or ablation tip to be guided to a remote location within a body cavity and then accurately immobilized on the tissue, including that of a moving organ, such as the heart. In various embodiments, the system and method also enables accurate movement and steering along the tissue, while in engagement therewith. Such movement and engagement entails the use of vacuum suction, compression balloon, or microneedle structures on at least two interconnected and articulated immobilizers that selectively engage to and release from the tissue to allow an undulating, step-by-step crawling/walking motion (termed a "traversing" motion herein) across the organ as the therapeutic catheter/tool tip applies treatment (AGE devices). In further embodiments that lack a movement capability (AID devices), the immobilizers allow a predetermined position for the introduced device to be maintained against the tissue while a treatment is applied to the location adjacent thereto. In the exemplary AGE devices, variety of steering mechanisms and mechanisms for exposing and anchoring a catheter against the underlying tissue can be employed. In the exemplary AGE devices, a variety of articulation and steering mechanisms, including those based upon pneumatic/hydraulic bellows, lead screws and electromagnetic actuators can be employed.

In certain embodiments of an AGE or AID, the base includes one or more vacuum structures constructed with an accordion-like or bellows like shape so as to conform to curved surfaces.

In other embodiments of an AGE or AID steering can occur based on a plurality of wires disposed about the perimeter and anchored at an appropriate location on the structure of the device. The wires are selectively tensioned or relaxed to effect steering. A control system joystick or other actuation structure causes tensioning and slacking of the wires.

In other embodiments, generally related to the AGE steering and actuation for (traversing) movement between the proximal immobilizer and the distal immobilizer occurs based upon selective movement of individual bellows disposed between the immobilizers, about the perimeters thereof.

In other embodiments of an AGE, actuation between immobilizers is effected using a flexible or rigid helical drive that is rotated by a shaft operatively connected through the device's proximal cannula with a control system. Where the helical drive is rigid, a universal joint or other flexible, rotating joint can be provided at a location between the immobilizers (at the proximal immobilizer, distal immobilizer, or between the immobilizers). In the above helical drive implementations, steering wires extend from the proximal immobilizer to anchors in the distal immobilizer. In another helical or linear actuation drive define a rigid structure and steering is effected by a pivoting suction cup mounted in the base of the proximal immobilizer, with which the entire AGE pivots in response to steering wires anchored in the proximal immobilizer.

In various embodiments of an AID or AGE, a balloon or bladder is located within a lumen that carries the catheter. This balloon is connected with a pressure/vacuum source. When pressurized, the balloon inflates, thereby frictionally locking the catheter in place against axial pullout and biasing the catheter into a bottom most position with respect to the underlying tissue. In other embodiments, such a lock can be mechanical, such as a sliding contact surface that selectively moves into engagement with the catheter when slid or actuated.

A variety of bellows like structures can be disposed between steerable sections of an AGE or AID. These structures can be actuated by pressure or can be non-actuatable, flexible covers with the actuation mechanism (in the case of AGEs) being another mechanism. Other actuation or actuation/steering mechanisms, with or without an outer bellows covering, include repelling, individually energized arrays of electromagnets, arrays of smaller-diameter pressurized bellows, flexible or pivotal, overlapping piston and cylinder sleeves and push-pull rods actuated by a remote user.

In an alternate embodiment one or more immobilizers can include a plurality of tissue-engaging microneedles that are deployable from locations on the immobilizer base/bottom via pressurized guideways. The needles can be installed in a single elongated base or in a plurality of side-by-side smaller bases so that individual sets of needles can extend different distances to better conform to a curved tissue surface.

Another embodiment of a hold-down mechanism for an AGE or AID comprises one or more inflatable, top-mounted balloons or bladders that are adapted to engage an opposing organ or tissue surface to retain the AGE against the underlying tissue.

An AID can also include a sliding base that moves proximally relative to fixed AID side bases that allows the enclosed catheter to be directly exposed to the tissue. The sliding base can include a steering wire anchored therein. In this arrangement, the hold down mechanism (vacuum ports, microneedles, etc) are located along the side edges of the AID's fixed base section. The AID can also include an exposed mid section base with thin reinforcing ribs at predetermined locations along its length to allow the catheter to be substantially in direct exposure to the underlying tissue. In such an arrangement hold-down vacuum ports or another hold-down mechanism are disposed along the side edges. An AGE can also include a partially exposed mid section with hold-down mechanisms, such as vacuum chambers, on the sides of the exposed mid section. This exposed mid-section allows the catheter to be at least partially, directly exposed to the underlying tissue.

In another embodiment of an AID, the catheter is contained within a series of incrementally spaced horseshoe-shaped hold-down segments that are interconnected by a vacuum lumen that communicate through vacuum ports in the base of each segment.

In other embodiments, the distal (or proximal) end of an AGE can include a deployable therapeutic or surgical tool. In exemplary embodiments, a pneumatic, electromagnetic or mechanical actuator allows a blade or other tool contained within the immobilizer to extend into contact with tissue. In the case of a biopsy tool, tissue can be drawn into a vacuum chamber within the base of the immobilizer for it to be acted upon by a horizontally disposed biopsy blade. Fluid-delivery hypodermic needles can also be deployed either at and acute angle or substantially normal to the underlying tissue by driving the (flexible) needles distally down an appropriately shaped guide lumen into the tissue below.

Certain features of various embodiments described above can be combined variously with others described above to achieve further illustrative embodiments of the invention.

BRIEF DESCRIPTION OF THE DRAWINGS

The invention description below refers to the accompanying drawings, of which.

DETAILED DESCRIPTION

I. SEMAP Technique

Figure 1:
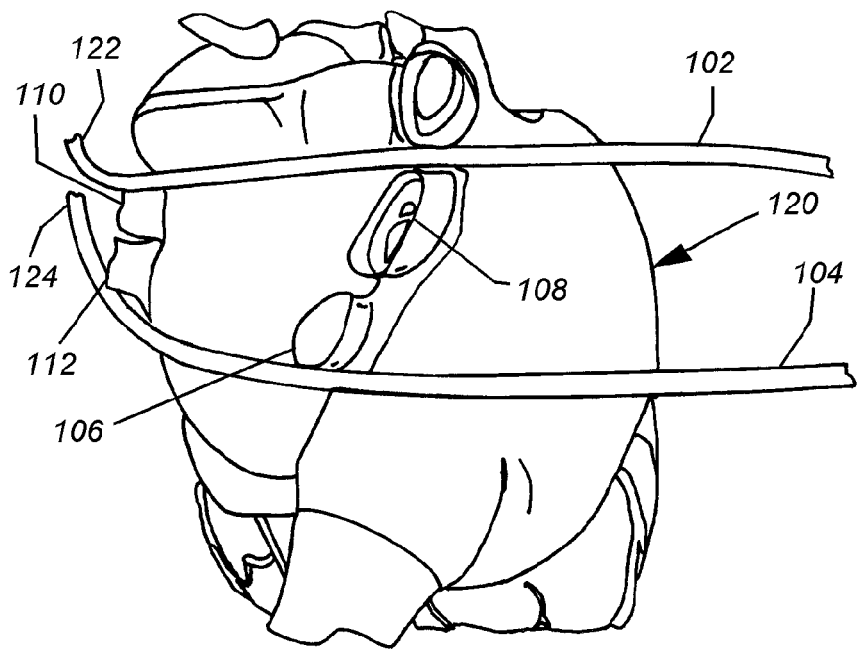
FIG. 1 is an illustration of the initial rubber catheter application step in an exemplary Saltman EndoMAze Procedure (SEMAP) for ablation of cardiac tissue in the treatment of atrial fibrillation according to the prior art.

The principles of this invention are generally applicable to the field of endocardial ablation. However, as will be described below, the systems and methods described herein can also be applied to procedures using other types of tools, and applied to procedures involving other internal organs and structures in addition to the heart. In general, atrial fibrillation (AF) is a common, but not fully understood disturbance of the heart's rhythm. It affects more than 2.2 million people in the Unites States. It has been determined that altering the electrophysiological state of the heart is useful in eliminating unwanted electrical activity. This activity is viewed to be the primary cause of AF. A well-known procedure for reducing electrical activity is the Cox Maze Procedure (CMP). This surgical procedure involves the invasive entry of the thoracic cavity to expose the heart. The heart is then dissected, and then re-sewn by sutures to disrupt unwanted pathways of electrical propagation. This procedure has been viewed as successful in a large number of cases.

An alternative to the physical dissection of the heart to attain the desired result is to generate scar tissue in a defined line around the affected regions of the heart by either burning or freezing the cardiac tissue that carries nerve connections deemed to be a cause of AF. The most common procedure, often termed "ablation", involves access to the inside of the heart, via for example the femoral vein. Typically, these procedures employ radiofrequency energy (RF) that is delivered internally to the left atrium in a catheter that is introduced to the heart via the femoral vein. The RF energy, which typically operates in the microwave band, heats or burns the tissue to a predetermined depth, thereby creating a single-point lesion that cuts the nerve pathway within that area of the myocardial wall. The lesions are overlapped one-upon-another until every point along the electrical pathway has been severed. The success rate in this type of surgery has been measured to be between approximately seventy percent and eight-five percent—rendering it a relatively successful outcome. There are, however, certain well-known side affects that may occur with respect to the endocardial ablation procedures as described above. In order to avoid some of these side affects, and simplify the procedure, Dr. Adam P. Saltman, M.D. PhD. has developed and employed the Saltman EndoMAze Procedure (also termed SEMAP). In practice, this procedure employs bilateral simultaneous thoroscopy and the Flex 10® microwave energy ablation catheter formerly available commercially from AFX, Inc. of Fremont, Calif., now Boston Scientific Corporation of Natick, Mass. Briefly, the procedure implicates the encircling of a portion of the heart's exterior (between the pericardium and epicardium) in the region of the four pulmonary veins by the ablation catheter. The encircled area is then heated as appropriate to form the necessary scaring so as to sever the electrical impulses (propagated by cellular conduction) that are believed to be the source of AF.

Figure 2:
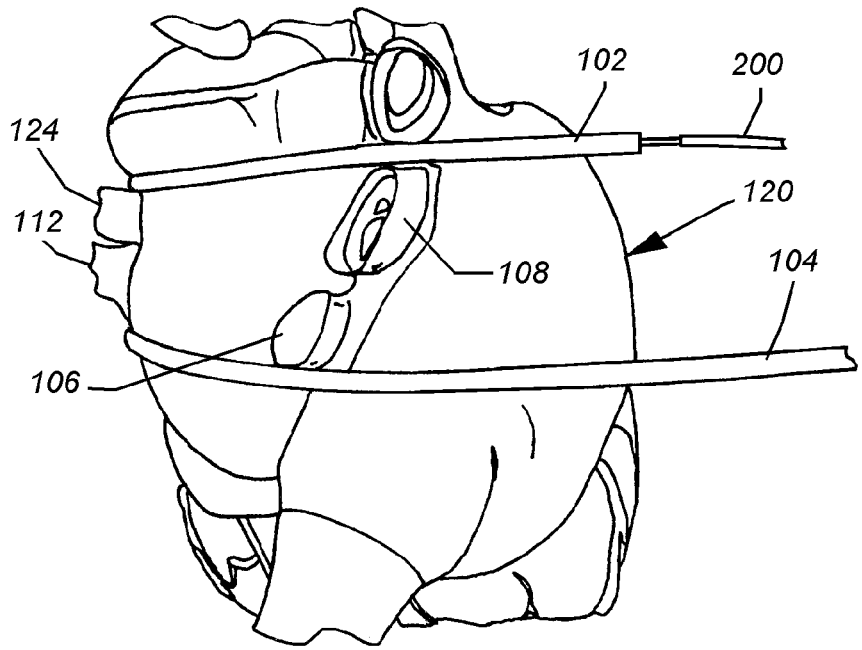
FIG. 2 is an illustration of an ablation catheter insertion step in connection with the SEMAP of FIG. 1, according to the prior art.

Referring to FIG. 1, the SEMAP procedure is initiated by introducing to the thoracic cavity, and then wrapping two rubber guide catheters 102 and 104 around the four pulmonary veins 106, 108, 110 and 112 of the subject heart 120. The catheters can be introduced to the region via minimally invasive techniques, which will be described further below. The two distal ends 122 and 124 of the guide catheters 102 and 104, respectively, are free until they are tied together to provide the terminal end of the chain around the heart. As shown in FIG. 2, a microwave catheter 200 (the Flex 10° in this example) is now introduced into the proximal end of one of the elastomeric/rubber guide catheters 102. In one example another (or the same) microwave catheter may also be introduced into the proximal end/opening of the opposing guide catheter 104. In alternate embodiments, a loop around the heart using a singe-guide catheter can be provided.

Each introduced microware ablation catheter 200 comprises a series of emitting segments that are joined by adjacent electrical connections. The emitting segments and electrical connections are collectively energized by a power source located external to the patient's body cavity. The application of energy is carefully controlled and monitored to produce the desired level and duration of ablation heat to the pericardium.

Figure 3:
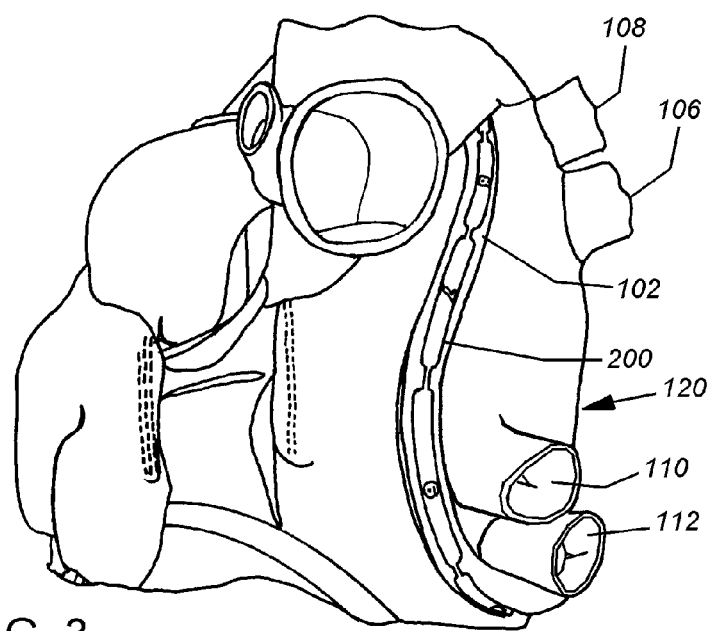
FIG. 3 is a top rear view of the subject heart undergoing a box lesion ablation step in connection with the SEMAP of FIG. 1, according to the prior art.
Figure 4:
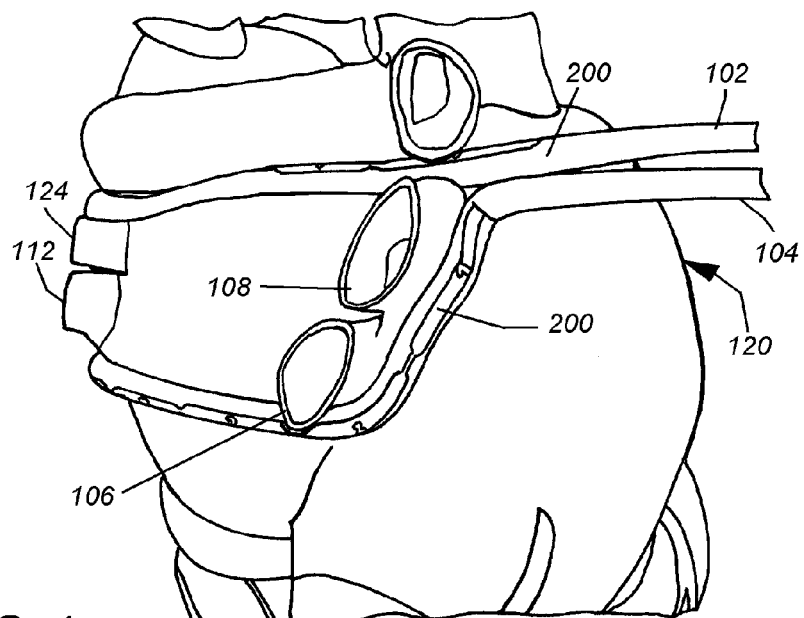
FIG. 4 is an oblique rear side view of the subject heart showing the box lesion ablation step of FIG. 3, according to the prior art.

As shown in FIG. 3, the segments lay against the heart in the region of the four pulmonary veins 106, 108, 110 and 112. As further viewed in FIG. 4, the ablation catheter(s) 200, which in this embodiment wraps fully around the pulmonary veins, starts at segment 1 as shown with respect to the guide catheter 104 and extends fully around the heart to exit at the opposing guide catheter 102.

The ablation catheters, once properly placed, are energized using known power application and duration to attain the desired result without excessive burning into the cardiac tissue.

The above-described SEMAP technique still requires substantial effort to affix the guide catheters at the appropriate locations with respect to the heart. In addition there is no particular mechanism to ensure a closely conforming relationship between the pericardial surface and the catheters and the inherent beating of the heart renders the placement and maintaining of the catheters at the appropriate location somewhat challenging.

II. Overview of Inventive Catheters and Introduction to Thoracic Cavity

Figure 5:
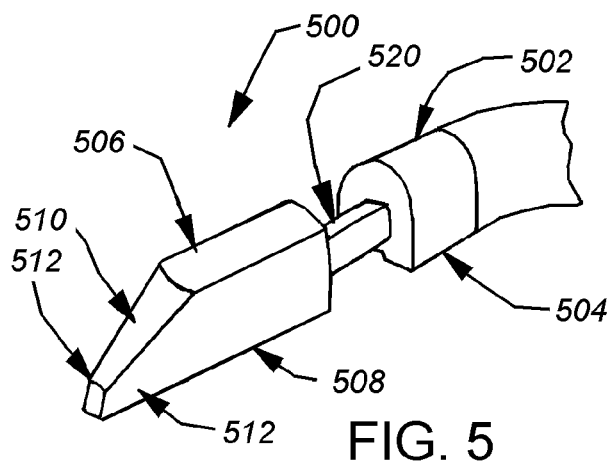
FIG. 5 is a perspective view of an ablation guidance enhancer (AGE) for use with an ablation or other therapeutic catheter or device in accordance with a generalized illustrative embodiment of this invention.

FIG. 5 details a basic overview of an ablation guidance enhancer (AGE) 500 in accordance with an overall embodiment of this invention. In this embodiment, the AGE 500 acts as a moving system that is capable of contacting coronary tissue (or other internal bodily tissue) along the pericardium, maintaining close, controlled contact with the tissue, while systematically traversing the pericardium to apply the needed ablation energy to sites that are desired in an incremental fashion. That is, in a typical procedure, the AGE moves to a desired location on the heart or other organ, becomes immobilized at that position and the device carried within the AGE, such as an ablation catheter, applies a therapeutic procedure to the underlying tissue.

Figure 6:
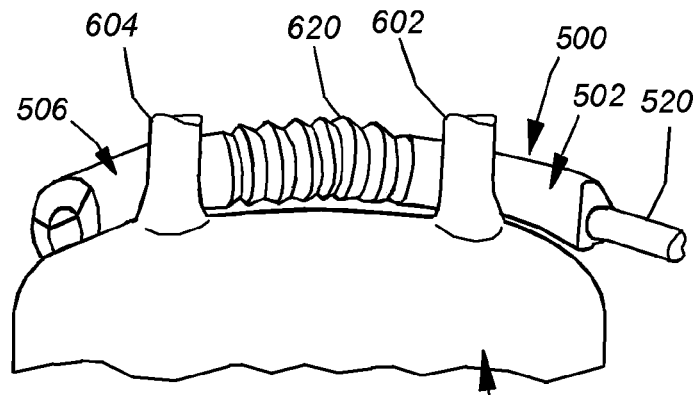
FIG. 6 is a perspective view of the AGE of FIG. 5 in engagement with a subject heart.
Figure 7:
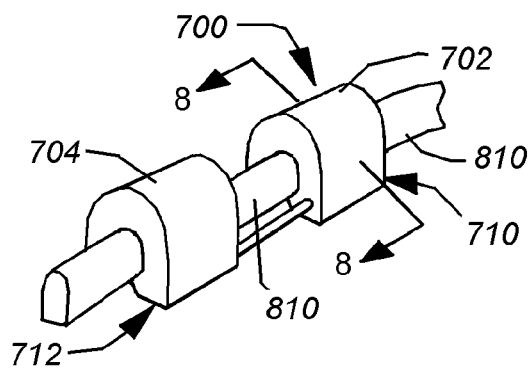
FIG. 7 is a perspective view of an ablation immobilizer device (AID) for use with an ablation or other therapeutic catheter or device in accordance with a generalized illustrative embodiment of this invention.

In this embodiment, the AGE comprises a proximal immobilizer 502 with vacuum hold-down capability or another type of hold-down capability (as described below) along its base 504. It also comprises a distal immobilizer 506 with similar vacuum or other remobilization capability along its base 508. Notably, the distal immobilizer 506 of this embodiment, and various other embodiments herein, includes a sloped top surface 510 and similarly inwardly sloped side surfaces 512. These sloped distal surfaces assist in allowing introduction and internal thoracic movement of the distal immobilizer 506 as will be described below. With reference briefly to FIG. 6, an illustration of the heart 600 is shown in which the AGE 500 moves along the heart's surface between respective pulmonary vessels 602 and 604 to apply needed ablation energy. The ablation energy, is in particular, provided by a microwave or similar catheter 520 that slides with respect to the proximal immobilizers 502 so as to allow the immobilizers to engaging in the above-described traversing motion across the tissue.

As shown in FIG. 6, a bellows 620 joins the distal and proximal immobilizers 502 and 506, thereby protecting the space therebetween from foreign matter. The material as the AGE is one that includes minimal moisture, so as to maximize the transmission of microwave energy without excessive heating. As will be described variously below, the bottom portion of each immobilizer can be enclosed or open, at least in part to allow microwave energy to pass therethrough. To this end, in certain embodiments the bottom portion may be open to the underlying tissue if the material between microwave catheter and target tissue characteristically absorbs and dissipates an unacceptable amount of microwave energy.

The AGE 500 is specifically designed to self-ambulatory, allowing it to be introduced into the body through a small, minimally invasive incision, as will be described below, and then move under its own power, under the manipulation of an operator, to traverse a desired area of contacting tissue. To, thus, summarize an example of the AGE's traversing movement: the distal immobilizer pulls the microwave catheter along, thereby expanding the bellows relative to the proximal immobilizer while the proximal immobilizer remains stationary (held-down) on the tissue. The distal immobilizer then becomes immobile or stationary and the proximal immobilizer is released from the tissue, and moved towards the distal immobilizer, or the bellows contracts, thereby slipping along the microwave catheter. The proximal immobilizer then reestablishes position in new location and sequence continues if desired.

Figure 8:
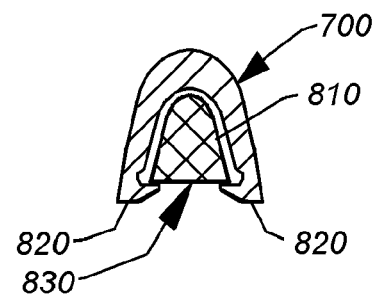
FIG. 8 is a cross section of the AID taken along line 8-8 of FIG. 7.

An alternate arrangement in accordance with this invention is the ablation immobilizer device (AID) as shown in FIG. 8. The AID 700 includes non-ambulatory segments 702 and 704. These segments may be steerable but do not perform the traversing function described above. The segments 702, 704 each contain at base 710 and 712, respectively, which communicates with an external vacuum source, similarly to the AGE, to apply holding suction to the underlying tissue. In use, the AID 700 is typically manipulated into position using appropriate guide wires, or other like-internal-placement techniques. As shown in cross section in FIG. 8, the exemplary AID encloses a microwave ablation catheter 810, similar or identical to the Flex 10 catheter 520 described above. The bottom edges 820 of the AID cross section may contain vacuum ports, as described above, to transmit the necessary hold-down vacuum to the underlying tissue. The central region 830 of the AID cross section is open in this embodiment to allow direct exposure of the microwave catheter's emission surface to the underlying tissue. With a sufficiently long AID, proper steering and placement can allow an entire area of the heart tissue to be ablated at once with the catheter axially fixed within the AID lumen. In other embodiments, the catheter can be moved axially within the lumen of the AID, similar to a train being guided along a track. Hence the AID is anchored on the tissue, and the catheter is moved distally out of the AID's distal end to increase the range of ablation (or another procedure) by treating tissue distally ahead of the AID. To cover a longer area, the AID can be moved and immobilized at another location on the tissue once it has treated a given area.

Note that certain embodiments of the AID contemplate an integral steering mechanism, typically employing a plurality of selectively tensioned wires about the perimeter. However, in a variety of illustrative embodiments, the AID is free of any steering function, acting as a passive, hold-down device. In a non-steerable form of the AID, other minimally invasive instruments are used to position the AID, including, but not limited to, trocars, guide catheters and steerable catheters with lumens through which the AID is passed. The AID basically functions to piggy-back the ablation catheter or other device as appropriate. The AID can also be employed to surround any catheter-like therapy device.

Figure 9:
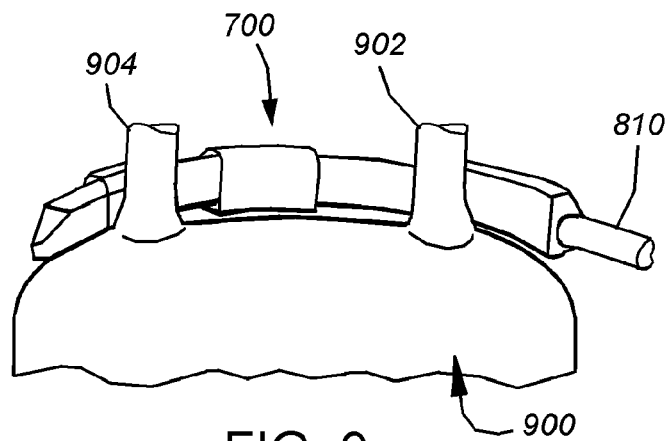
FIG. 9 is a perspective view of the AID of FIG. 8 in engagement with a subject heart.

As shown in FIG. 9, the AID 700 of this example is applied to a subject heart 900 between the pulmonary veins 902 and 904 to achieve a desired ablation in accordance with the principles of the above-described SEMAP technique. That is, the AID is selectively positioned so as to surround the four pulmonary veins and thereby generate scar tissue to block the electrical pathways in this ringed region.

Referring now to FIGS. 10 through 14, the introduction of an exemplary AGE to the thoracic cavity and subject heart is shown in further detail as part of a minimally invasive surgical treatment to treat AF. As noted above, this procedure is altered appropriately to introduce a non-ambulatory AID, in that an underlying guide catheter must be directed to the affected tissue site, and thereafter located so that the AID can take hold of the tissue on its own. Conversely, the AGE may engage internal organ tissue at any given location thereon, and then subsequently move to (and along) a desired location on the organ.

Figure 10:
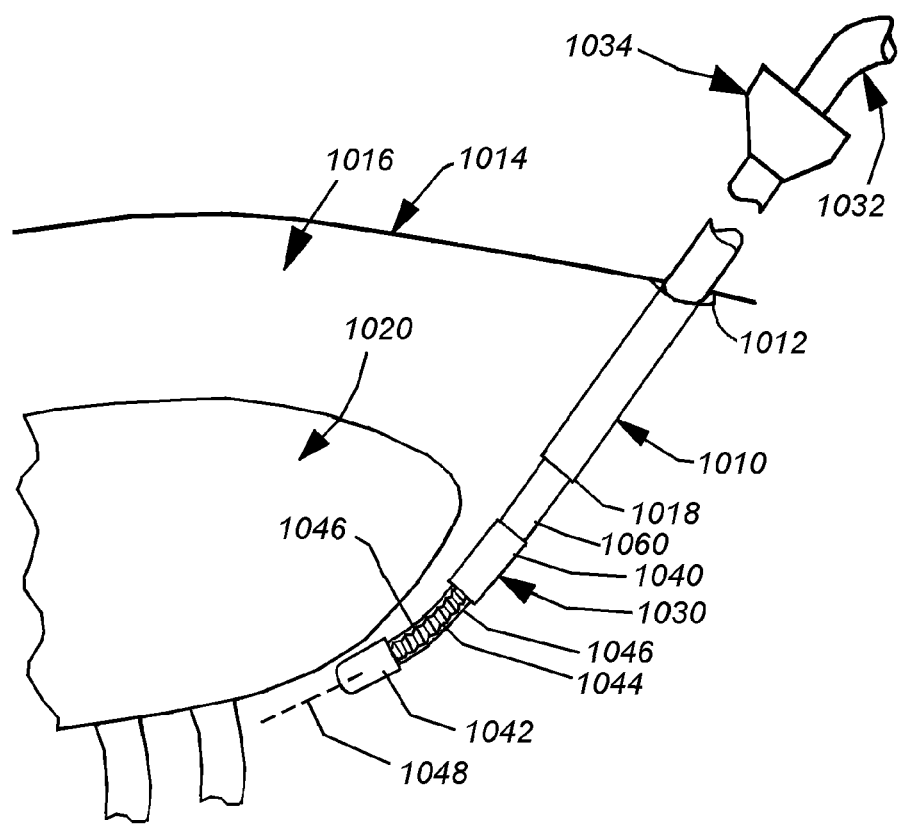
FIG. 10 is a an illustration of an insertion step for an exemplary AGE (or AID) through the skin and into a subject's thoracic cavity.
Figure 11:
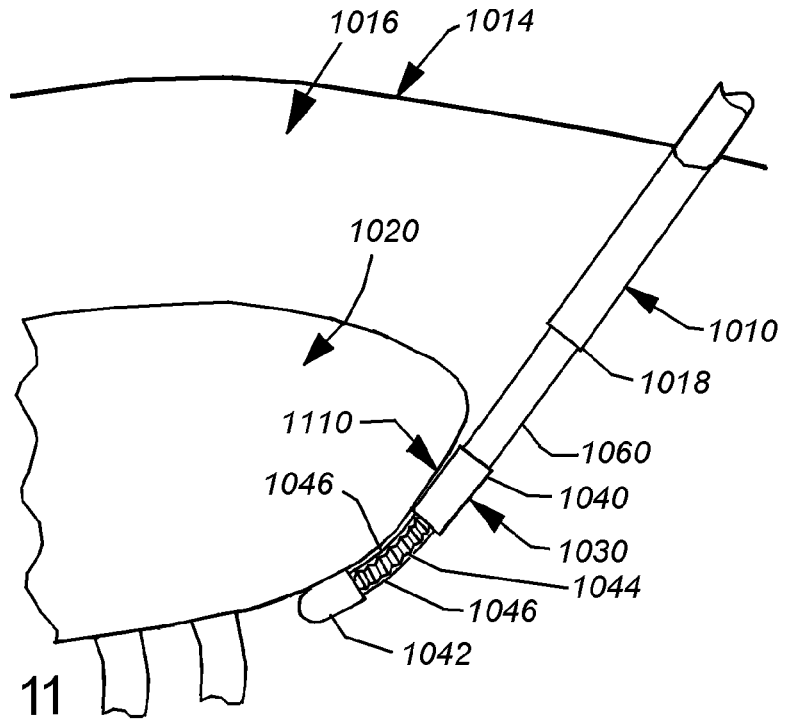
FIG. 11 is an illustration of the attachment of the AGE to the subject heart.

As now shown if FIG. 10, a trocar 1010 has been passed through an incision 1012 in the skin 1014 covering the patient's thoracic cavity 1016 so that the distal end 1018 of the trocar is adjacent to the heart 1020. The AGE 1030 is introduced through the trocar 1010, and now extends out of the distal end 1018. The AGE catheter's proximal end 1032, which typically includes a covering cannula, extends out of the flared proximal end 1034 of the trocar. The proximal cannula (1032) can extend from the proximal face of the proximal immobilizer back to a remote control system and appropriate power sources, as described further below.

Typically, the AGE or AID in this and other embodiments described herein defines an external shape capable of fitting within a generally cylindrical outline of approximately 10 to 14 millimeters in diameter so as to fit smoothly through a standard surgical cannula, which is typically approximately 15 millimeters in internal diameter.

The AGE 1030 of this embodiment includes a proximal immobilizer 1040, a distal immobilizer 1042, an interconnecting bellows 1044, and appropriate steering wires 1046 that surround the central axis 1048 of the AGE 1030. Briefly, in operation, a vacuum is applied to each immobilizer 1040 and 1042 to cause the immobilizers to selectively engage the underlying (heart) tissue. This engagement is shown generally in FIG. 11. As detailed therein, the distal and proximal immobilizers 1042 and 1040 have now engaged the tissue 1110. The microwave ablation catheter 1060 is contained within the distal and proximal immobilizers 1042, 1044, and extends proximally through the trocar 1010. The catheter 1060, which may also be enclosed within the proximal cannula 1032, is ready to be energized when the distal and proximal ends are positioned at the appropriate site on the heart 1020 for ablation. Thereafter, the AGE 1030 is directed by the practitioner to walk or perform the crawling/traversing motion across the heart surface, sequentially immobilizing itself by activating the vacuum in both immobilizers and then energizing the catheter for the prescribed time period so as to generate a scar tissue through selective heating. Progress of the catheter as it crawls along the surface can be tracked in a variety of ways. In general, the catheter and/or the AGE (or AID in other embodiments) can include radio opaque inserts and/or fillers that enable it to be easily tracked using scanning techniques such as fluoroscopy. Ultrasound and/or other internal imaging techniques can be employed. In alternate embodiments, a second endoscope can be inserted into the thoracic cavity to visually monitor the moving AGE's progress.

Figure 12:
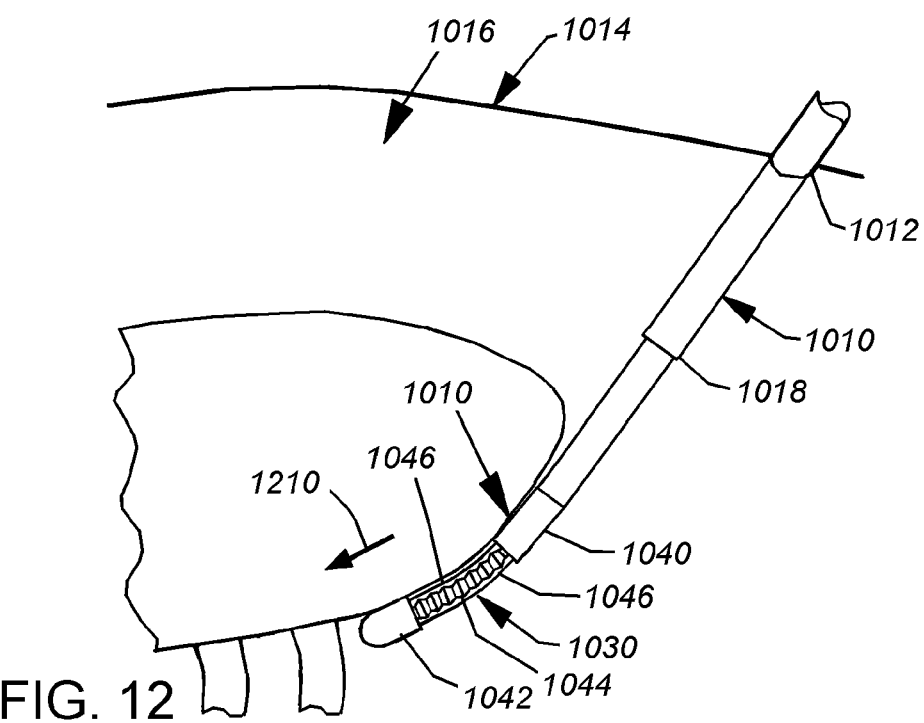
FIG. 12 is an illustration of the movement of the AGE along the heart in accordance with an illustrative embodiment.

As shown in FIG. 12, using the proximally located control system, the distal immobilizer 1042 of the AGE 1030 is caused to extend outwardly (arrow 1210) by action of the bellows 1044 or another actuation device, as described below. In operation, the distal immobilizer 1042 extends outwardly after the local vacuum to its base has been deactivated. Meanwhile, the vacuum on the proximal end 1040 is maintained. Subsequently, the proximal immobilizer 1040 is brought forward along the path of travel by releasing its vacuum and contracting the bellows 1040. At this time, the distal immobilizer's vacuum is maintained so that it maintains its hold against the tissue 1040. This traversing technique of crawling around the heart's surface allows each length of targeted tissue along the pathway to be incrementally radiated with microwaves and, thereby, ablated as appropriate.

Figure 13:
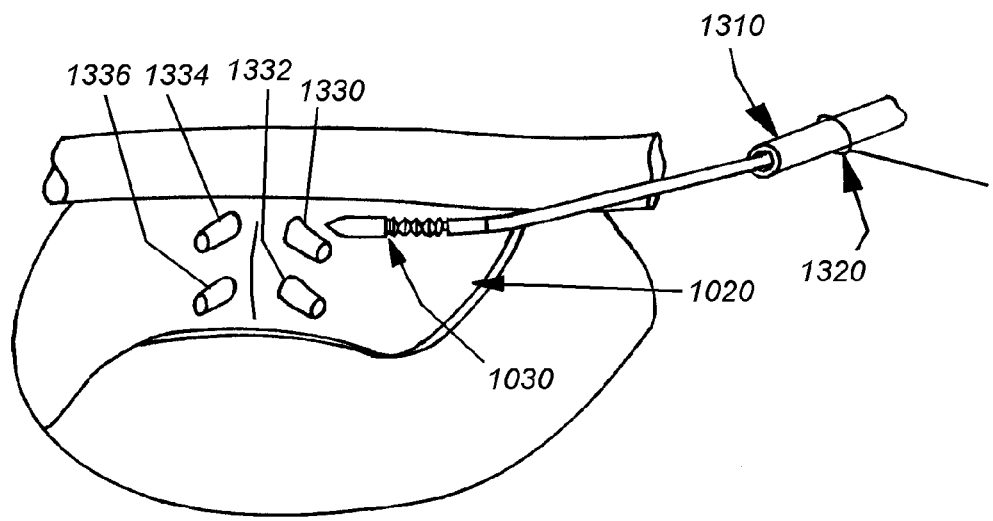
FIG. 13 is an illustration of the entry of the AGE to the back of the subject heart.
Figure 14:
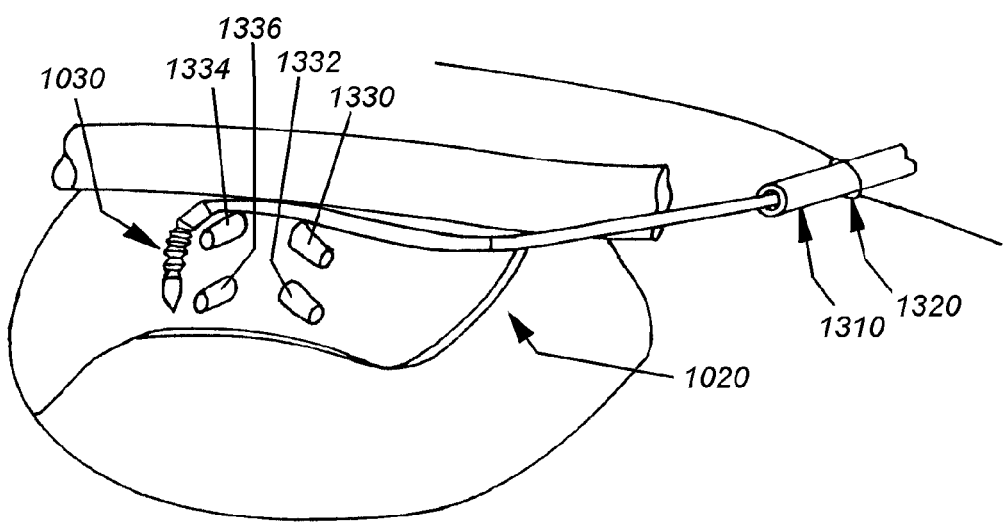
FIG. 14 is an illustration of the first turn of the AGE around the pulmonary veins of the subject heart.

To access more-remote portions of the heart, a trocar 1310 can be inserted through a backside incision 1320 as shown in FIG. 13. The AGE 1030 moves along the rear of the heart 1020 as shown to apply ablation energy to rear portions of the heart 1020, behind the pulmonary veins 1330, 1332, 1334 and 1336. With reference now to FIG. 14, the walking action of the AGE 1030 allows it to move around the veins as shown. It should be clear that a variety of introduction techniques are expressly contemplated herein. These techniques will depend, in part, upon whether an AGE or AID is being employed.

Figure 15:
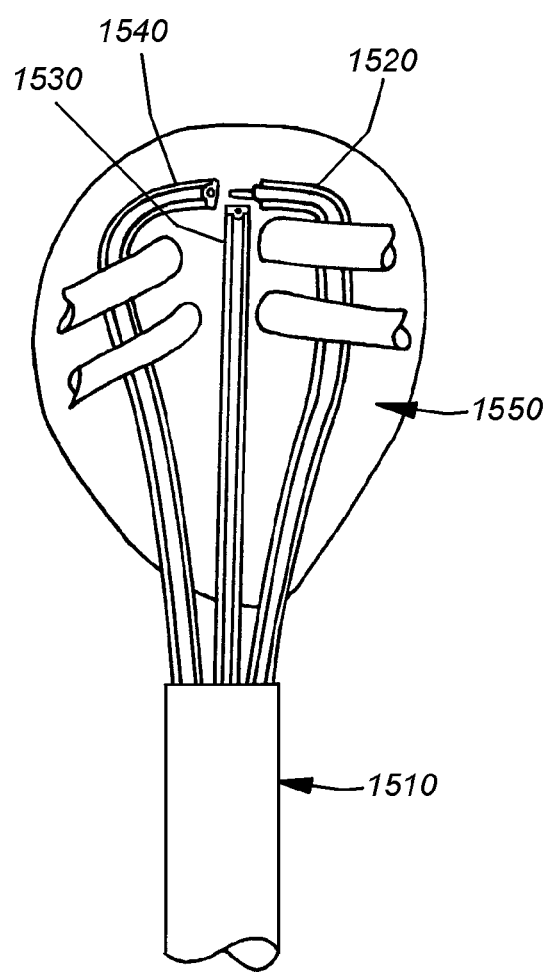
FIG. 15 is an illustration of the use of multiple AGEs (or AIDs) to engage the subject heart.

As shown in FIG. 15, it is contemplated that a larger-diameter trocar 1510 can be used to introduce multiple AGE or AID units 1520, 1530 and 1540 somewhat simultaneously to the treatment area of the heart 1550. Each of these devices can be energized in turn, or simultaneously, to achieve the desired ablation of the underlying tissue.

III. Immobilization/Hold-Down Mechanisms

Figure 16:
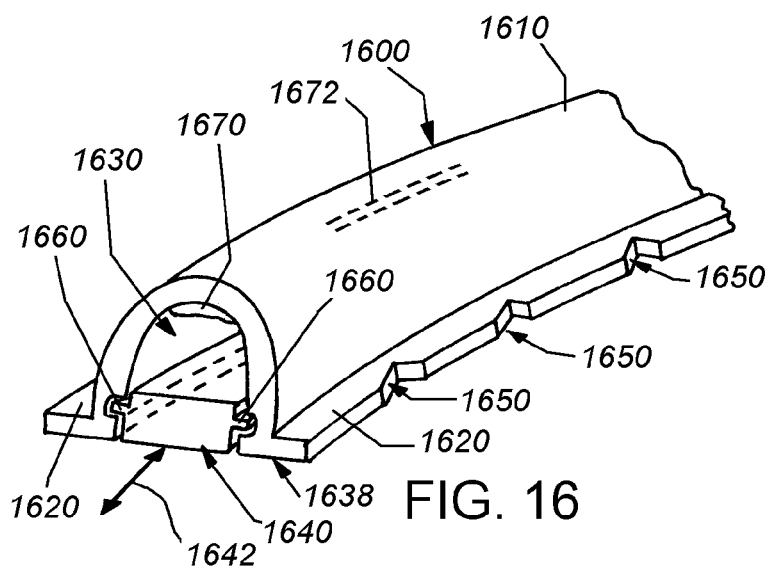
FIG. 16 is a perspective view of a movable floor for exposing a portion of a catheter enclosed within the central lumen of an AGE or AID according to an embodiment of this invention.
Figure 17:
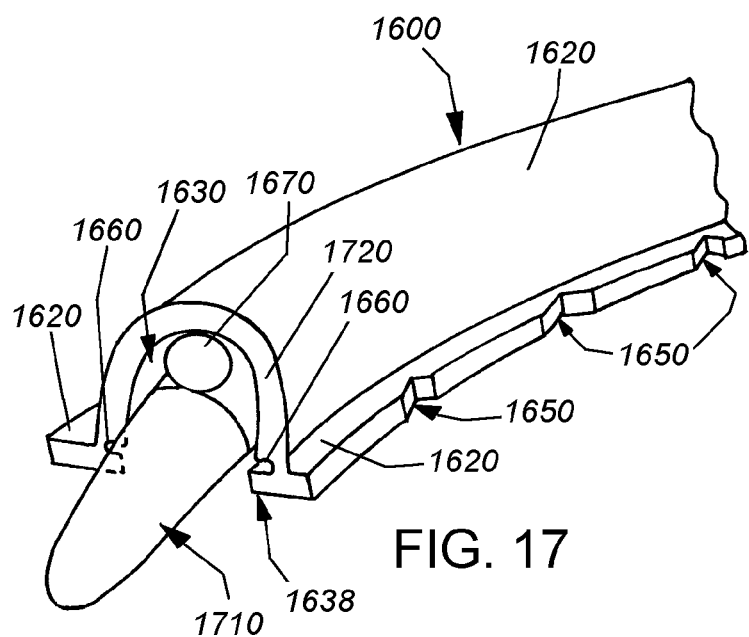
FIG. 17 is a perspective view of an inflatable bladder for displacing, toward underlying tissue, a portion of a catheter enclosed and/or maintaining said catheter's position axially within the central lumen of an AGE or AGE according to an embodiment of this invention.

One form of AID that can be implemented in accordance with the embodiment of FIG. 15 (or other embodiments herein) is shown in FIGS. 16 and 17. The depicted AID 1600 of this embodiment includes an open, inverted-U-shaped top section 1610 having a pair of outwardly extended basis 1620 that provide a somewhat "Omega" outline to the device's cross-section. The interior lumen 1630, is sized and arranged to accommodate a microwave ablation catheter, or another similarly sized/shaped catheter. To facilitate insertion the catheter's bottom side 1638 remains enclosed. The center of the catheter's bottom 1638 comprises a slidable bottom member 1640 that moves axially (double arrow 1642) as desired. It is controlled from outside the patient's body by grasping, and withdrawing proximally, a proximal end of the sliding base 1640 (or an interconnected element).

The catheter 1710 is shown inserted through the lumen 1630 in FIG. 17. The catheter 1710 extends beyond the distal end 1720 of the AID 1600 in this example, but can reside flush with or internal to the AID in alternate arrangements. The base 1640 has been removed to allow the catheter to be exposed relative to the underlying tissue. As described below, a variety of mechanisms can be used to share and steer the device. To facilitate shaping and steering, a series of V-shaped cutouts 1650 are provided along the base 1620. These cutouts 1650 provide stress-reliefs that enhance the bendability/steerability. In general, the cross section shape of this AID 1600 defines an "omega" shape with an inverted-U-shaped top 1610 and opposing, outwardly extending bases 1620. The omega cross section is inherently stiffer in the plane parallel to the bases 1620 on the tissue interface surface. Based upon this geometry, the depicted V-shaped 1650 cutouts provide a desired selective reduction in stiffness at their vertices of, inducing the catheter to bend in the region of the cutouts 1650.

Note that the sliding central base 1640 rides within a corresponding key slot 1660 formed into each side of the device's interior wall. These key slots 1660 ensure that the base 1640 does not become inadvertently dislodged. As will also be described below, the base 1620, or another portion of the device 1600 includes a plurality of vacuum ports that are selectively operated to cause the device to become firmly adhered to, and immobilized upon, the underlying tissue when the vacuum is applied.

While discussed further below with respect to additional features according to embodiments of this invention, this embodiment of the AID 1600 includes an inflatable bladder or balloon 1670 near its distal end at the top of the interior lumen 1630. This feature is also applicable to other AID/AGE embodiments herein. The bladder 1670 communicates with a pressure source that can be routed through a lumen 1672 (shown in phantom) in the top wall of the device proximally to the control system that is external of the patient's body. When uninflated, the balloon allows passage of the catheter 1710 therethrough. When subsequently inflated, as shown in FIG. 17, the catheter is forced downwardly through the now opened bottom slot, and into closer proximity to the underlying tissue. This arrangement can improve the efficiency of ablation in this embodiment. The length of extension of the bladder 1670 along the longitudinal/axial direction of the AID 1600 is highly variable and depends, in part upon how long a section of catheter 1710 is to be displaced toward the underlying tissue.

Figure 18:
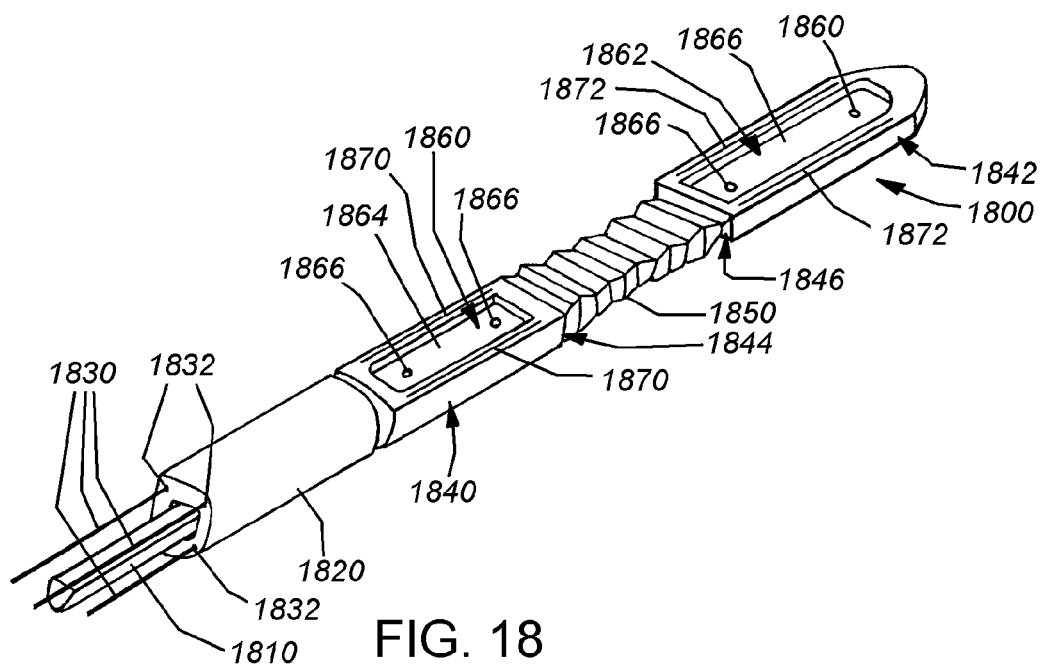
FIG. 18 is a bottom perspective view of an AGE according to an embodiment of this invention.
Figure 19:
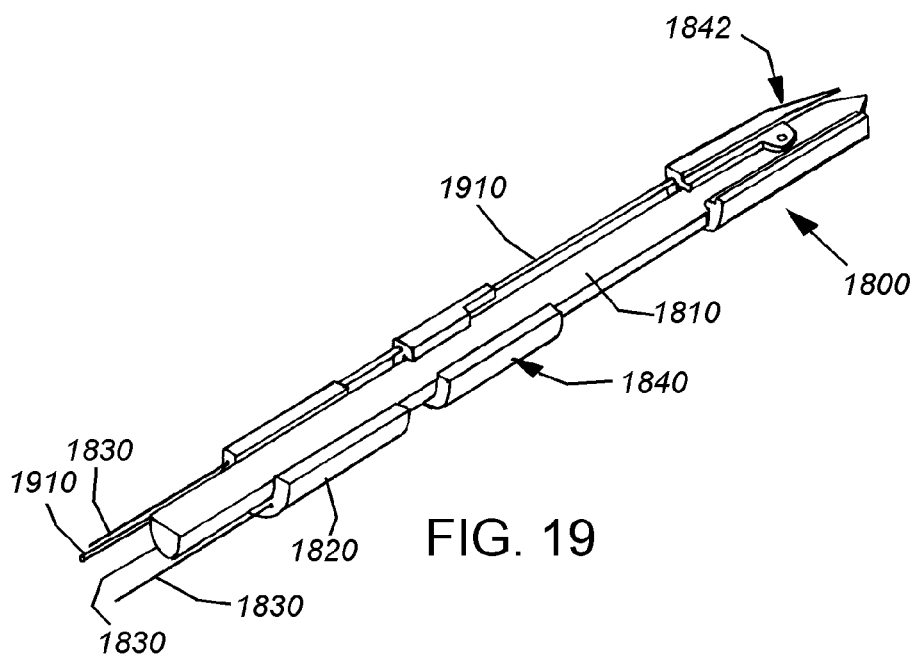
FIG. 19 is an exposed cutaway perspective view of the AGE of FIG. 18.

Reference is now made to FIGS. 18 and 19, which show an exemplary AGE 1800, respectively, in full external bottom view, and also in partial bottom cutaway. The microwave ablation catheter 1810 can be seen clearly passing through the AGE structure. A proximal cannula 1820 is provided ahead of the actual AGE 1800 to encase and guide the catheter 1810 and any surrounding wires, cables, lumens, etc., which are used to control and monitor the AGE. The cannula 1820 can extend fully to the actuation and/or guidance control system, which will be described further below, or the cannula can be truncated as appropriate. In most embodiments, the cannula 1820 extends the full distance proximally to the guidance system.

A set of at least three, circumferentially spaced steering wires 1830 extend through appropriately positioned lumens 1832 in the cannula 1820, and thereafter into each of the proximal immobilizer 1840 and distal immobilizer 1842. Typically the steering wires pass slidably through the proximal immobilizer 1840 and are distally anchored in the distal immobilizer 1842. A flexible bellows 1850 joins the proximal immobilizer 1840 and distal immobilizer 1842. This bellows can be sealed to the distal face 1844 and the proximal face 1846 of the distal immobilizer so as to allow an applied vacuum to cause the bellows to contract and thereby move immobilizers toward each other, or an applied pressure will move the immobilizers away from each other. This is one more possible mechanism for actuating movement in the AGE, although a plurality of alternate actuation mechanisms are described below. In alternate embodiments, the bellows 1850 is not the actuation mechanism and acts as an outer cover to protect underlying steering and actuation components. In certain non-bellows-actuating embodiments, this outer bellows can be omitted entirely.

The base 1860 and 1862 of each immobilizer 1840 and 1842, respectively, includes the central cavity or chamber 1864 and 1866, respectively. Each vacuum cavity 1864, 1866 comprises a vacuum chamber that is designed to bear against the underlying tissue. In this embodiment, a respective pair of vacuum ports 1866 is provided to each immobilizer's vacuum cavity 1864, 1866. Each pair of vacuum ports 1866 is connected to a respective vacuum source lumen that extends proximally to the control system, one of which lumens 1910 is shown, extending through the AGE 1800 to the distal immobilizer 1842. Each vacuum source lumen extends respectively to each of the immobilizers, thereby allowing each immobilizer's applied vacuum to be individually controlled. This in-part allows the crawling/traversing-type movement described above, as each immobilizer can be individually anchored to the tissue, while the other moves along the tissue.

As discussed above, within the bellows 1850 a variety of "actuation" mechanisms can be provided that allow the proximal immobilizer 1840 to move toward and away from the distal immobilizer 1842, thereby providing the desired movement across the surface. Likewise, the steering wires 1830 each selectively transmit tension between the proximal and distal immobilizers allowing distal immobilizer to deflect relative to the proximal immobilizer. As it is deflected at an angle, the distal immobilizer can be pushed forward by the actuation function, and thereafter secured to a new location. In this embodiment, each base includes a pair of linearly oriented electrodes 1870 and 1872 that can measure electrical conductivity, and thereby allow the user to confirm when a given base is in firm contact with an underlying tissue surface (among other readings). Transmission of electrical impulses between the electrodes 1870 indicates that both electrodes are contacting the tissue. In particular, these electrodes 1870 can be used to verify that a therapeutic ablation has been applied by determining if the applied ablation adequately disrupted an electrical test signal transmitted by the control system between the two electrodes along the contacted underlying tissue therebetween. In this embodiment, because the material of the AGE is relatively transparent to microwave energy (a silicone formulation, for example), the microwave energy passes through the AGE and heats the underlying tissue, which is saturated with moisture, and thereby increases in temperature in response to the applied microwave energy. As noted above, various vacuum conduits, electrical wires, and other needed components pass through appropriate lumens along the AGE 1800, and proximally back through the cannula 1820.

Figure 20A:
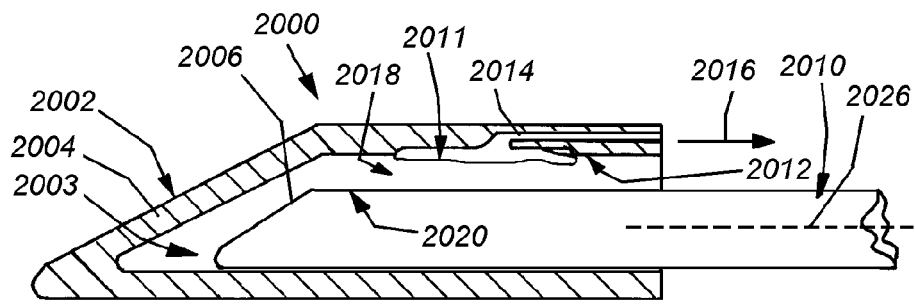
FIG. 20A is a side cross section of a distal immobilizer of an AGE including an inflatable luminal catheter-holding mechanism in an undeployed/uninflated orientation according to an embodiment of the invention.
Figure 20B:
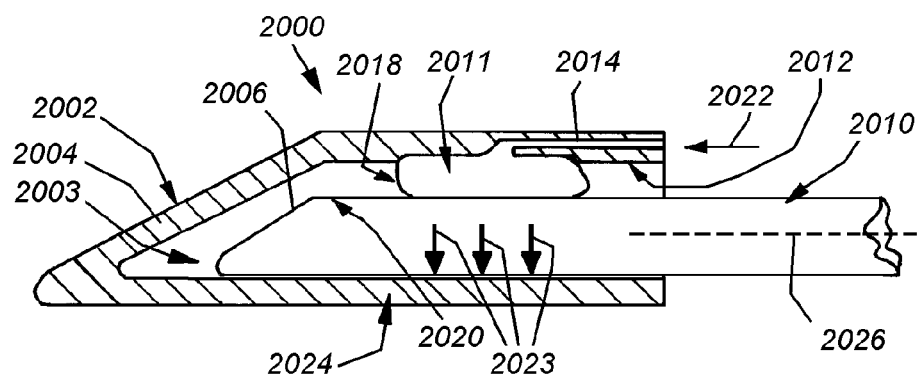
FIG. 20B is a side cross section of the distal immobilizer of FIG. 20A showing the catheter-holding mechanism in a deployed/inflated orientation.

Various embodiments of the AGE shown herein include a central lumen that is particularly sized and arranged to receive a therapeutic catheter. The lumen can be sized to closely conform to the shape of the catheter, or it can be somewhat oversized, allowing the catheter appropriate play within the device. The catheter shaft can be allowed to slide freely within the AGE or it can be anchored at some location along the AGE and/or proximal cannula. FIGS. 20A and 20B detail a mechanism for locking the catheter axially in place with respect to the AGE. This mechanism is structured and functions similarly to that of FIGS. 16-17 above. The mechanism is shown within an exemplary distal immobilizer 2000, which can include a variety of actuation, steering and immobilization systems in accordance with various teachings of this invention. This mechanism can also be applied to the proximal immobilizer or along the device cannula where appropriate.

As shown in FIG. 20A, the distal tip 2002 of the immobilizer is angled for improved insertion as discussed above. The tip 2002 in this embodiment, and various other embodiments, encloses the distal end of the immobilizer lumen 2003, and includes a front wall 2004 that is internally shaped to approximately conform to the distal end 2006 of a catheter 2010, which is also angled. A catheter with a non-angled tip can be used in alternate implementations.

As shown further in FIG. 20A, a deflated balloon or bladder 2011 is located on the inner top wall 2012 of the immobilizer lumen 2003. This balloon 2011, like others described variously herein can be constructed from any acceptable, pliable and expandable/elastic, thin-walled material. The balloon communicates with a lumen 2014 that interconnects with a pressure and vacuum source at the control system. As shown, a vacuum (proximal arrow 2016) has been applied through the lumen 2016 to evacuate and deflate the balloon 2011. This deflation creates an open gap 2018 between the top 2020 of the catheter 2010 and the balloon. This allows the catheter 2010 to move freely within the lumen 2003.

As shown in FIG. 20B, a pressure (distal arrow 2022) is now applied to the lumen 2014 and balloon 2011. This pressure causes the balloon 2011 to inflate as shown. The inflation causes the balloon to fill the gap 2018 and apply downward pressure to the catheter that forces (arrows 2023) it against the bottom wall 2024 of the immobilizer 2010. This engagement, as well as engagement with the balloon generates holding friction that resists axial (along the axis 2026) pullout of the catheter 2010 from the immobilizer 2000. This arrangement also advantageously moves the catheter to its bottommost orientation so that the distance from the underlying tissue is minimized and predictable.

Figure 20C:
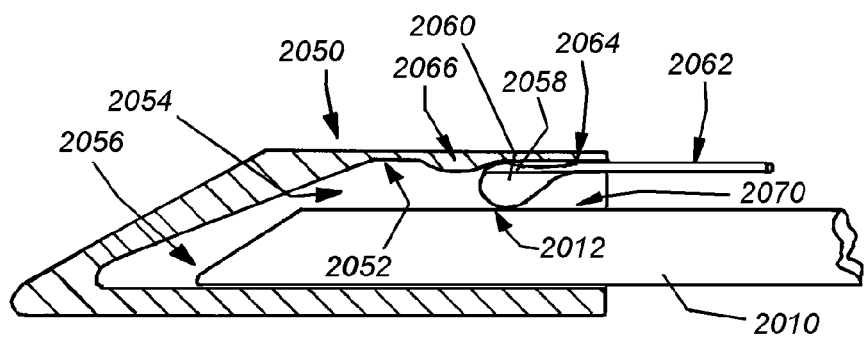
FIG. 20C is a side cross section of an actuatable catheter-holding mechanism in an undeployed/proximally-directed orientation according to an alternate embodiment of the invention.
Figure 20D:
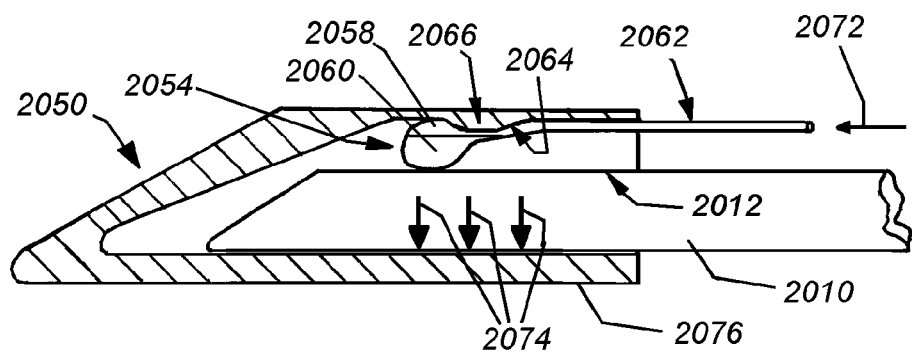
FIG. 20D is a side cross section of the distal immobilizer of FIG. 20C showing the catheter-holding mechanism in a deployed/distally directed orientation.
Figure 20E:
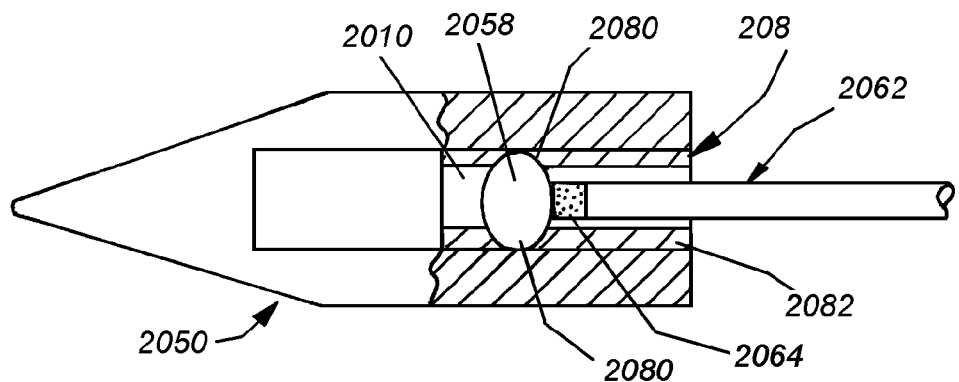
FIG. 20E is a partially exposed top view of the distal immobilizer of FIG. 20C showing the catheter-holding mechanism in a deployed/distally directed orientation.

As described herein, many functions, such as steering and actuation can be implemented using mechanical push-pull mechanisms, which are either manually or mechanically (using electrical, pneumatic or hydraulic actuators) actuated by the user at the control system-end. FIGS. 20C-20E shows a version of the distal immobilizer 2050 that houses the catheter 2010 similarly to the immobilizer 2000 above. This immobilizer 2050 includes a mechanically actuated, push-pull catheter locking mechanism according to an alternate embodiment of this invention. The top wall 2052 of the immobilizer 2050 defines a gap 2050 that allows some lateral movement in the catheter 2010 with respect to the catheter lumen 2056.

A sliding base 2058 having an elastomeric contact surface 2060 rides axially along the top wall 2052. The sliding base 2058 is interconnected with a flexible shaft 2062 that extends proximally back through the proximal immobilizer (proximal components not shown), and back through the cannula to the control system. An appropriate lumen in the proximal immobilizer and cannula can be provided to guide this shaft 2062 and any other push-pull flexible shaft(s) described herein. Within the top side of the base 2058 and/or shaft 2062 is defined a detent 2064. The detent is adapted to ride over a domed locking projection 2066 formed in the top wall 2052 of the immobilizer lumen 2056. In a retracted position as shown in FIG. 20C, the flexible shaft 2062 positions the base 2058 proximally of, and out of engagement with the projection 2066. In this position, a gap 2070 exists between the top 2012 of the catheter 2010 and the bottom of the contact surface 2060 of the locking mechanism.

When the catheter is appropriately axially positioned within the lumen 2056, the shaft 2062 is slid distally (arrow 2072) by the user. Note in FIG. 20E that the base includes side wings 2080 that are adapted to ride on slots 2082 formed in the immobilizer's top. This sliding action causes the base 2058 to ride over the projection 2066 until the detent 2064 comes in to engagement with the projection 2066 as shown in FIGS. 20D and 20E. In this position, the gap 2070 is closed and the elastomeric contact surface 2060 is elastically deformed as it bears pressurably against the top 2012 of the catheter. This provides a frictional hold against the catheter 2010, and also causes the catheter to bias (arrows 2074) against the bottom 2076 of the immobilizer 2050. The pressure is sufficient to resist axial pullout of the catheter relative to the lumen 2056. This mechanism can alternately be applied to the proximal immobilizer or cannula. To release the holding pressure, the user draws the shaft 2062 distally to move the base 2058 out of engagement with the projection 2066. This again defines the gap 2070 between the catheter top 2012 and the contact surface 2060.

It should be clear that a variety of mechanisms can be adapted to lock the catheter with respect to the AGE or AID lumen. These mechanisms can be driven by a variety of motive forces including, but not limited to, manual force, electromagnetics, pneumatics and hydraulics. In some embodiments, a catheter may include an integral detent, or other catch structure, that engages a selectively deployed latch to effect holding.

Figure 21:
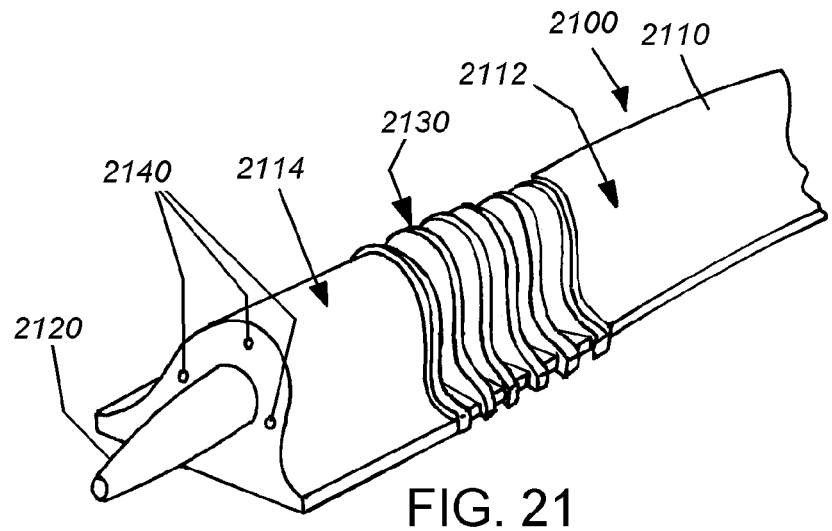
FIG. 21 is a top perspective view of an AID or AGE having a flexible bellows-like, mid-section joint to assist in actuation and steering functions with respect to a tissue surface.
Figure 22:
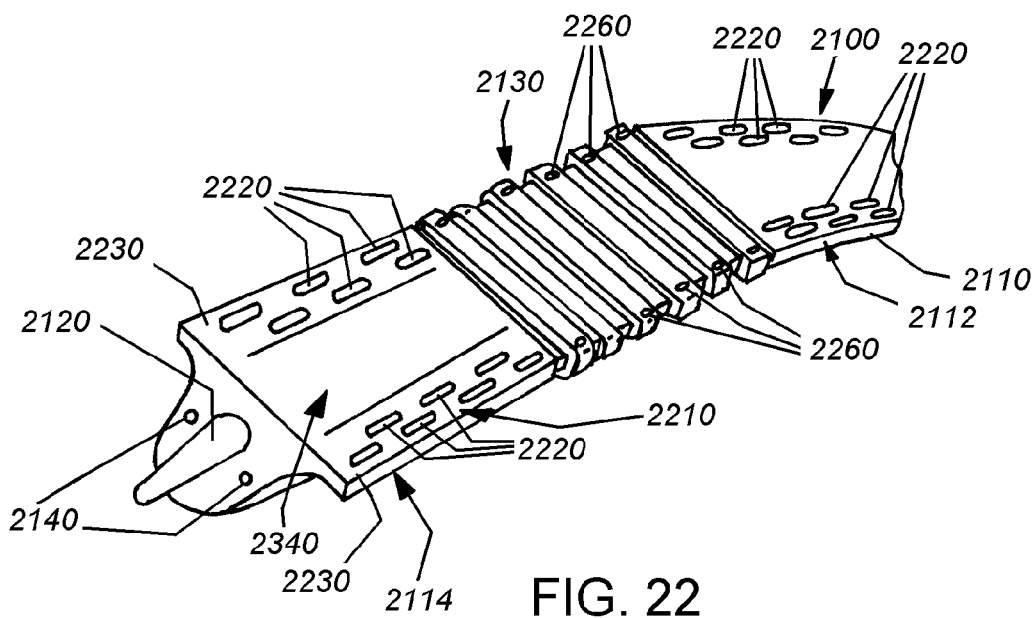
FIG. 22 a bottom perspective view of the AID of FIG. 21.

As described above, both the AGE and AID implementations described herein include a variety of port assemblies along their base in order to transmit a vacuum to the underlying tissue. As shown in FIG. 21, an exemplary AGE 2100 includes an omega-shape body 2110 with a proximal portion 2112 and a distal portion 2114 that each houses a catheter 2120. A bellows-like region 2130 is provided between the proximal and distal sections 2112 and 2114. In an AID configuration, this accordion-like bellows shape allows bending of the sections 2112 and 2114 relative to each other for guidance and steering using, for example, embedded steering wires 2140. As shown further in FIG. 22, the bottom side/base 2210 of the device 2100 includes a series of ports 2220, which are shaped generally as elongated ovals in this embodiment. Alternatively the ports 2220 can be round, or any other acceptable shape. The depicted ports 2220 are disposed in a staggered arrangement along each respective base side 2230 on opposite sides of the central region 2340 that directly underlies the catheter 2120. The base sides 2230 form outwardly-extended flanges (the bottom of the "omega") that allow the hold-down vacuum to be transmitted to the base (and hence, transmitted to the underlying tissue) over a significant surface area while still allowing the central lumen to remain largely exposed to the underlying tissue when desired without interfering ports and other structures. In this embodiment, additional side ports 2260 are also provided along the bellows region 2130 to allow to be secured to the tissue for further overall stability.

As described herein certain embodiments of the AID and AGE allow for continually opened, or selectively opened regions on the bottom, to afford direct exposure of the catheter to the underlying tissue. In other embodiments in which the bottom is substantially (or fully) closed this bottom region should be constructed from a material with high microwave transmissivity.

In an alternate AGE configuration, the distal and proximal ports can be separately accessed by independent vacuum sources to thereby allow self-ambulatory, traversing or crawling motion. Alternatively, all ports can be connected to a common vacuum source to allow hold-down of the entire device at once in an AID configuration. In a further alternate embodiment, in an AID configuration, the distal portion 2114 can be connected to a separate vacuum source so as to allow it to steer, while at least a portion of the AID (such as the proximal portion 2112) maintains vacuum engagement with the underlying tissue. In general however (and as noted above), the various AID embodiments herein are typically implemented as a non-steering, passively applied hold-down device, which piggy-backs the microwave or other type of catheter.

IV. Actuation of Immobilizers to Effect AGE Movement

Figure 23:
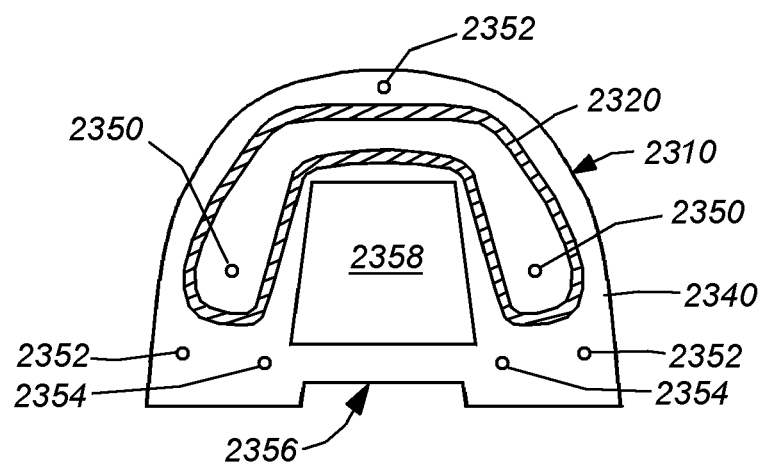
FIG. 23 is a cross section through a mid-section bellows of an AGE or AID adapted for either pneumatic, hydraulic or cable-based steering.
Figure 24:
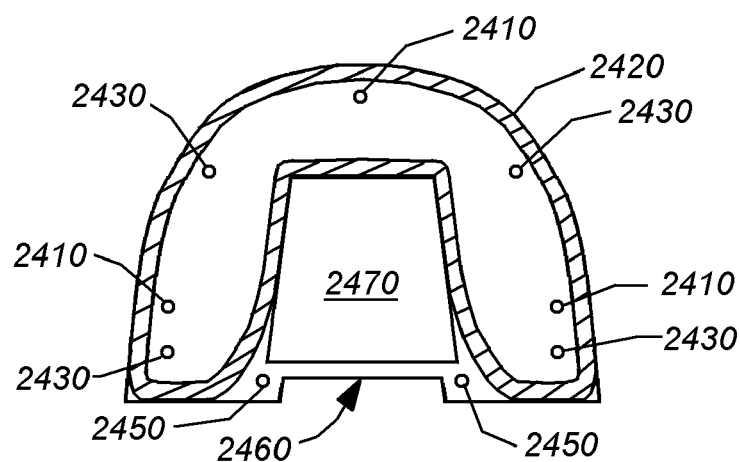
FIG. 24 is a cross section through an immobilizer of the AGE or AID of FIG. 23.

A variety of techniques can be used to actuate movement so as to generate the desired traversing motion in an AGE. These techniques can include hydraulic and pneumatic actuators, screw drives, mechanical push-pull mechanisms and electromagnetic drives. Two basic AGE pneumatic bellows actuation embodiments are shown in cross section, FIGS. 23 and 24 is now described in further detail. With reference first to FIG. 23, the immobilizer body 2310 is shown with a cross-section taken through and interconnected bellows 2320. This bellows 2320 is sealed against the proximal immobilizer 2340 and also against distal immobilizer (not shown) to prevent gas leaks. The proximal immobilizer channels a pair of pressure lumens 2350 into the bellows 2320. A set of steering wires 2352 reside outside the bellows, exposed to the environment. A pair of vacuum channels 2354 also pass selectively into each of the immobilizers to control the vacuum within the central vacuum base 2356 of each immobilizer. A central lumen 2358 is provided for the catheter. By applying positive and/or negative pressure to the lumens 2350, the bellows can be extended or contracted, respectively, allowing the proximal immobilizer 2340 to move (away or toward, respectively) relative to the distal immobilizer. While not shown, the immobilizers can be joined by a second outer sheath with a bellows-like geometry that covers the exposed steering wires and other structures, which extend between the two immobilizers. This assists in preventing the tangling or clogging of these components in bodily tissue.

The embodiment of FIG. 24 differs from that of FIG. 23 in that the steering wire lumens 2410 reside within the enclosure of the bellows 2420. The pressure vacuum lumens 2430 provide needed pressure to expand and contract the bellows 2420. A pair of vacuum immobilizer lumens 2450 selectively provide a vacuum hold-down force to each of the vacuum chambers 2460. These lumens 2450 are isolated from the environment of the bellows so as to maintain a separate vacuum state for use at the vacuum chambers 2460 of the immobilizers. An internal lumen 2470 for the catheter is provided above the vacuum chamber 2460. The steering wire lumens 2410, must be appropriately sealed relative to the volume defined by the bellows 2420 so that vacuum pressure is not lost due to the fact that they pass through the otherwise sealed area or the bellows.

Figure 25:
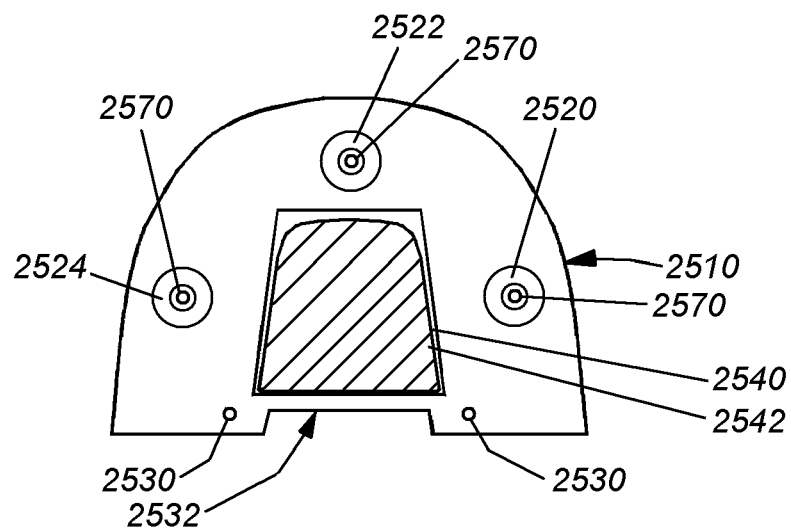
FIGS. 25-28 are each embodiments of mid-section cross sections of pneumatic or hydraulic multiple-bellows steering mechanisms for an AGE.

In alternate embodiments, both actuation of movement between the proximal and distal immobilizers and steering therebetween can be effected using a single force, namely pneumatic or hydraulic pressure. As shown in FIG. 25, a distal immobilizer 2510 is provided with three independently operated bellows 2520, 2522 and 2544. A pair of separate vacuum lumens 2530 are also provided to impart the necessary hold-down force to the vacuum chamber 2532. A central lumen 2540 for a catheter 2542 is also provided. By selectively actuating, with appropriate pressure and/or vacuum each of the bellows, the distal immobilizer can be moved in any direction, including forwardly at an appropriate angle, with respect to the proximal immobilizer.

Figure 26:
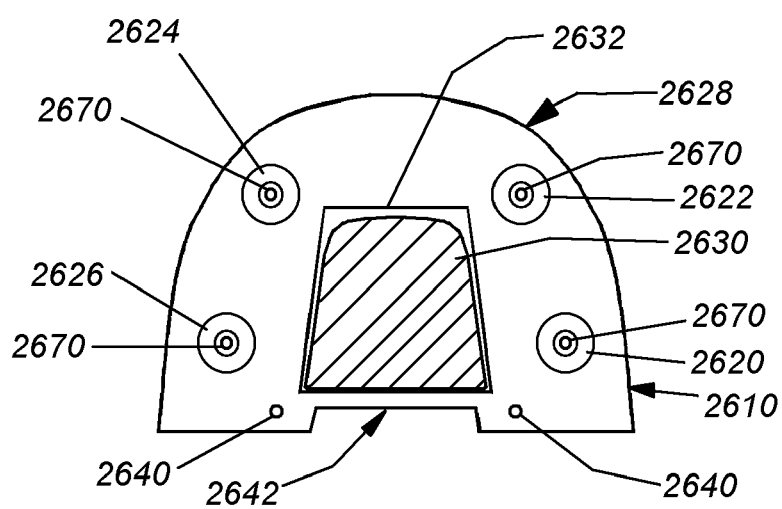

FIG. 26 shows the distal end of an immobilizer 2610 that includes four bellows 2620, 2622, 2624 and 2626 that are arranged appropriately around the external perimeter 2628 of the immobilizer. Likewise, a catheter 2630 is provided within an appropriate lumen 2632 and a pair of vacuum lumens 2640 supply each of the vacuum chambers 2642 to provide hold-down force.

Figure 27:
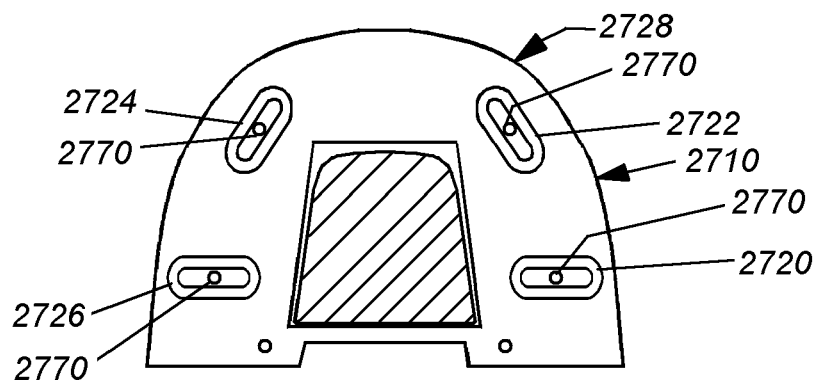
Figure 28:
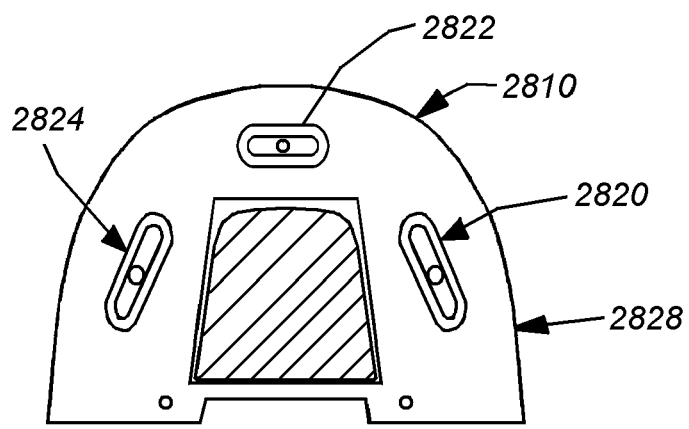

While the bellows in FIGS. 25 and 26 are circular and, generally, concentric about their appropriate vacuum lumens 2570 and 2670, respectively, it is contemplated that the bellows can provide increased size/volume by providing them with an elongated cross-section. In FIG. 27, the proximal immobilizer 2710 includes a pair of somewhat ovular-cross-section bellows 2720, 2722, 2724 and 2726 located in an efficient arrangement about the perimeter 2728 of the immobilizer 2710. Each of these bellows is fed by an appropriate vacuum lumen 2770 that, like other bellows and lumens described herein, is in sealed communication with the proximal control system. Through use of the appropriate valves, each bellows can be selectively operated to generate a positive pressure and/or vacuum as appropriate to steer and/or advance the distal immobilizer with respect to the proximal immobilizer. A similar elongated-cross-section-bellows arrangement is shown for the immobilizer 2810 of FIG. 28. Three bellows 2820, 2822 and 2824, sized appropriately, are provided about the perimeter 2828 of the immobilizer. Note that, in each of these embodiments, the lumen that transmits fluid to and from each bellows extends generally through the proximal immobilizer while the corresponding mating connection and the distal immobilizer is typically lumen-free, with the bellows simply establishing a sealed connection against the proximal end of the distal immobilizer (not shown). In this manner fluid is either withdrawn from the bellows chamber or forced into the bellows chamber without being passed into the distal immobilizer.

One advantage to each of the above-described small-diameter, independent bellows is that they may require less total airflow/fill time to effect actuation over a given distance. This is because they collectively occupy a smaller overall volume than the larger-volume bellows described above with reference to FIGS. 23 and 24.

Figure 29:
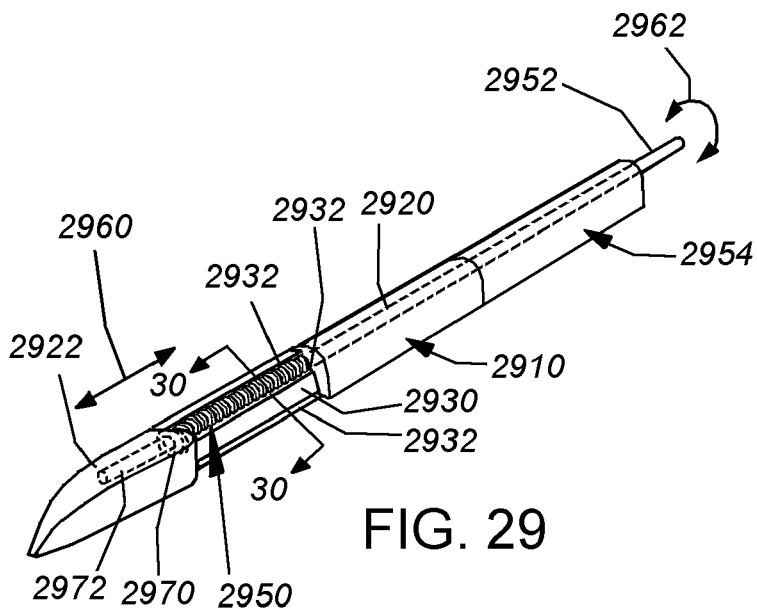
FIG. 29 is a perspective view of an AGE having a helix drive movement actuation system according to an embodiment of this invention.
Figure 30:
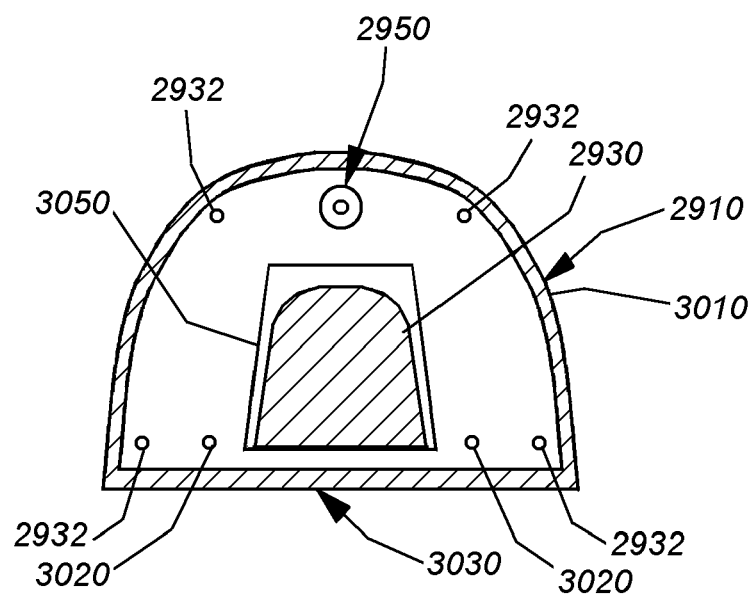
FIG. 30 is a cross section of the AGE taken along line 30-30 of FIG. 29 showing the drive sheath.

An alternate type and embodiment of actuating/advancing mechanism is shown in FIGS. 29 and 30. The depicted AGE 2910 consists of a proximal immobilizer 2920 and a distal immobilizer 2922 of a general size and shape similar to those described above. The bellows between the immobilizers 2920 and 2922 has been omitted from FIG. 29 for clarity. This bellows 3010 is shown in cross-section in FIG. 30. As described below, the bellows 3010 is only meant to provide a compressible/expandable cover the internal components between immobilizers in this embodiment, and not to provide an actuation mechanism.

In this embodiment, the proximal immobilizer 2910 and distal immobilizer 2922 are interconnected by steering wires 2932. These wires 2932 can be independently tensioned to allow the distal immobilizer 2922 to move angularly with respect to the proximal immobilizer 2920. Vacuum lumens 3020 pass between the proximal immobilizer and the distal immobilizer to allow the proximal immobilizer 2920 to be selectively provided with hold-down vacuum force relative to the distal immobilizer 2922 as desired. The catheter 2930, which spans between the proximal and distal immobilizers, is located to direct its energy downwardly through the base (3030 in FIG. 30).

Notably, at the top end of both the proximal and distal immobilizers is mounted an interconnecting flexible helical drive 2950. The helical drive includes a flexible drive shaft 2952 that extends outwardly through the cannula 2954 and back to a rotating mechanism on the guidance system. The flexible helical drive screw 2950 can be constructed from any resilient acceptable polymer or flexible metal lead. In this embodiment one end of the drive 2950 is rotatably fixed, and the opposing end is allowed to rotate within a threaded nut. In this embodiment the nut 2970 is shown (in phantom) embedded in the proximal end of the distal immobilizer 2922. As the helical drive 2950 rotates it rotates through the fixed nut, thereby moving the proximal immobilizer toward and away from the distal immobilizer. A channel 2972 (shown in phantom) is provided distally of the nut to allows run-out room for the advancing drive screw 2950 as the proximal immobilizer drives distally toward the distal immobilizer. The proximal immobilizer in this and other embodiments slides freely along any distally connected lumens, steering wires and the catheter itself 2930 so that it is free to move toward and away from the distal immobilizer. Rotation between the two immobilizers 2920 and 2922 is generally restricted as the screw 2950 rotates due to the triangular shape of the catheter 2930 and the conforming lumen 3050 (FIG. 30). Because the catheter is somewhat flexible, it still allows the needed steering between immobilizers, however. In alternate embodiments, flexible, sliding guide rods can be used to restrict rotation of one immobilizer with respect to the other. These rods can be located separate from other connections between the immobilizers (lumens, steering wires, etc.), or the flexible anti-rotation guide rods can slidably encase some these interconnecting elements between the immobilizers (for example the steering wires).

In an alternate implementation of the helical drive screw of FIGS. 29 and 30, both ends of the screw can include nuts, with an appropriate stop mechanism to prevent over-extension of the ends with respect to each other.

The helical drive mechanism of FIGS. 29 and 30 generally allows the distal and proximal immobilizers to be moved toward and away from each other (double arrow 2960) based upon rotation (double curved arrow 2962) of the shaft 2952. Because the drive screw 2950 is flexible, it allows the steering wires 2932 to bend the distal immobilizer 2922 with respect to the proximal immobilizer 2920, thereby affording steerability as well as linear actuation.

It is contemplated that the above-described helical drive and other helical/rotationally actuated drives described herein can be driven by a stepper, servo, or other type of motor, typically located at the proximal control system. The encoder or other motion control device can employed using the rotational or linear feedback data to provide position feedback information in connection with the immobilizer. Such information can be displayed to the user and/or used to provide automatic control functions to the actuation of the AGE.

Figure 31:
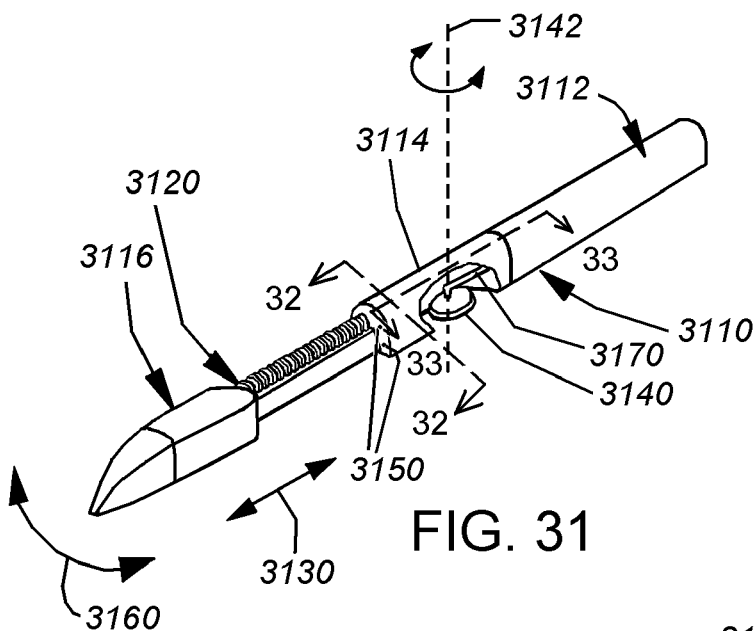
FIG. 31 is a perspective view of a helix-drive-actuated AGE having a pivoting suction cup in its proximal immobilizer according to an embodiment of the invention.
Figure 32:
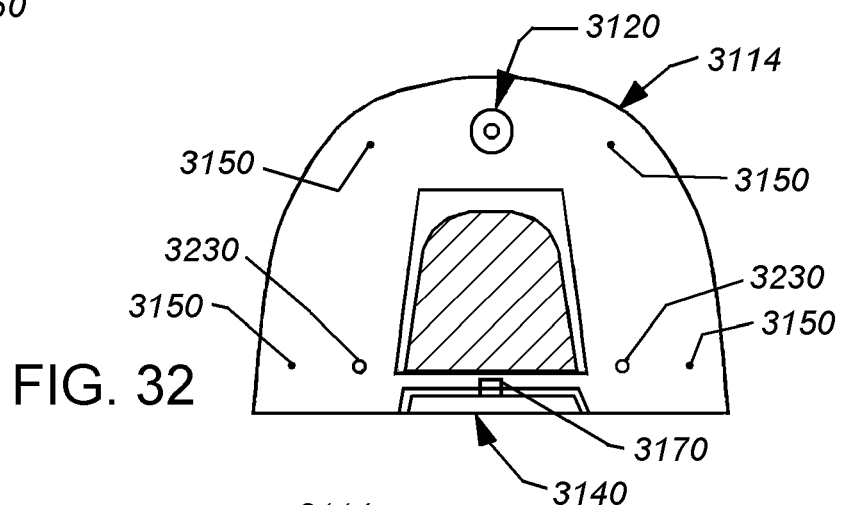
FIG. 32 is a cross section of the proximal immobilizer of the AGE taken along line 32-32 of FIG. 31.
Figure 33:
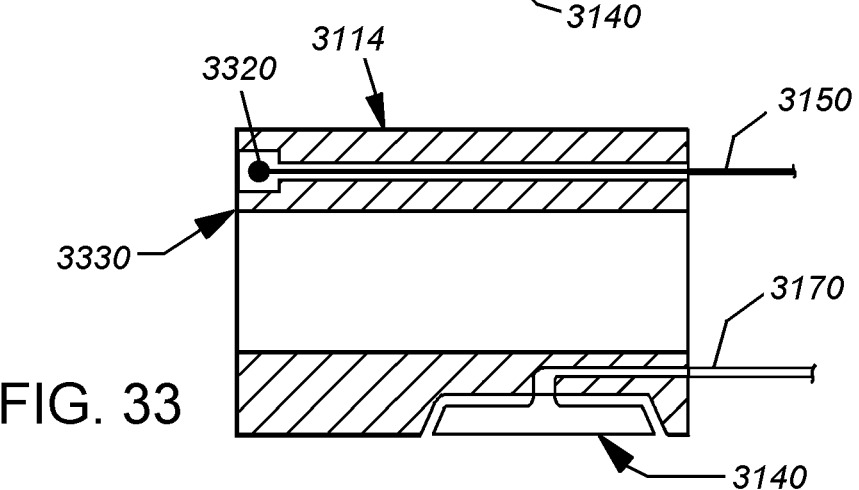
FIG. 33 is a side cross section of proximal immobilizer of the AGE taken along line 33-33 of FIG. 31.

Yet another helical-screw actuation mechanism for an AGE is shown in FIGS. 31-33. The AGE 3110 in this embodiment includes a cannula 3112, proximal immobilizer 3114 and distal immobilizer 3116. The helical drive screw 3120 in this embodiment is rigid, rather than flexible. The screw 3120 engages a nut embedded in the distal immobilizer (not shown) similar to the embodiment of FIGS. 29-30 described above. Hence, the proximal immobilizer 3114 and distal immobilizer 3116 may only move toward and away from each other in a linear manner (straight double-arrow 3130). Steering of the entire AGE in a desired direction is effected by rotating the structure about a pivoting vacuum plate 3140 located at the base of the proximal immobilizer 3114. The vacuum plate is adapted to engage the tissue and acts as the proximal immobilizer's primary hold-down mechanism with respect to underlying tissue. When engaged with tissue, and while the distal immobilizer's vacuum is disengaged, the structure is free to rotate about an axis 3142 through the center of the vacuum plate 3140.

A set of four steering cables 3150 are located about the perimeter of the proximal immobilizer 3114. These steering cables 3150, by selectively tensioning and/or releasing them, allow the proximal end to be manipulated with respect to the axis 3142. As such, the entire AGE end (both proximal and distal immobilizers) can be moved in an appropriate direction (double curved arrow 3160). The pivoting vacuum plate 3140 is fed by a separate vacuum line 3170 that extends back to the guidance system, and is engaged when the proximal end is held down to the tissue. Pivoting is enabled by forming a seal between the vacuum plate and end of the line 3170 that allows rotation of the plate 3140 with respect to the line end. Appropriate lip structures formed between the line and plate, and user of polymers in their construction having low-friction properties can be used to create a rotatable seal in a manner known to those of ordinary skill. Each steering cable is anchored with an anchor well 3320, as shown in FIG. 33 near the distal face 3330 of the proximal immobilizer 3114. Conventional vacuum lumens 3230 are provided in both the proximal immobilizer 3114 to direct appropriate vacuum pressure to the distal immobilizer 3116 so as to generate desired hold down force as needed.

Referring now to FIGS. 34-37, another embodiment of a helical-drive-actuated AGE 3410 is shown. The AGE 3410 includes a proximal immobilizer 3412 and distal immobilizer 3414. The helical drive 3420 is rigid in this embodiment, but is secured along the distal face of the proximal immobilizer 3412 by a flexible rotating joint 3430 that interconnects with a drive shaft 3432. As shown in the cross section of FIG. 35, taken through the omitted outer sheath, a set of steering wires 3520 surround the perimeter and allow the distal immobilizer 3414 to steer angularly (double-curved arrow 3450) relative to the proximal immobilizer 3412 about the flexible joint 3430. To effect this steerable motion, the steering wires 3520 move freely through lumens in the proximal immobilizer, and are anchored in the distal immobilizer. Vacuum lumens 3530 are provided in both the proximal immobilizer, and the distal immobilizer, both being in communication with the control system, and enabling the proximal and distal immobilizers to be separately held down to the tissue by applied vacuum as desired.

Figure 34:
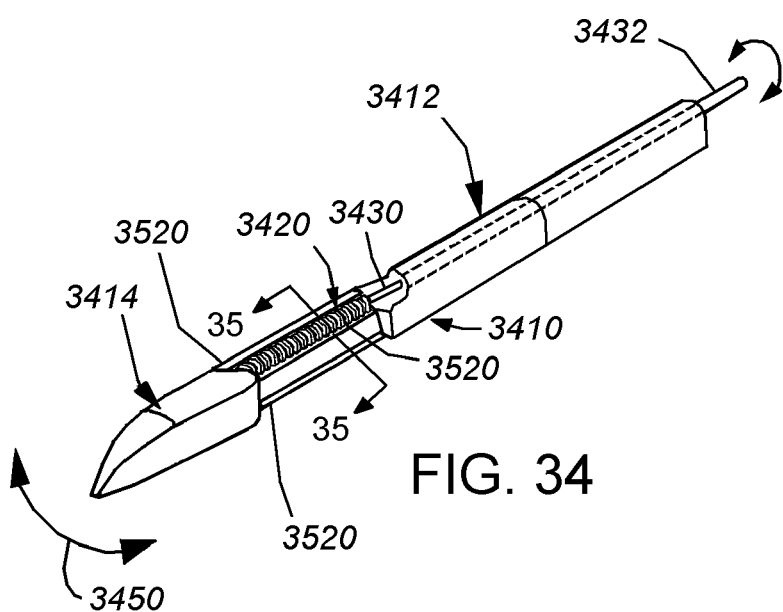
FIG. 34 is a perspective view of a helix-drive-actuated AGE having a flexible coupling for the drive within the proximal immobilizer according to an embodiment of this invention.
Figure 35:
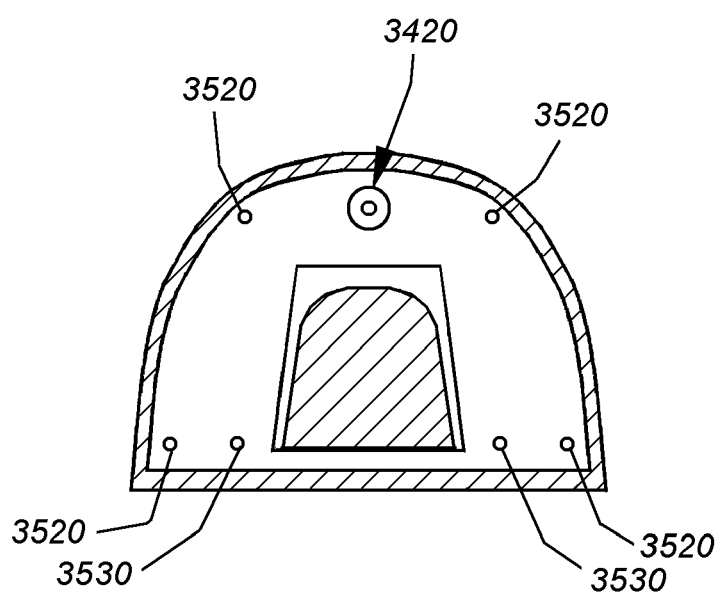
FIG. 35 is a cross section of the AGE taken along line 35-35 of FIG. 34 showing the drive sheath.
Figure 36:
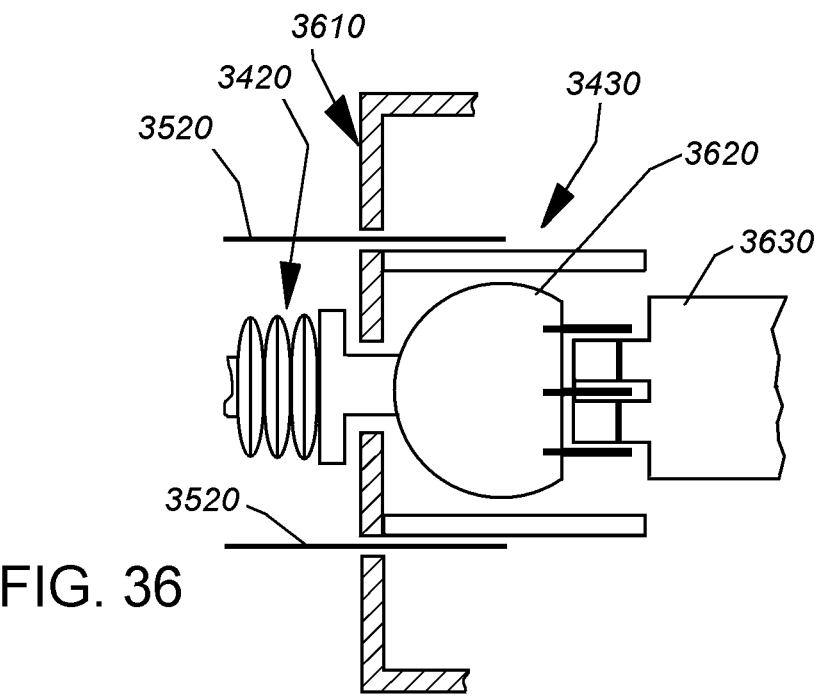
FIG. 36 is a partial cross section showing an embodiment of a flexible joint for the helix drive for the AGE of FIG. 34.

With further reference to FIG. 36, an embodiment of a flexible joint 3430 for use in the AGE of FIG. 34 is shown. This joint extends through the distal face 3610 of the proximal immobilizer from the rigid helical drive screw 3420. In this embodiment, the nut is located within the distal immobilizer. It is contemplated in alternate embodiments that the flexible joint 3430 can be provided at the proximal face of the distal immobilizer. In that case, the nut would be provided within the proximal immobilizer. In the depicted flexible joint 3430 of FIG. 36, the rotating, flexible components consists of a socket 3620 that engages a corresponding ball on the end of the drive shaft 3630. Such a ball and socket arrangement allows for appropriate rotation of one member with respect to the other, at angular deflections from linear. The construction of such a ball and socket joint and should be clear to those of ordinary skill.

Figure 37:
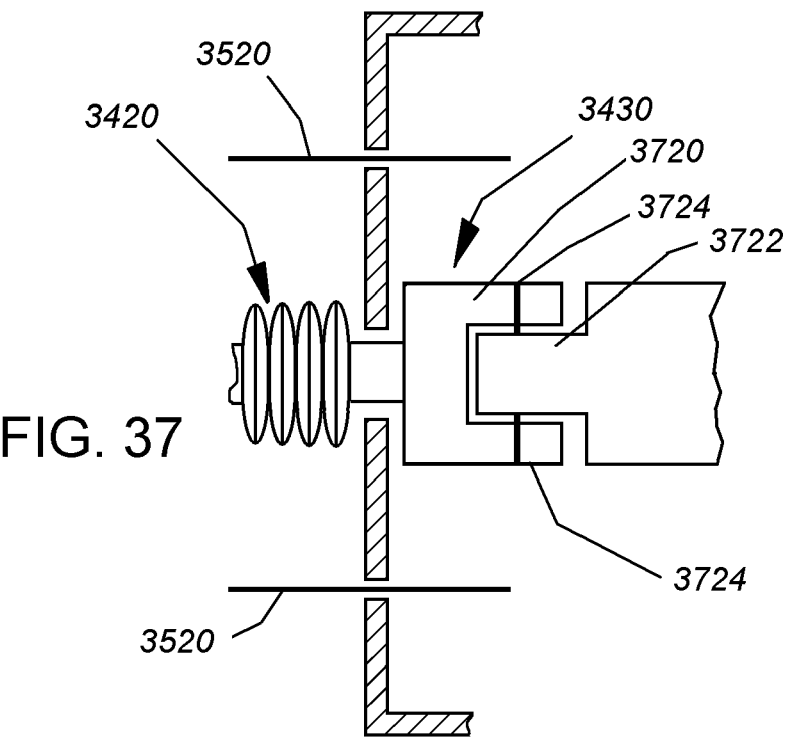
FIG. 37 is a partial cross section showing another embodiment of a flexible joint for the helix drive for the AGE of FIG. 34.

In an alternate embodiment of the flexible joint 3430, shown in FIG. 37, the end of the helical drive 3420 includes a slotted clevis 3720 that engages an overlapping universal joint base 3722 with rotating pins 3724 passing out of the base 3722 and into opposing sides of the overlapping clevis 3720. This arrangement is similar to the universal joint found in most automobiles and its construction known to those of ordinary skill.

Figure 38:
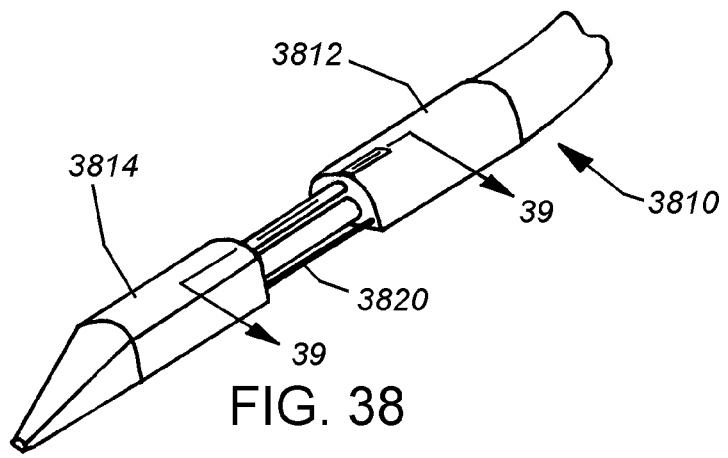
FIG. 38 is a perspective view of a pneumatic/hydraulic piston-actuated AGE according to an embodiment of the invention.
Figure 39:
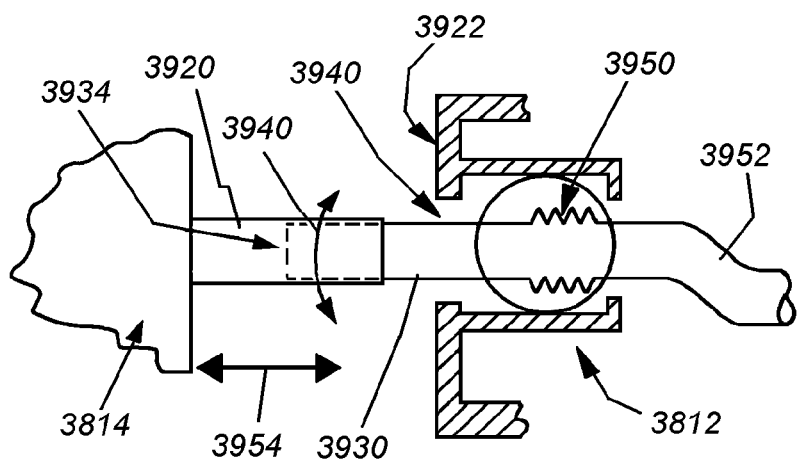
FIG. 39 is a partial side cross section of the AGE including the piston assembly taken along line 39-39 of FIG. 38.

Another inventive type of pressure-driven AGE articulation system, according to an alternate embodiment, is shown in FIGS. 38 and 39. The AGE 3810 consists of a proximal immobilizer 3812 and a distal immobilizer 3814 that are joined by steering cables 3820 that are configured and operate similarly to those described above. That is, the cables move freely through the proximal immobilizer 3812, and are anchored in the distal immobilizer 3814 and tensioning of selected cables causes the distal immobilizer to point ant a non-linear (off-axis) angle with respect to the proximal immobilizer. As shown in the partial cross section in FIG. 39, the distal immobilizer 3814 includes a rigid or semi-rigid sleeve 3920 that extends proximally toward the distal face 3922 of the proximal immobilizer 3812. A nested sleeve 3930 extends into the overlapping sleeve 3920. The nested, smaller diameter sleeve 3930 is open at its distal end 3934 allowing pressure and/or vacuum to fill the space within the overlapped sleeves. The outer diameter of the nested sleeve 3930 is closely matched to the inner diameter of the overlapping sleeve 3920, or one or more sealing rings are disposed between the sleeves. In either arrangement, a relative gas seal is created between the two overlapping sleeves 3920 and 3930. By alternately pressurizing or evacuating the lead pipe 3952, the sleeves are moved away or toward each other, respectively.

A gap 3940 is formed in the face 3922 of the proximal immobilizer around the sleeve 3930. This gap is sufficient to allow a degree of angular steering movement (double-curved arrow 3940) of the sleeves 3920 and 3930 with respect to the face 3922. In addition a flexible accordion-like bellows 3950 is provided on the lead pipe 3952 of the sleeve arrangement to allow the sleeve arrangement to pivotally bend along the bellows during steering. Hence, the distal immobilizer 3814 can pivot or steer with respect to the proximal immobilizer 3812 without binding up the two overlapping sleeves. This lead pipe, 3952 extends back to a pressure/vacuum source at the control system. These sleeves act, in essence, as a bi-directional piston. Because there is a gap 3940, the steering cables are allowed to steer the distal immobilizer with respect to the proximal immobilizer and linear movement (double arrow 3954) is accomplished using the sleeve arrangement.

Figure 39A:
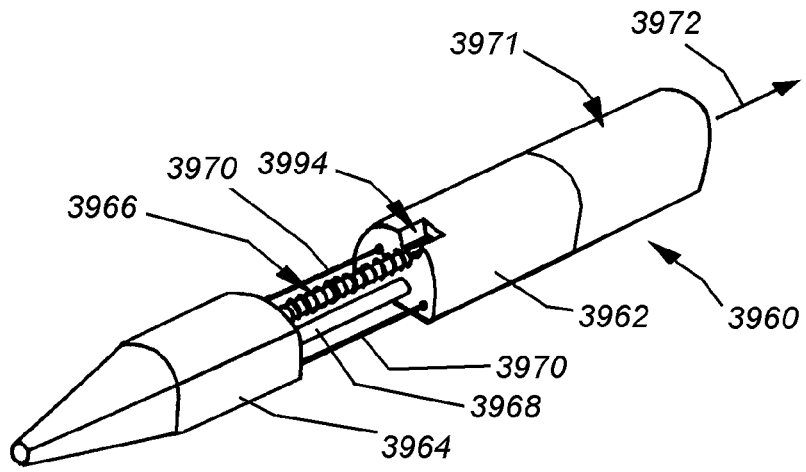
FIG. 39A is a perspective view of an electromagnetically actuated AGE according to an embodiment of the invention.

FIG. 39A shows an embodiment of an AGE 3960 based upon a linear actuator, which includes a proximal immobilizer 3962 and distal immobilizer 3964 that are actuated based upon an electromagnetic actuation assembly 3966. The AGE 3960 in this embodiment includes a catheter 3968 in accordance with any of the embodiments described herein. The AGE is steered by a plurality of steering wires 3970 that extend between the proximal immobilizer 3962 and the distal immobilizer 3964. A variety of steering mechanisms can be used in alternate embodiments, as described above. The proximal immobilizer 3962 is attached to a proximally directed cannula 3971. The cannula extends approximately (arrow 3972) back to the control system. It carries the electrical wires for powering the actuator, and other components used to operate the AGE movement mechanism.

Figure 39B:
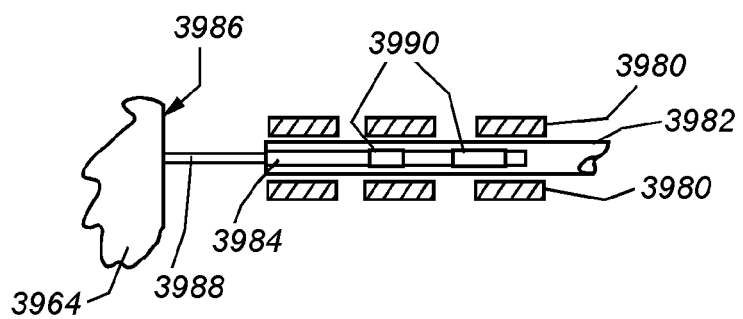
FIG. 39B is a more detailed fragmentary cross section of a portion of the electromagnetic actuator for the AGE of FIG. 39A.

The actuation assembly is shown in partial cross section in FIG. 39B. Generally, it consists of a linear motor winding (wire coils) 3980. The coils surround a shaft 3982 that extends between the proximal immobilizer and end point 3984 that is spaced remote from the proximal face 3986 of the distal immobilizer 3964. A second shaft 3988 is fixed to the proximal face 3986 of the distal immobilizer 3964. The second shaft 3988 carries magnets 3990 or another form of magnetic material. It is nested, and rides within, the larger diameter shaft 3982. When the coils are energized with one of two respective polarities, the shafts 3982, 3988 collectively move in each of two respective directions, depending upon the polarity. This allows the distal immobilizer 3964 to be moved toward and away from the proximal immobilizer 3962. A flexible joint 3994 (FIG. 39A) is provided at the proximal immobilizer. This joint 3994 can be any acceptable flexible coupling that hinges in two degrees of freedom, including a section of flexible polymer material to which the shaft 3982 is connected in the region of distal face of the proximal immobilizer 3962. It should be clear that a variety of arrangements of linear motors consisting of magnetic members and coils that slide with respect to each other can be implemented according to alternate embodiments, within the general teachings of this embodiment.

Figure 40:
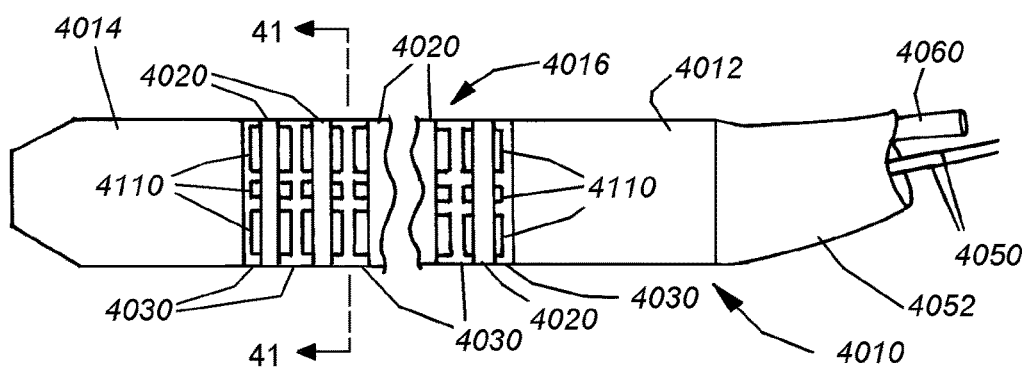
FIG. 40 is a side view of an embodiment of an AGE having an electromagnetic actuator for orienting, advancing and retracting the distal immobilizer with respect to the proximal immobilizer.
Figure 41:
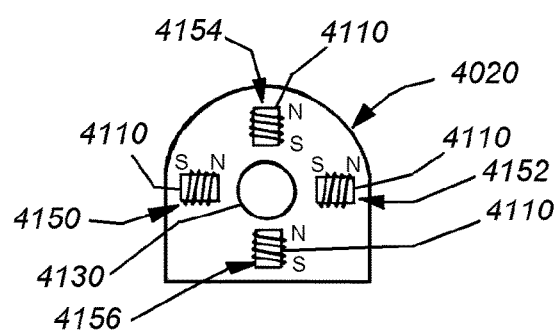
FIG. 41 is a cross section of the AGE actuator taken along line 41-41 of FIG. 40.

Another inventive type of system for AGE actuation and steering is shown in FIGS. 40 and 41. The AGE 4010 in this alternate embodiment comprises a proximal immobilizer 4012 and a distal immobilizer 4014 having any acceptable vacuum hold-down arrangement to facilitate selective engagement to underlying tissue. Alternatively, a micro-needle hold-down arrangement of a type generally described herein, or another hold-down mechanism, can be provided. The central portion 4016 of the AGE 4010 consists of pairs of disks 4020, one of which is shown in plan view in FIG.

41. Each of the disks 4020 opposes another disk. The number of disks 4020 is highly variable. Between the opposing disks, in one exemplary embodiment, is provided a ring of flexible material 4030. The flexible material 4030 provides elastic resistance to separation between the opposed disks, and limits their outward expansion and maintains rotational alignment therebetween. As discussed below in other embodiments, disks can be held in alignment and expansion can be limited using other forms of guide mechanisms.

Each disk includes a plurality of electromagnets 4110 on each of opposing faces thereof. The electromagnets are arranged so that when they are energized through wires 4050 (that extend along the cannula 4052 to the control system), the magnets in opposing disks 4020 each repel or attract each other when electrically powered, and cause the elastic material 4030 therebetween to stretch. By energizing only selected of the electromagnets around the circumference of various disk pairs, the stretch occurs differentially, causing the overall middle section 4016 to expand in a non-linear, non-axial (turning) direction. The electrical wires can be arranged to individually address certain magnets, or groups of magnets in order to obtain the appropriate degree of turn. Using known techniques, the control system can be adapted to provide variable levels of voltage or current to selected magnets.

In an alternate embodiment, the flexible material between disks is omitted and the rigid disks are contained within a cannula or tubing (or another alignment structure, such as guide wires) and move toward and away from each other under alternate activated magnetic attraction or repulsion. To conduct a flat turn in a first direction, for example, all magnets at the depicted 9 o'clock position 4150 are made to repel, while all magnets at the depicted 3 O'clock position 4152 are made to attract—and vice versa for a turn in an opposing, second direction. Climbing employs the 12 o-clock (4154) and 6 o'clock (4156) magnets. Magnets can remain aligned and maximum expansion can be limited by the guide wires, tubing, or other structures that pass through or along the disks 4020. The number and placement of individual magnets about the perimeter is highly variable. In general the magnets should be placed so that balanced turns can be achieved using the control system provided. A control system may be adapted to provide variable power to various magnets to control the turn, or a more simplified control can employ an incremental (or simple on/off) voltage to the magnets.

It should be clear that in this, and other embodiments herein, using more conventional steering cables, that turning can occur not just along one plane, but along orthogonal planes, thereby providing the full range of point ability to the distal immobilizer. This allows it to climb and dive, as well as to move left and right.

An orifice 4130, of appropriate size and shape is provided through the disks, and through the proximal and distal immobilizers 4012 and 4014. This allows the therapeutic catheter 4060 to pass therethrough and reside therein. Also, as in other embodiments described herein, movement is accompanied by selective application of vacuum to each of the proximal immobilizer and distal immobilizer.

In operation, a typical movement cycle for the AGE 4010 would entail application of vacuum to the proximal immobilizer, while releasing vacuum on the distal immobilizer, causing expansion in the middle section 4016 via electrical energy, reseating, by vacuum, the distal immobilizer 4014, and then releasing the proximal immobilizer to allow the elastic material 4030 to contract, thereby drawing the proximal immobilizer forward. Differential energizing of certain magnets causes turning during the cycle and the resulting turn is finalized by securing the distal immobilizer to the tissue by vacuum.

Figure 42:
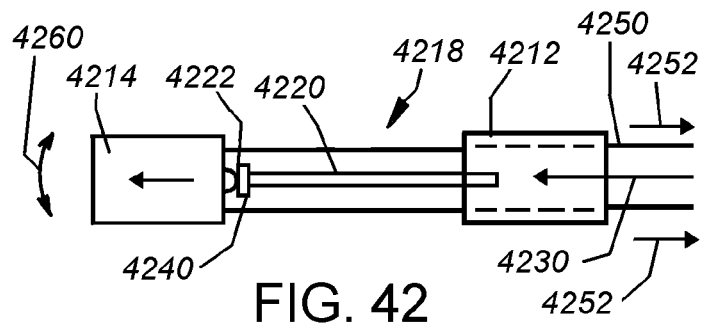
FIGS. 42-48 are schematic diagrams detailing various systems that combine actuation and steering between the proximal immobilizer and the distal immobilizer of an AGE, according to various embodiments of the invention.

FIGS. 42-48 detail a variety of mechanisms that allow a proximal immobilizer and distal immobilizer to be actuated and steered with various common elements. Each mechanism will be described briefly in turn. In FIG. 42, the proximal immobilizer 4212 and the distal immobilizer 4214 are joined by a push mechanism 4220 that passes slidably through the proximal immobilizer, across a gap 4218, and then against the proximal face 4222 of the distal immobilizer 4214. The push mechanism 4220 extends back to the control system and can be actuated by hand or electromechanically by the user. By pushing forward (arrow 4230), the distal immobilizer is moved forwardly relative to the proximal immobilizer. The proximal face 4222 of the distal immobilizer 4214 includes a spherical surface that allows rotation (during steering) relative to the flattened end 4240 of the push mechanism 4220 within a limited range. The steering direction of the distal immobilizer 4214 is controlled by a plurality of steering cables 4250 that are selectively pulled (arrow 4252) to provide steering (double-curved arrow 4260) to the distal immobilizer 4214.

Figure 43:
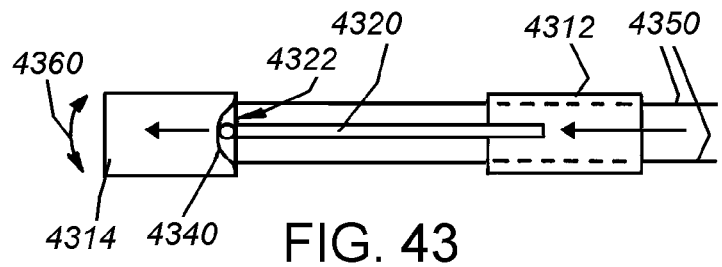

FIG. 43 shows an embodiment of a push-pull proximal immobilizer 4312 and distal immobilizer 4314 that operate on principles similar to those described with respect to FIG. 42. In this embodiment, the distal immobilizer includes a proximal concave well 4322 upon which the push mechanism 4320 bears. This well allows a ball shaped distal end 4340 on the push mechanism to rotatably engage the distal immobilizer 4314. Steering cables 4350 are pulled to orient the distal immobilizer 4314 in the appropriate steering direction 4360 while the resulting ball (4340) and socket (4322) allow limited steering rotation.

Figure 44:
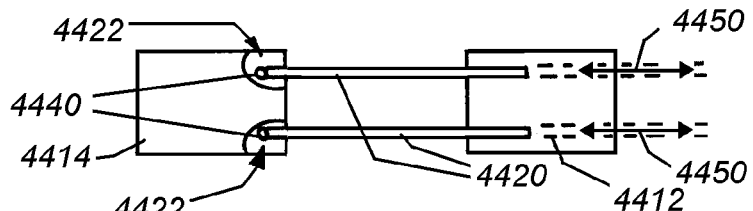

FIG. 44 shows a proximal immobilizer 4412 and a distal immobilizer 4414 according to another push-pull embodiment in which a plurality of push-pull mechanisms 4420 (typically, two, three or four separate push-pull shafts) pass slidably through the proximal immobilizer 4412, and out through the proximal control system. The distal ends 4440 of each push-pull mechanism ride in a respective concave well 4422 that allows for selective pushing and pulling (double arrows 4450) of any of the push-pull shafts 4420 to both advance the distal immobilizer 4414, with respect to the proximal immobilizer 4412 and angularly orient the distal end in the desired steering direction. Orientation is achieved by pushing and/or pulling one push-pull mechanism 4420 a further or lesser distance than other push-pull mechanisms. The rotation of the distal immobilizer is taken up by the rotatable engagement between the wells 4422 and distal ends 4440 of the push-pull mechanisms.

Figure 45:

In the alternate push-pull embodiment of FIG. 45, the proximal immobilizer 4512 and distal immobilizer 4514 are shown which a pair of linear push-pull mechanisms 4520 are controlled (double arrows 4550) by the control system. They pass through the proximal end and allow for advancing of the distal immobilizer 4514 with respect to the proximal immobilizer 4512. Steering is accomplished similarly to the AGE embodiment having the pivoting suction cup, as shown and described above with reference to FIGS. 31-33. The pivoting suction cup 4560 of the present embodiment rotates both the proximal and distal immobilizers 4512 and 4514 as a joined structure based upon steering cables (not shown) that are anchored in the proximal immobilizer (similar to those of FIGS. 31-33).

Figure 46:
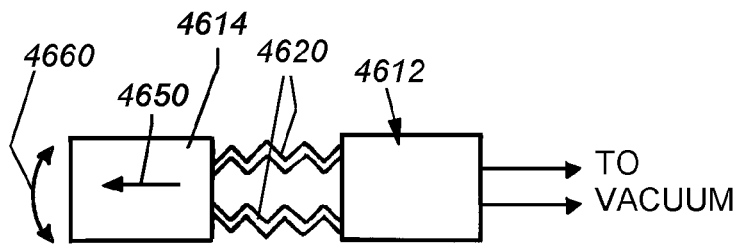

FIG. 46 details a basic embodiment of a bellows-operated AGE with a proximal immobilizer 4612 and a distal immobilizer 4614 that are joined by a plurality of selectively operable bellows 4620. Each bellows 4620 is operated by a vacuum and/or pressure source at the control system. The bellows can be inflated together to advance the distal immobilizer 4614 in a straight linear/axial direction (arrow 4630), or the bellows 4620 can be individually operated to steer (double-curved arrow 4660) the distal immobilizer 4614 in any desired angular direction with respect to the proximal immobilizer 4612. Various versions of this implementation are also shown in cross-section in FIGS. 25-28, described above.

Figure 47:
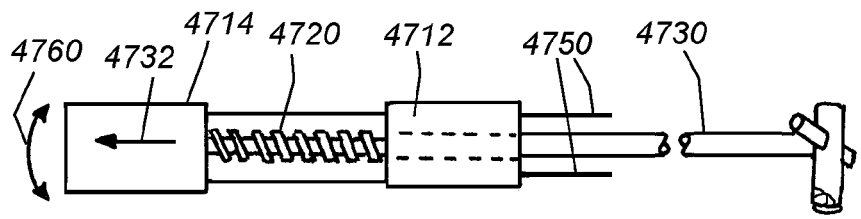

In the exemplary embodiment of FIG. 47 a proximal immobilizer 4712 and distal immobilizer 4714 are joined by a lead screw 4720 that extends out to a manual control 4730. The manual control allows the overall movement (arrow 4732) of the distal immobilizer 4714 with respect to the proximal immobilizer 4712. In this embodiment the lead screw is flexible so that movement of steering cables 4750 while steering (double-curved arrow 4760) of the distal immobilizer 4714. The hand-control 4730 can be substituted for a motorized control as appropriate. This arrangement is similar to that described above with reference to FIGS. 29 and 30.

Figure 48:
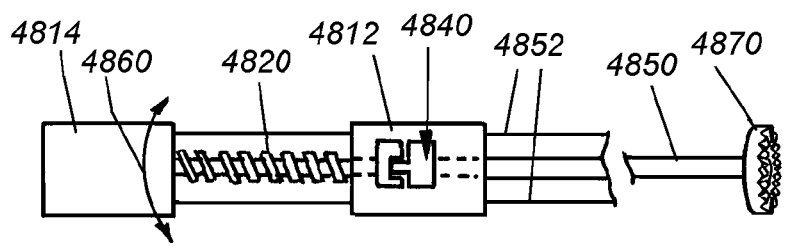

Alternatively, as shown in exemplary embodiment of FIG. 48 the proximal immobilizer 4812 and the distal immobilizer 4814 can be joined by a somewhat rigid lead screw 4820. Note that both lead screws 4720 and 4820 typically engage a nut (not shown) embedded in the proximal end of the distal immobilizer 4714 and 4814. In this embodiment, a flexible joint 4840 allows the lead screw 4820 and distal immobilizer 4814 to pivot together (double-curved arrow 4860) about the joint 4840. The distal portion of the drive shaft 4850 extends out to the control system where it engages a geared drive 4870. Steering wires 4852 extend through the proximal immobilizer 4812 to join the distal immobilizer 4814 so that steering can be controlled by selective pulling on the steering wires 4850 at the control system end. This arrangement is similar to that shown in FIGS. 34-37.

It should be clear that a variety of other implementations for steering and actuation can be implemented in accordance with this invention.

V. AGE and AID Steering Mechanisms

Figure 49:
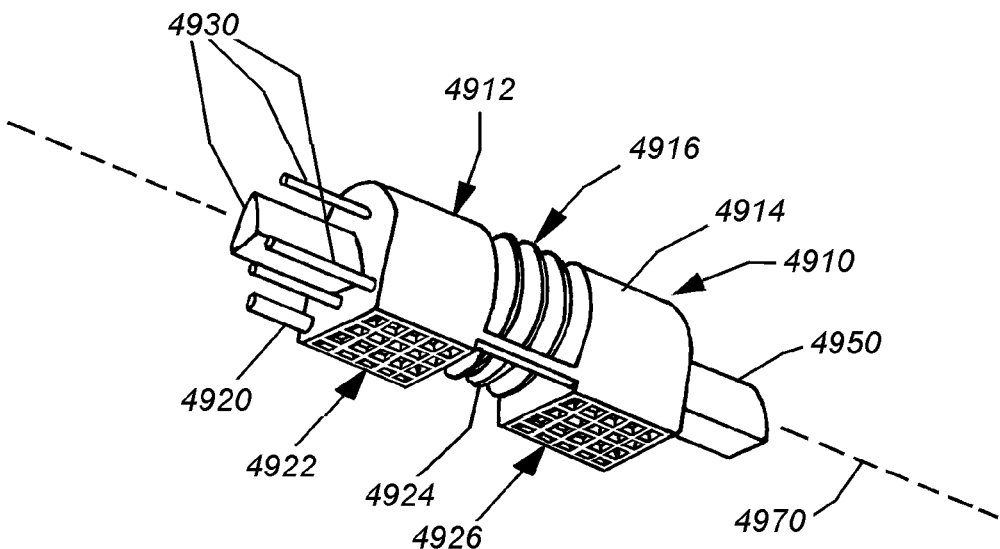
FIG. 49 is a bottom perspective view of an exemplary AGE showing basic steering and vacuum interconnections with respect to the proximal immobilizer and the distal immobilizer.

With brief reference to FIG. 49, a basic embodiment of an AGE 4910 is shown in bottom view for further reference steering mechanisms and other operative features. It includes a proximal immobilizer 4912, the distal immobilizer 4914 and a sealed bellows 4916 there between. The sealed bellows receives vacuum pressure through an appropriate conduit, or other lumen. One vacuum lumen 4920 communicates with the vacuum hold-down port arrangement 4922 for the proximal immobilizer 4912. An opposing lumen 4924 passes slidably through the proximal immobilizer 4912 and communicates with a grid 4926 in the distal immobilizer. Each lumen 4920 and 4924 can be separately depressurized and/or pressurized to provide vacuum selectively to either the proximal immobilizer 4912, the distal immobilizer 4914, or both.

A set of steering wires (also termed "cables") 4930 (three cables in this embodiment) are disposed around the central lumen that includes the ablation catheter 4950. The steering wires 4930 pass slidably through the proximal immobilizer 4912 and are anchored at an appropriate point in the distal immobilizer 4914. Selective tensioning of the wires 4970 allows the distal immobilizer 4914 to point itself of the central axis 4970 in three dimensions with respect to the proximal immobilizer. The wires 4930 are each located sufficiently remote from the central axis 4970 of the device so that applying tension to one or more, while releasing tension from others induces a rotational moment about a pivot area within the central region of the bellows 4916. In the embodiments described generally herein, the flexibility of the catheter comprises the "hinge" structure between the distal and proximal immobilizers. The catheter allows a gradual bend along the length between the immobilizers that enables multidirectional steering without binding or kinking the catheter. The degree of bending depends, in part, upon the amount of catheter length extending between the two immobilizers and the inherent bending characteristics of the catheter. This moment causes the distal immobilizer 4914 to deflect angularly with respect to the proximal immobilizer 4912. The wires 4930 can be constructed from any strong, relative small-gauge material, including a variety of monofilament and/or braided polymers and metals.

The immobilizer in the above-described AGE 4910 uses a basic grid pattern to transmit vacuum. One advantage of a grid pattern is that it prevents excess tissue from being drawn into the vacuum chamber, which might serve to block the vacuum port and prevent effective hold-down. A possible disadvantage to a grid, on curved or bumpy tissue, is that not all grid holes may be fully covered, allowing vacuum leakage and inadvertent release of the immobilizer.

VI. Immobilization

Figure 50:
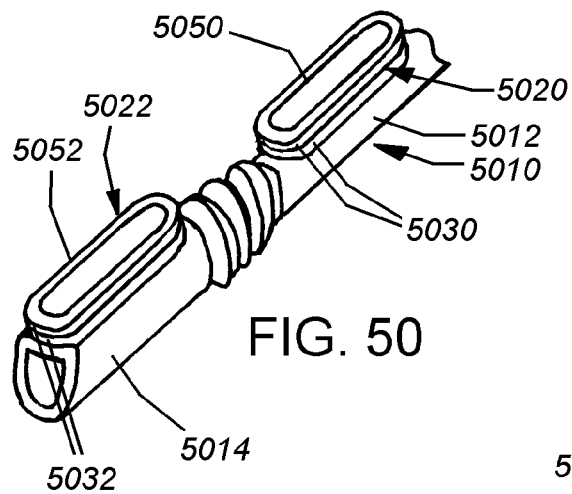
FIG. 50 is a bottom perspective view of an exemplary AGE or AID having an enhanced suction pad on each immobilizer for engaging rough or non-flat tissue according to an embodiment of this invention.
Figures 51, 52:
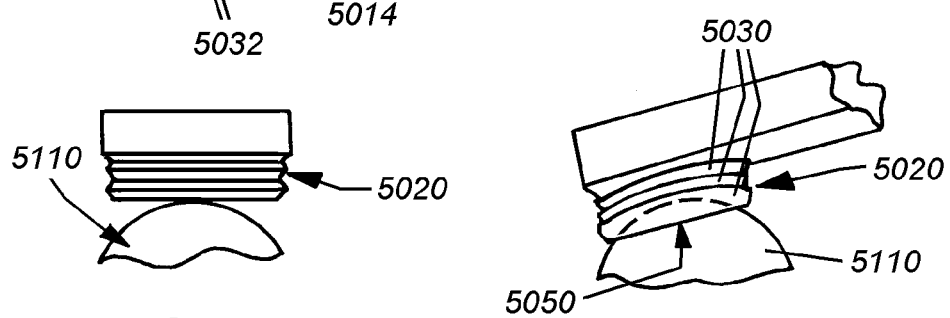
FIG. 51 is a partial side view of a suction cup of the AGE or AID of FIG. 50 approaching a non-flat tissue region.
FIG. 52 is a partial side view of the suction cup in engagement with the tissue shown in FIG. 51.

As described above, an immobilizer can be implemented in a variety of ways. FIGS. 50-52 detail an embodiment of a vacuum immobilizer arrangement that is particularly effective on highly curved surfaces. The exemplary AGE 5010 includes a proximal immobilizer 5012 and a distal immobilizer 5014 that are steered and/or actuated by any of the mechanisms described below. On the base of each immobilizer is a suction cup 5020 and 5022. Each suction cup comprises a plurality of respective accordion-like folds 5030 and 5032. These allow the respective suction cup to compress as appropriate. The suction cup can be formed by any acceptable, biocompatible flexible material that maintains a semi rigid structure. The contacting base 5050 and 5052 of each suction cup can comprise a differing material if desired. Such a material should have good sealing properties and remain pliable against rough surfaces. Medical silicone is one such material.

As shown in FIG. 51 an exemplary suction cup 5020 is applied against a relatively curved tissue surface 5110. The suction cup 5020 is then shown engaging the surface 5110 in FIG. 52. The base area 5050 of the suction cup conforms to the shape of the tissue due to differential flexure of the accordion folds 5030. The perimeter shape of the suction cup in this example is somewhat ovular. In alternate embodiments, the shape can be more square, circular or any other desired shape.

Figure 53:
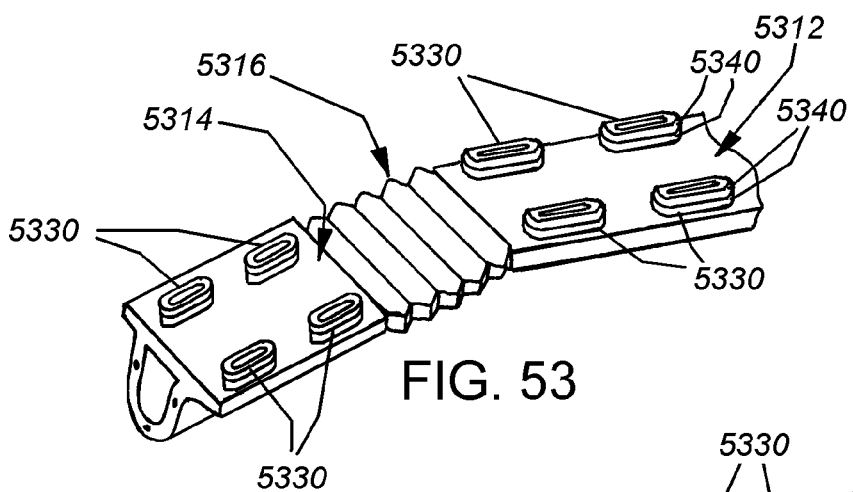
FIG. 53 is a bottom perspective view of an AGE or AID having a plurality of enhanced suction pads on each immobilizer.
Figure 54:
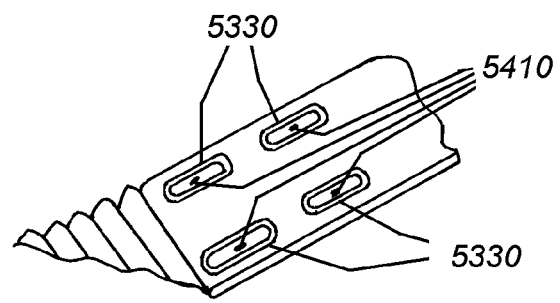
FIG. 54 is another view of the AGE or AID of FIG. 53, showing the suction ports for each pad.

FIGS. 53 and 54 detail an alternate arrangement for suction cups that are applicable to either an AID or an AGE embodiment. In this embodiment, a proximal immobilizer 5312 and a distal immobilizer 5314, joined by any conventional bellows-like or otherwise flexible central section 5316 each include a plurality of suction cups 5330. The suction cups each comprise smaller versions of the cups 5020 and 5022 described above. In this embodiment, they are ovular, but they can be any acceptable shape. They include a plurality of folds 5340 that allow the cups to comply with the surface texture and shape of the underlying tissue. As shown more clearly in FIG. 54, each cup includes at least one vacuum port 5410 through which vacuum communicates with the individual cups. Appropriate lumens can be provided within the structure of the immobilizers 5312 and 5314 to communicate vacuum selectively to the proximal and distal immobilizers. The cups can be constructed from the same material as the underlying immobilizer, or can be a different material that is more suited to the pliability desired in a suction cup.

Figure 55:
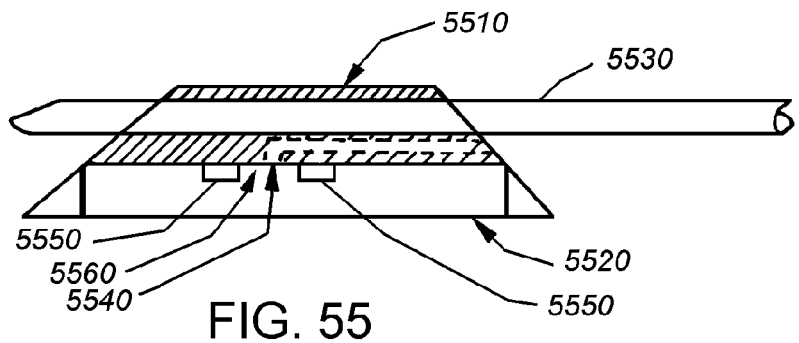
FIG. 55 is a side cross section of an immobilizer suction pad according to an embodiment of the invention including structures that avoid blockage of vacuum ports by tissue.
Figure 56:
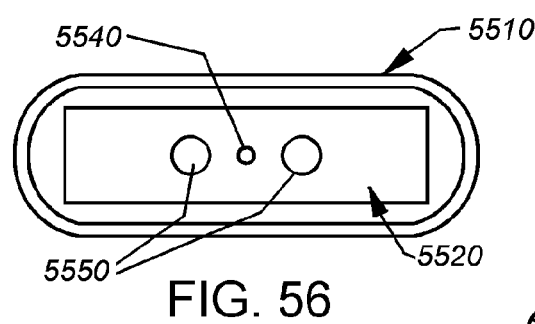
FIG. 56 is a bottom view of the immobilizer suction pad of FIG. 55.
Figure 57:
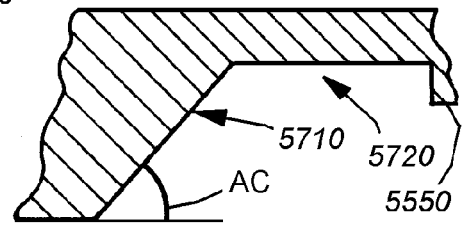
FIG. 57 is a partial side cross section illustrating an appropriate angle for the interior wall of the suction pad of FIG. 55.

As noted above, larger cups may tend to draw thereinto tissue that may serve to block a small vacuum port at the top of the cup. FIGS. 55-57 show a suction cup having an anti-vacuum choke (AVC) for that feature. The immobilizer 5510 includes an integral cup chamber 5520. The catheter 5530 passes through the immobilizer 5510. The large cavity of the cup may tend to draw a bolus of tissue thereinto. Since the vacuum port 5540 is relatively small, the tissue may easily block it if it is sufficiently soft and pliable. Accordingly, a pair of raised disks 5550, or similar projecting structures, are provided as an AVC mechanism. The disks 5550 are placed relatively close to the port 5540 so that any pliable tissue drawn up by the vacuum will come to rest on the disks 5550 and a gap region 5560 will remain between the disks or bosses 5550 with any tissue bridging that gap. This gap region is sufficient for vacuum draw to be maintained around the tissue and into the adjacent cup volume 5520.

As shown in FIG. 57, the angle of the inner wall 5710 of a cup interior 5720 can aid in the appropriate delivery of suction and avoidance of an undesirable bolus. Also the larger the angle of this wall, the greater lateral resistance to movement and slippage, which is more critical in some procedures such as an ablation. In this embodiment, the angle AC, combined with an AVC structure 5550, together assist in avoiding blockage of the port and cup interior by draw-in tissue. Hence, a proper vacuum can be maintained. The angle AC is between approximately 40 degrees and 90 degrees in various embodiments. However, the precise angle can be determined by applying the cup to tissue similar to that expected to be encountered within the body. Often the tissue of a pig's heart or other organ is a suitable model for human tissue of the same type.

In another embodiment, not shown, the AVC feature is a fine material mesh, generally the same size as the open face of the vacuum indent space, which is away from the roof wall of the cup in roughly the same location as the projections 5550 above, to allow the vacuum to reach all parts of the vacuum indent space. The mesh forms the front surface of a thin vacuum distribution chamber and the tissue is drawn tightly against the mesh instead of against the cup roof wall, thereby allowing for a vacuum gap.

Figure 58:
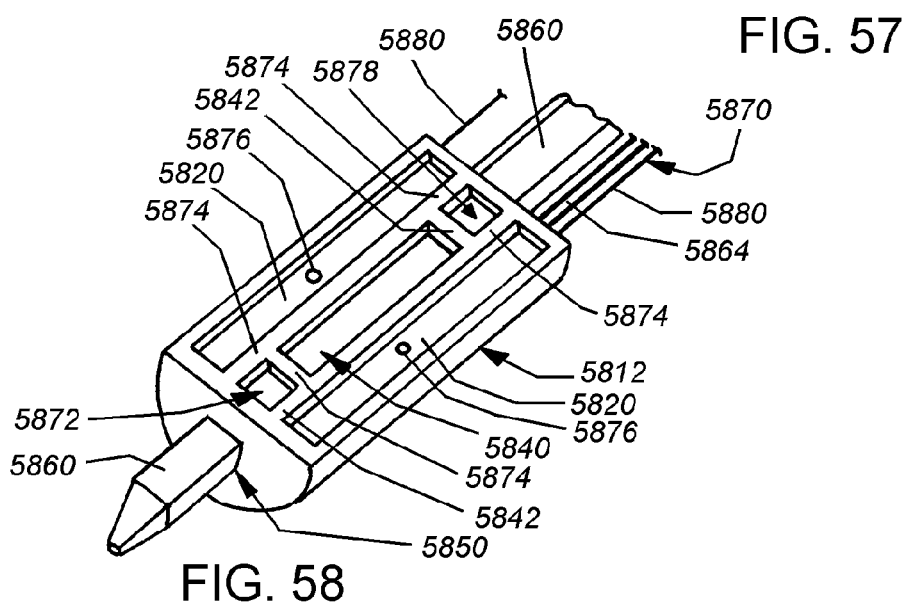
FIG. 58 is a bottom perspective view of an immobilizer for an AGE or AID having an exposed central region.

Another embodiment of an immobilizer vacuum base structure is shown for the exemplary distal immobilizer 5812 of FIG. 58. In this embodiment, an elongated vacuum channel 5820 is provided near the outer edges of the immobilizer 5812. A central region 5840, broken only by small ribs 5842 (for structural integrity and stiffness) is provided beneath the catheter lumen 5850. In this manner, the catheter 5860 is free to emit its ablation energy (or other therapeutic properties) through the open space 5840 while substantial area for applying vacuum is afforded by the channels 5820. The channels are fed by a vacuum lumen 5864 that passes through the central region 5870 proximally of the immobilizer 5812. A respective pair of central vacuum chambers 5872 and 5878, located distally and proximally of the central open space 5840 provide additional, centralized hold-down force in this embodiment. The central vacuum chambers 5872, 5878 communicate through ports or passages (not shown) in the ribs 5874 located between the chambers 5872, 5878 and the side vacuum channels 5820. The channels are served by vacuum ports 5876 that communicate with the vacuum lumen 5864. Appropriate steering cables 5880 or other actuation/steering mechanism can also be provided to interconnect with the proximal immobilizer (not shown). The proximal immobilizer can employ the same, or a similar, base structure as that depicted in FIG. 58.

FIGS. 59-62 detail an alternate embodiment of an immobilizer that does not employ vacuum pressure to secure itself to tissue. It is recognized that small biocompatible needles and/or microneedles can be used to secure materials to pericardial tissue and other forms of body tissue without incurring pain or irreparable damage. Such microneedles can be constructed from biocompatible polymers, metals or ceramic materials. The micro needle material, for example, can be a standard biodegradable material or a biodegradable polymer, such as Polylactic Acid (PLA), Polyglycolic Acid (PGA) or others that may exhibit conductivity, which is useful as an electrical sensor in determining the effectiveness of the ablation.

Figure 59:
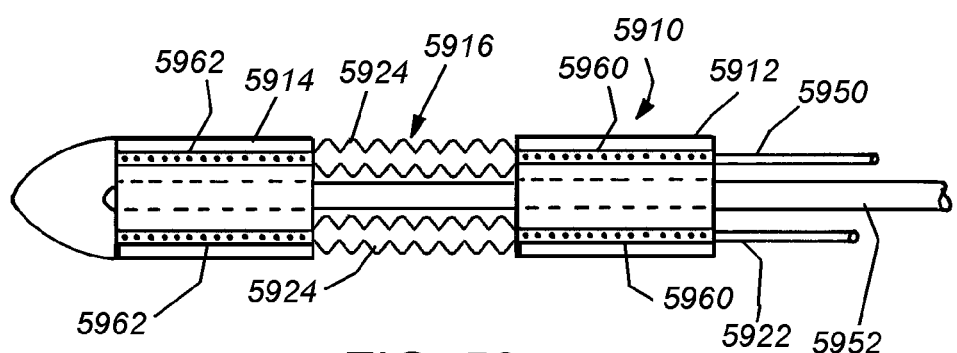
FIG. 59 is an exposed bottom view of an AGE employing an array of deployable needles and/or microneedles as an immobilization mechanism according to an embodiment of the invention.
Figure 60:
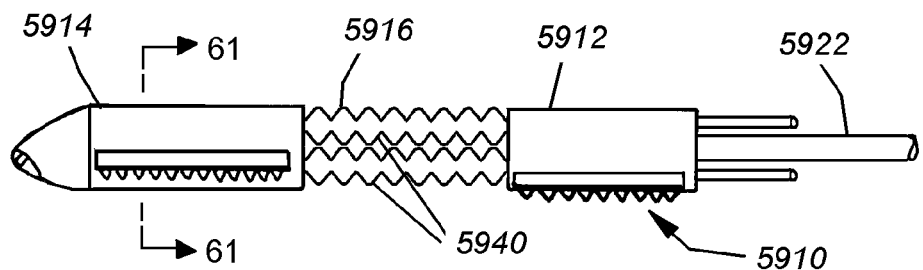
FIG. 60 is an exposed side view of the AGE of FIG. 59.

As shown in FIG. 59, an AGE 5910 of this embodiment includes a proximal immobilizer 5912 and a distal immobilizer 5914. A catheter 5922 runs through the center of both immobilizers 5912 and 5914 and also through a bellows region 5916 that provides appropriate steering and/or actuation to the distal immobilizer 5914. Such steering and actuation can be in accordance with any mechanism described above. In this particular embodiment, the actuation is by means of two or more bellows 5924, which can each expand and contract individually. A pair of pressure lines 5950 and 5952 extend, respectively, to each of the proximal immobilizer 5912 and distal immobilizer 5914.

Figure 61:
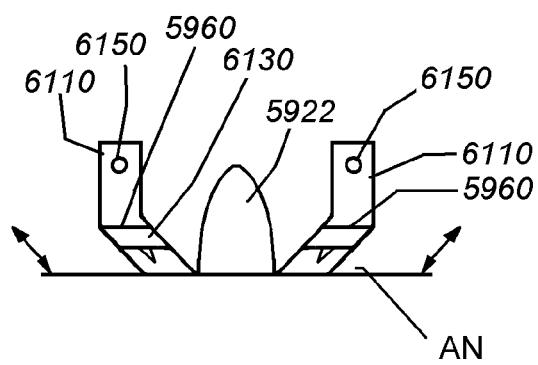
FIG. 61 is a partial front cross section of the needle deployment mechanism taken along line 61-61 of FIG. 60 showing the needles retracted.
Figure 62:
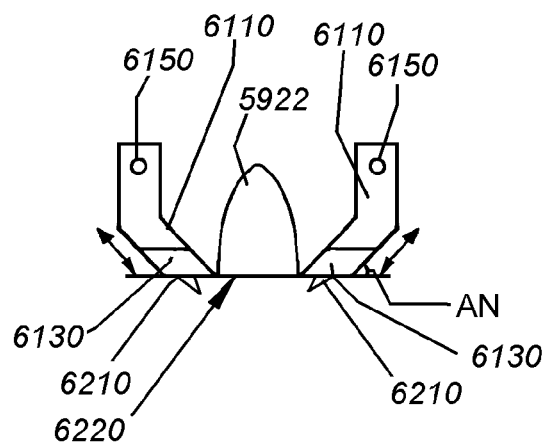
FIG. 62 is the partial side cross section shown in FIG. 61 with the needles deployed.

Referring further to FIGS. 61 and 62, within each immobilizer 5912, 5914 is provided pairs of microneedle assemblies 5960 and 5962. When the pressure in either line 5950 or 5952 is applied, the respective microneedle assembly 5960 and 5962 moves within a respective guideway 6110 from a refracted position as shown in FIG. 61 to an extended position as shown in FIG. 62. In the extended position, the individual needles 6210 extend outwardly beyond the plane of the base surface 6220 of the immobilizer so that they engage the underlying tissue at an acute angle AN. In this manner, upon needle deployment/extension the immobilizer becomes essentially pinned to the tissue by large number of small needles. The number of needles on an assembly can vary both in the lengthwise direction and in widthwise direction depending on the size/diameter of the individual needles and the size of the needle assembly base 6130. The needle assembly base 6130 can include appropriate seals or other structure that maintain a pressure seal between it and the guideway 6110. In this manner, the needle assembly is extended by pressurizing the guideway and the needle assembly is retracted by inducing a vacuum in the guideway. Appropriate seals between the needle assemblies and the guideway prevent excessive pressure loss. To provide pressure/vacuum, each guideway 6110 can include appropriate ports 6150 in communication with a corresponding pressure lumen 5950 or 5952.

In an alternate embodiment, a push-pull linkage can be employed, acting on each assembly of needles in communication with an externally driven linkage. Likewise, electromagnetic energy could be used in, or along the guideway 6110 to actuate each array, which includes a magnetically attracted base. In this manner, the needle bases act like solenoids responding to the force of an energized coil.

Figure 63:
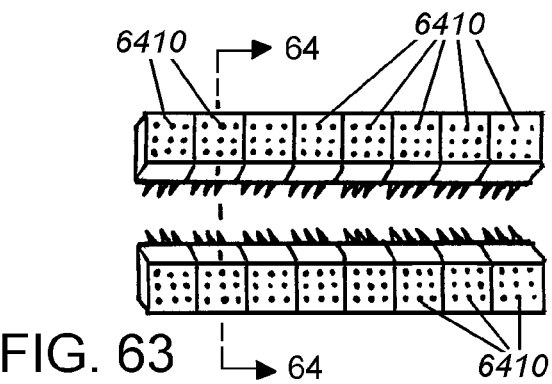
FIG. 63 is a somewhat schematic top view of an array of individually movable needle sets for use on the bottom of an immobilizer according to an embodiment of the invention.
Figure 64:
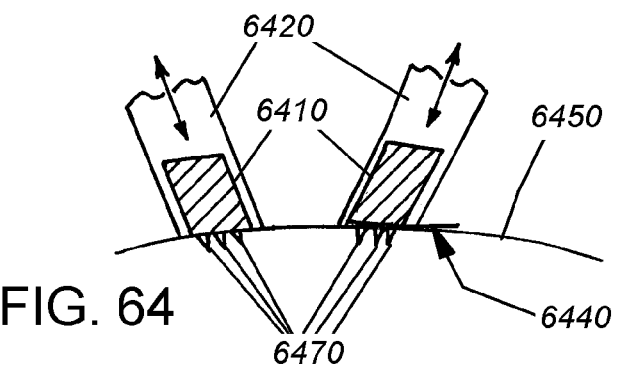
FIG. 64 is a front cross section of the array taken along line 64-64 of FIG. 63 in engagement with a curving tissue surface.
Figure 65:
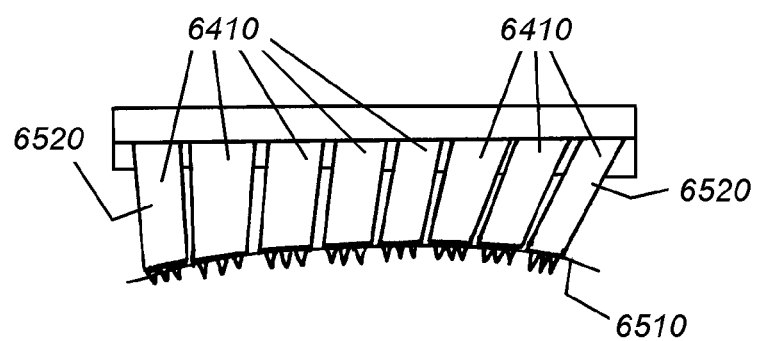
FIG. 65 is a side view of the array of FIG. 63 in engagement with the curving tissue surface and detailing variable deployment of the needle sets to conform to the curve.

With reference to FIGS. 63-65 an alternate embodiment of a needle-based hold-down mechanism is shown. As noted above under certain conditions, the underlying tissue surface may be irregularly shaped or rounded. Accordingly, a hold-down assembly can be constructed with a plurality of individual needle bases 6410 that are laid out in a longitudinal direction (axially with respect to the direction of extension of the AGE). Each needle base 6410 can slide upwardly and downwardly separately with respect to adjacent needle bases. In one embodiment all the needle bases reside in a common guide way 6420, which is in communication with the pressure/vacuum source. The needle sets are collectively sealed against air leakage and allowed to independently slide along the guideway. In one embodiment, the needle sets can be covered by a highly flexible sealing membrane that, when inflated causes the needle sets to extend out of the base but prevents loss of pressure from the upper region of the guideway adjacent to the port. In another embodiment the bases have a circular shape and are each placed sealingly in a separate cylinder this selectively filled with pressure/vacuum from a common source lumen to resultantly extend retract each of the bases to a predetermined distance.

When extended, all needle bases 6410 are driven to extend out of the plane base surface 6440 of the immobilizer and into the tissue surface 6450. Notably, as shown in FIG. 65, because the bases 6410 are independently moveable to varying distances, the application of pressure will allow certain needle bases to extend further out (within predetermined limits that may be set by a stop) than other adjacent bases. Hence, as shown in FIG. 65, a tissue surface 6510 that is longitudinally curved can be fully engaged. To this end, the outermost bases 6520 have extended further downwardly than the innermost bases 6540 to conform to the downwardly sloping curve of the tissue surface 6510. The extension pressure should be chosen so that it allows differential extension of different needle sets without forcing all needle sets to extend to a maximum distance. This ensures that the unit will gently conform to the shape of the tissue without applying excessive force to it. As shown in this embodiment, a plurality of needles have been laid across both the lengthwise (longitudinal) and the widthwise directions of each set. The precise number of needles, the shape of each set base, the size of individual needles and other parameters are highly variable.

Note that in each of the above-described micro needle embodiments, one advantage is that the needles may be electrically interconnected with leads that extend back to the control system. In this manner, the needles can be used to apply energy or measure temperature or other characteristics of the tissue. This may help to determine the efficiency of the ablation process or to perform other diagnostic functions. In addition, the needles may include microscopic lumens through which medicines and other fluids can be applied to the surface. In any of the embodiments above, it is expressly contemplated that fluid conduits that provide cooling fluid or other desired gases or liquids can be included in the distal and/or proximal immobilizers or in any appropriate AID structure.

Figure 66:
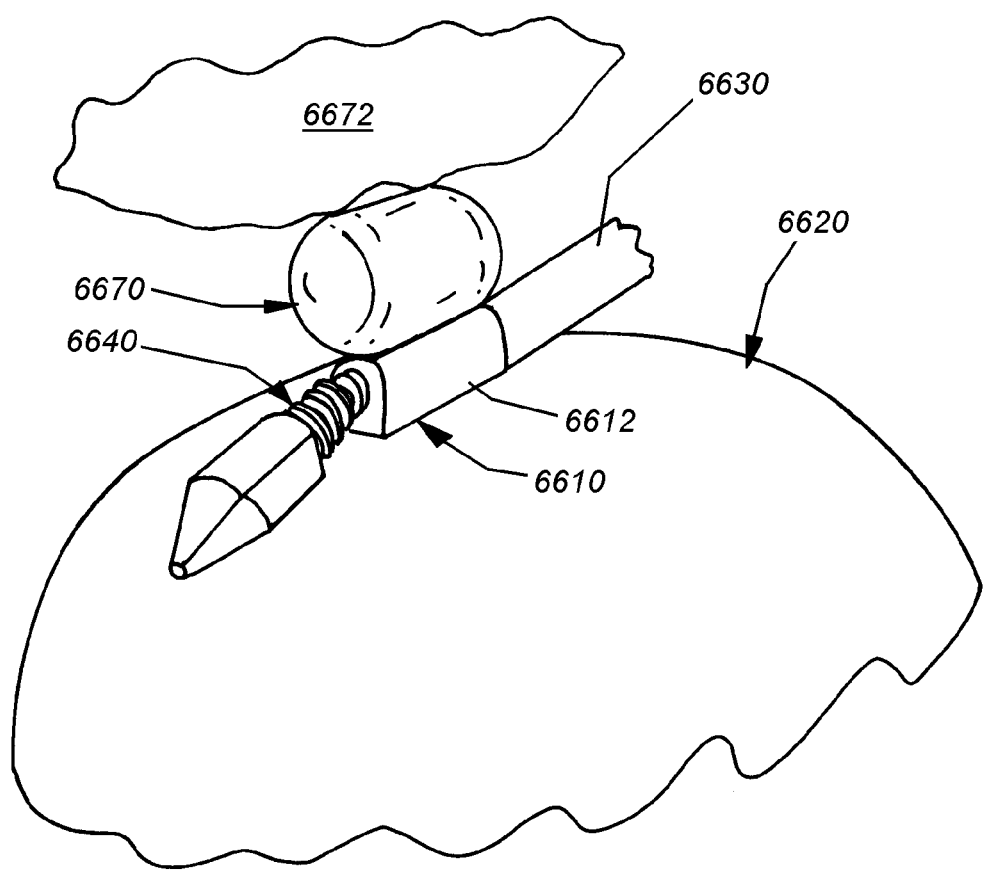
FIG. 66 is a somewhat schematic perspective view of an inflatable bladder on the exterior of the AGE, acting as a hold-down mechanism when bearing against an adjacent tissue surface, according to an embodiment of the invention.

Another embodiment of an inventive hold-down mechanism is shown in FIG. 66. In this embodiment, an AGE 6610 similar to the type shown in FIGS. 29 and 30 (although any AGE or AID can be employed herewith) is applied to the heart 6620. The proximal cannula 6630 extends back out of the body to the control system. The AGE includes any desired steering and/or actuation mechanism such as the helical drive 6640 shown herein. On the top side of the proximal immobilizer 6612 is provided an inflatable balloon 6670. A similar balloon can be provided on the distal immobilizer if desired. Pressure send through the cannula 6630 causes the balloon to inflate when desired. Since the heart is in close proximity to other organs or tissue 6672 within the body cavity, it is contemplated that inflation of the balloon 6670 will bring it into engagement with the tissue or organ 6672 as shown. This assists in holding down the immobilizer against underlying tissue, and may avoid the need for internal vacuum chambers, microneedles and/or other hold-down mechanisms that must engage the underlying tissue (and may block access to the catheter). Additionally, by creating and maintaining a space between the target tissue, such as the heart, and surrounding organs during ablation, the chance of injuring surrounding regions are minimized. Alternatively, this balloon 6670 can be used to supplement such mechanisms where desired.

VII. AGE Control System

Figure 67:
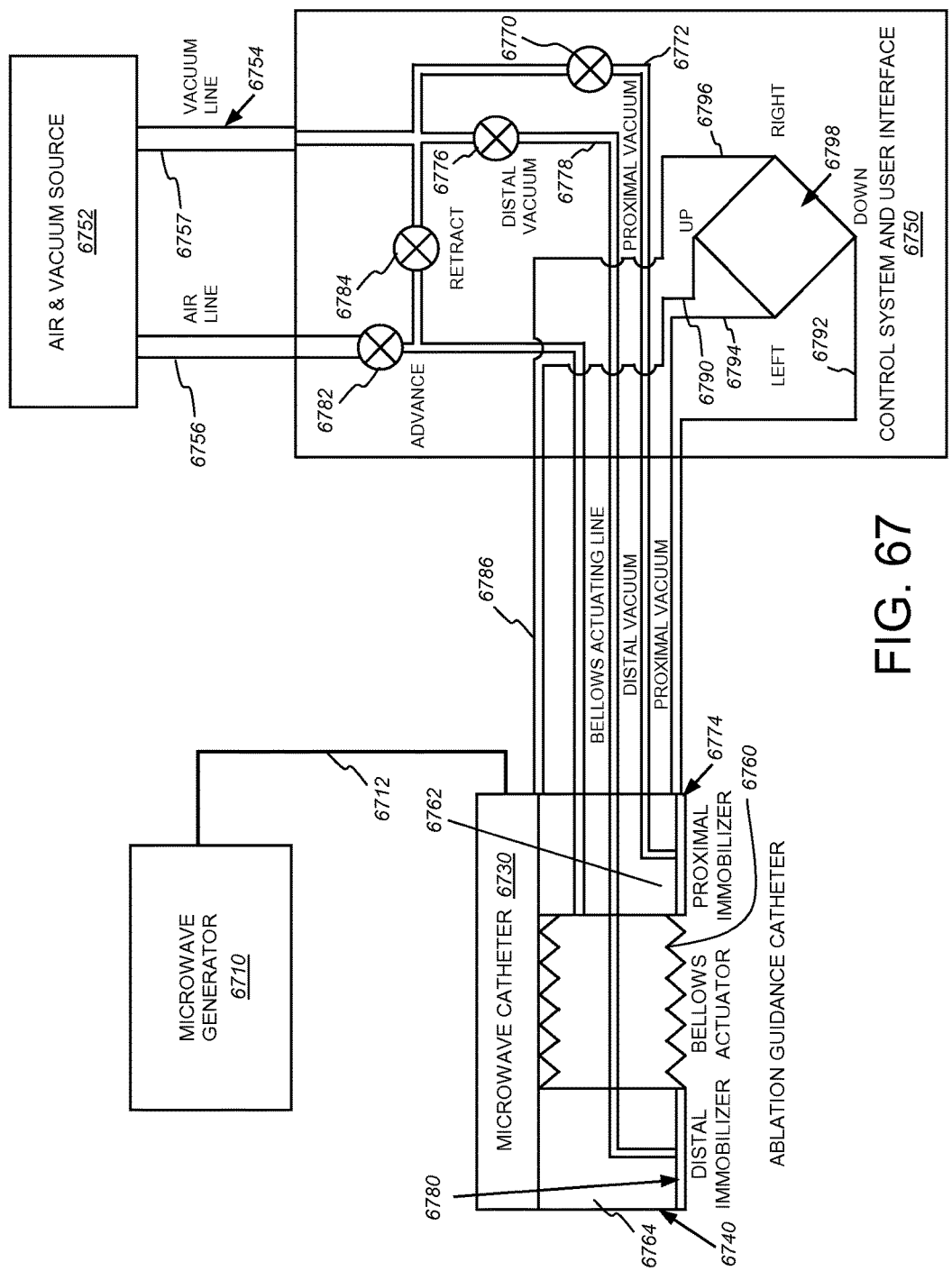
FIG. 67 is a generalized schematic diagram of a guidance system for tan AGE employing a combined bellows actuating and mechanical wire-steering arrangement according to an embodiment of the invention.
Figure 68:
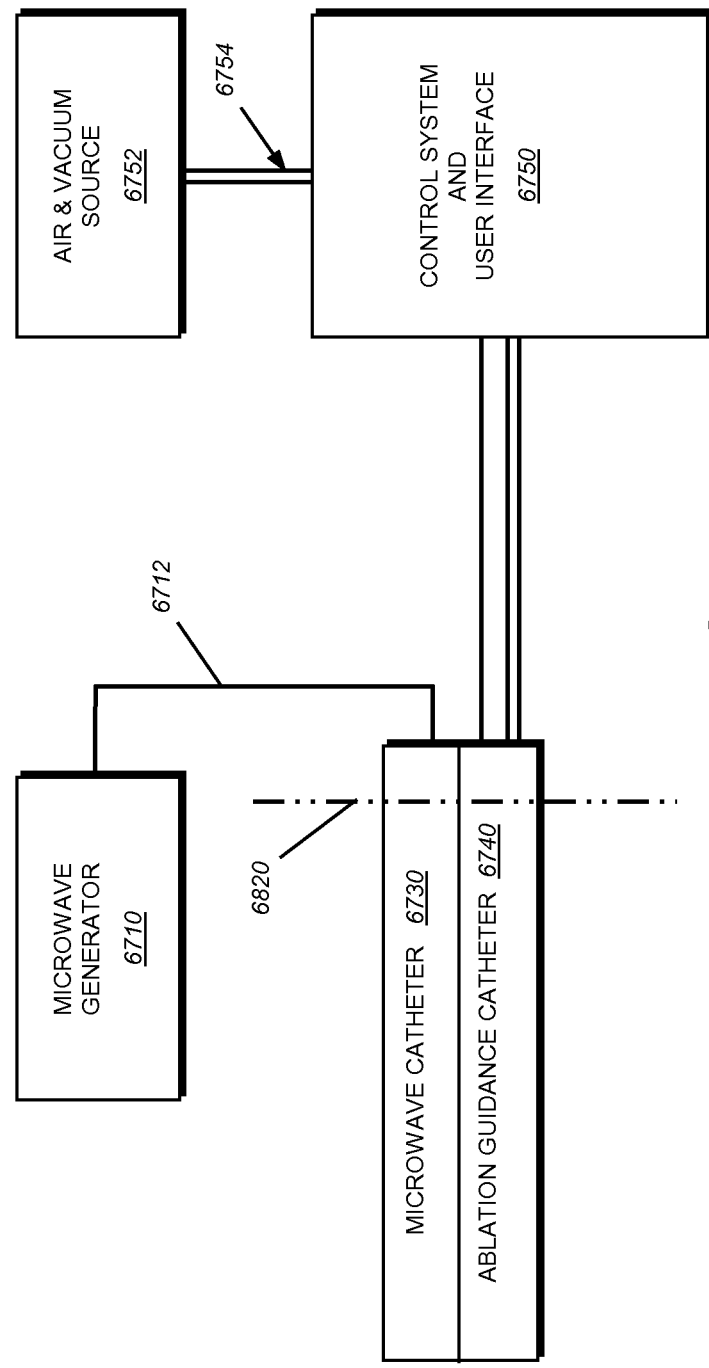
FIG. 68 is a block diagram of the primary system components with respect to the guidance system of FIG. 67.

Reference is now made to FIG. 67 that shows an overview of the control system for an exemplary implementation of the AGE according to an embodiment of this invention. Reference is also made to the more generalized block diagram of more generalized control system functions shown in FIG. 68. In each diagram a microwave generator 6610 is shown. The generator is used to transmit the desired level of microwave energy to the above-described ablation catheter. Note that other forms of ablation can be employed according to this invention. Such forms of ablation include regular and light-based catheters, those that use electrical contact to cauterize tissue and cryogenic fluid-delivery systems. An appropriate energy/fluid generator for such types of catheters could be substituted for the microwave generator 6710. In this embodiment, the microwave generator transmits energy through a line 6712 contained within the cannula of the catheter. The catheter extends through the body interface 6820 (FIG. 68), namely skin and muscle layers covering the thoracic cavity, and into the interior of the body where the operative end of the exemplary microwave catheter 6730 resides during the procedure.

The microwave catheter 6730 is carried by the ablation guidance enhancer (the AGE 6740) in this embodiment. The AGE. 6740 is controlled by a control system and user interface 6750 that receives air and vacuum from a source 6752 via the line assembly 6754. This line assembly includes, typically, a separate air line 6756 and vacuum line 6757 routed from appropriate pumps within the source 6752. Within the control system is contained a set of valves that control the hold-down function as well as (in this embodiment) the actuation function which is carried out by a bellows actuator 6760 located between the proximal immobilizer 6762 and the distal immobilizer 6764. As shown, a proximal vacuum valve 6770 controls the hold-down of the proximal immobilizer via a proximal vacuum line 6772. When this valve is opened, vacuum is applied to the proximal immobilizers vacuum chamber 6774. A distal vacuum valve 6776, also in communication with the main vacuum line 6757, can be opened to provide a vacuum to the distal immobilizer's vacuum line 6778. When opened, the distal immobilizer's vacuum chamber 6780 is placed under vacuum pressure allowing it to act as a hold-down.

The user coordinates (or a computer/processor automatically coordinates) the actuator's (6760) advance and retract valves. The advance valve 6782 and retract valve 6784 are each in communication with a separate line source 6756 and 6757. They both communicate with the bellows actuating line 6786. When the retract valve 6784 is opened, the vacuum source is connected with the bellows line 6786, allowing vacuum to draw the bellows together. Typically this occurs while the distal immobilizer is held down and the proximal immobilizer is released, thereby allowing the proximal immobilizer to crawl forward. Conversely, when the proximal immobilizer is held down, and the distal immobilizer is released, the retract valve 6784 is closed and the advance valve 6782 is opened, allowing a predetermined amount of air pressure to enter the bellows 6760. Once the bellows is fully extended the distal immobilizer is again held down. While not shown, either within the vacuum source, or along each line, is provided appropriate pressure release and pressure monitors that prevent excessive buildup or either pressure or vacuum. Such buildup could cause failure in the device due to overstressing.

In this embodiment, a wire or cable-type steering arrangement is provided. Four cables located in quadrants around the AGE 6740 are employed. The cables are typically placed under moderate tension along the entire length of the cannula run to avoid play in the steering due to slackness. Automatic slack-removal devices, such as spring assemblies or electromechanical actuators (not shown) can be employed to maintain and regulate the desired level of tension. In this embodiment the four steering cables comprise an up cable 6790, a down cable 6792, a left cable 6794 and a right cable 6796. However, in some embodiments three cables oriented at approximately 120 degree angles to each other can also be employed with appropriate mixing of control functions. Within the center of the cable arrangement is an electromechanical or mechanical joystick 6798.

Figure 69:
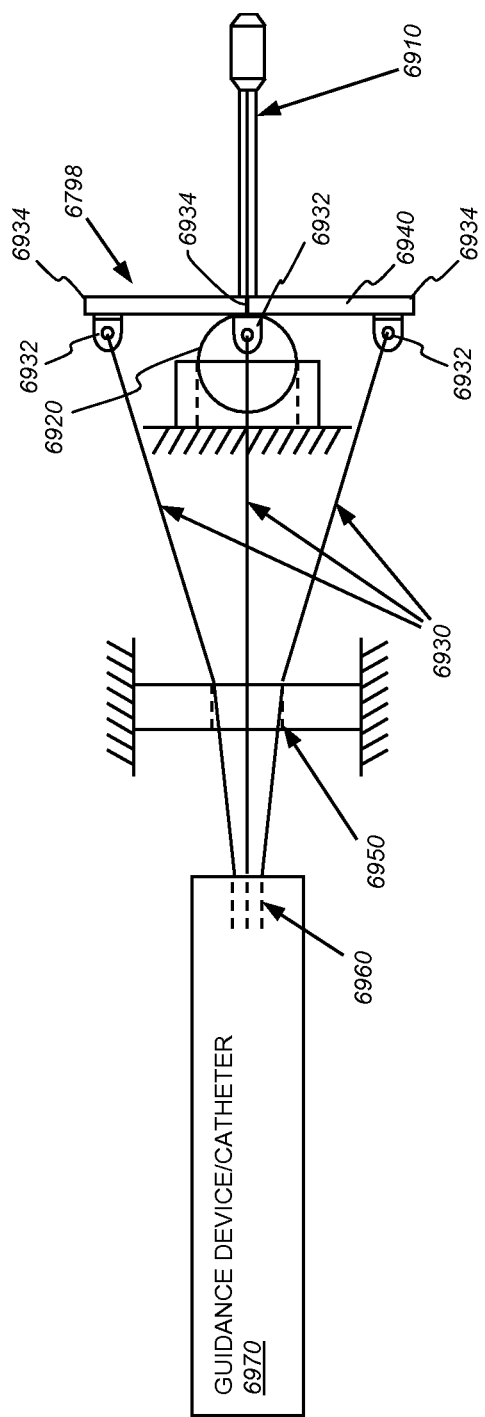
FIG. 69 is a somewhat schematic side view of a joystick-based steering control employed with respect to the guidance system of FIG. 67.

The joystick assembly is shown in further detail in FIG. 69 in accordance with one exemplary embodiment. The embodiment includes a control stick 6910 located on a ball mount, or other gimbal system 6920. The cables 6930 are each interconnected to bases 6932 at each of four corners 6934 (or other structures) on the joystick plate 6940. As shown the cables remain under tension and eventually neck down through a narrowed opening 6950 in the control unit to eventually comprise a tensioned cable run 6960 within the catheter assembly 6970. Tension can be maintained by ensuring that, at no point along their run, the cables are allowed to become loose. Appropriate adjustment screws, turnbuckles and other devices can be provided to the joystick assembly to ensure that the cables remain taut and properly adjusted for center.

Figure 70:
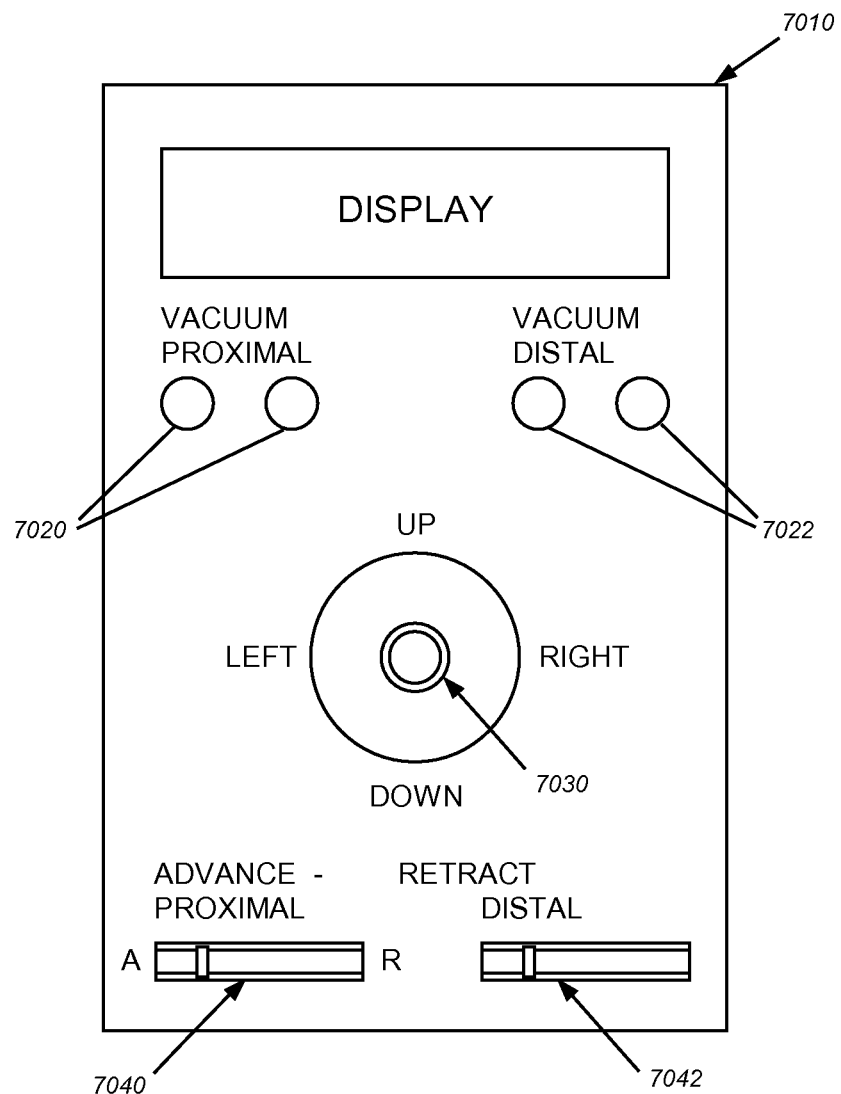
FIG. 70 is an exemplary control panel for a Human-Machine Interface (HMI) used in conjunction with the guidance system of FIG. 67.

FIG. 70 shows a schematicized example of a control panel 7010 that can be employed in connection with AGE and in accordance with this invention. A display 7012 provides status data and other information with respect to the operation of the AGE. For example, it can provide indicators as to which hold-down is currently operating and the steering direction in which the AGE has been placed. Buttons 7020 the vacuum hold-down function of the proximal immobilizer as shown, as well as buttons 7022 that control the vacuum hold-down function of the distal immobilizer. A joystick 7030 of a type described generally in FIG. 69 for mechanically controlling the steering cables is provided at the center of the panel 7010. Alternatively, the joystick 7030 can interface with various electromechanical, pneumatic, hydraulic or electromagnetic circuits so as to control AGEs that operate on such principals, in a manner described generally herein. A pair of slide switches 7040 and 7042 are used to advance or retract the actuator so that the immobilizer moves in a proximal direction (switch 7040) or a distal direction (switch 7042).

It should be clear that the control panel described herein is only exemplary, and that various hardware and software components can be used to coordinate movements of components. Likewise, the control mechanism shown herein can be provided on a computer screen, such as that available in a laptop and/or desktop PC configuration. Appropriate interfaces can be provided between the computer and its control software and the underlying mechanical components that operate the catheter. In this manner, movement of the catheter can be fully automated and largely under the control of the computer. In one example, when the user instructs the AGE to move forward by a certain amount, the computer automatically activates the hold-down vacuum in one immobilizer, advances the other immobilizer, and then activates the hold-down vacuum in the advanced immobilizer. When the user instructs a turn, the computer automatically applies an appropriate amount of steering in the desired direction to the cables or other steering devices. Electrodes within the AGE's base can indicate when a maneuver has been completed correctly.

Figure 71:
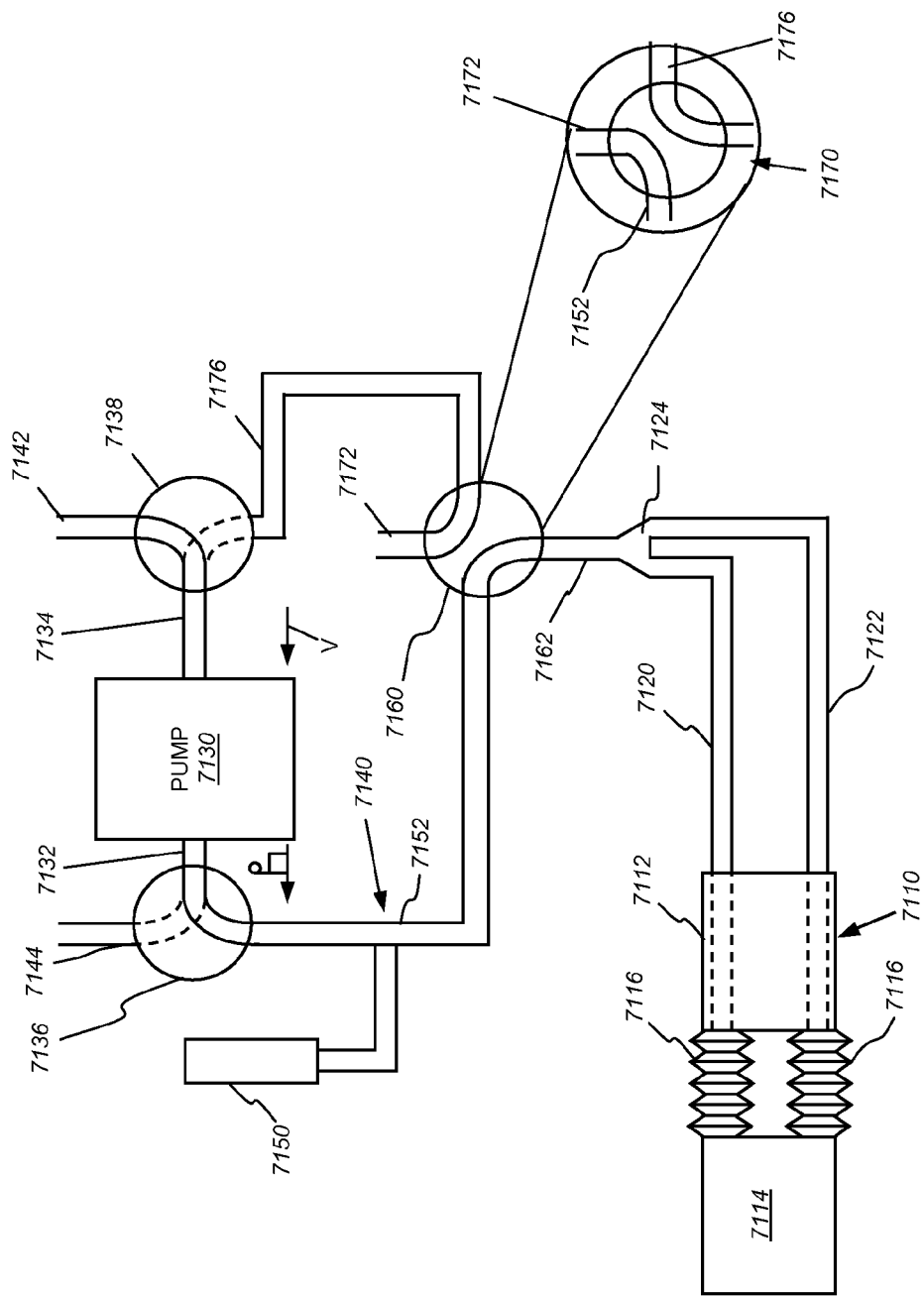
FIG. 71 is a more detailed schematic view of a pneumatic or hydraulic actuator control for use with the guidance system of FIG. 67.

Reference is now made to FIG. 71, which shows an embodiment of a pressure circuit used in connection with a bellows-based actuation (and steering) system for an AGE 7110. The AGE 7110 includes proximal immobilizer 7112 and a distal immobilizer 7114. These immobilizers 7112, 7114 are joined by two or more discrete bellows 7116 each communicating with its own pressure lumen 7120 and 7122. In this embodiment, both lumens 7120, 7122 are joined to a common pressure feed lumen at a Y-connection 7124. However, the in another embodiment, two or more circuits of the type described in FIG. 71 can be employed together to control each respective bellows separately so as to provide steering control as well as actuation.

A pump 7130 is provided in the system. This pump delivers both pressure (arrow P) and vacuum (arrow V) simultaneously through opposite outlets 7132 and 7134, respectively. Alternatively separate pressure and vacuum pumps can be provided at each outlet. In the depicted embodiment, each outlet 7132 and 7134 contains an appropriate two-way valve 7136 and 7138, respectively. Either valve is closed when desired to place either pressure or vacuum into a pressure control circuit 7140. When a valve 7136, 7138 is open, it vents to the atmosphere via an associated vent 7142 (for vacuum) and 7144 (for pressure). Only one valve 7136, 7138 is closed into the circuit 7140 at a time. In this example, the pressure valve 7136 is closed while the vacuum valve 7138 vents to atmosphere. A pressure regulator 7150 is provided along the pressure line 7152 of the circuit to avoid overpressure within the system. A two-way valve 7160 is provided at the feed line 7162 to the two lumens 7120 and 7122. As shown, the valve 7160 is arranged so that the pressure line 7152 is in communication with the lumens 7120 and 7122. In the depicted circuit 7140, the bellows are pressurized. In an alternate position shown in the circle 7170, the valve 7160 is rotated so that the pressure line is vented to atmosphere via the vent 7172. The lead 7162 to the lumens 7120 and 7122 is placed in communication with the vacuum line 7176 of the circuit 7140. In order to deliver a vacuum, the outlet valve 7138 adjacent the pump 7130 is rotated so that the vacuum outlet 7134 is placed in communication with the vacuum line 7176. In that orientation, the lumens receive vacuum and the bellows contract.

By maintaining the valves in the appropriate positions, a continuously operating pump can deliver pressure, vacuum or neither to the bellows as desired. It should be clear but by simply duplicating the circuit 7140 and associated valves, that a plurality of bellows can be operated independently at each lumen. This alternate arrangement is expressly contemplated to provide steering as well as actuation. As described above, while AIDs are not capable of independent movement, they can be steered to place them into a desired position, once directed to an approximate location on the tissue.

VIII. Improved AID Structures

Figure 72:
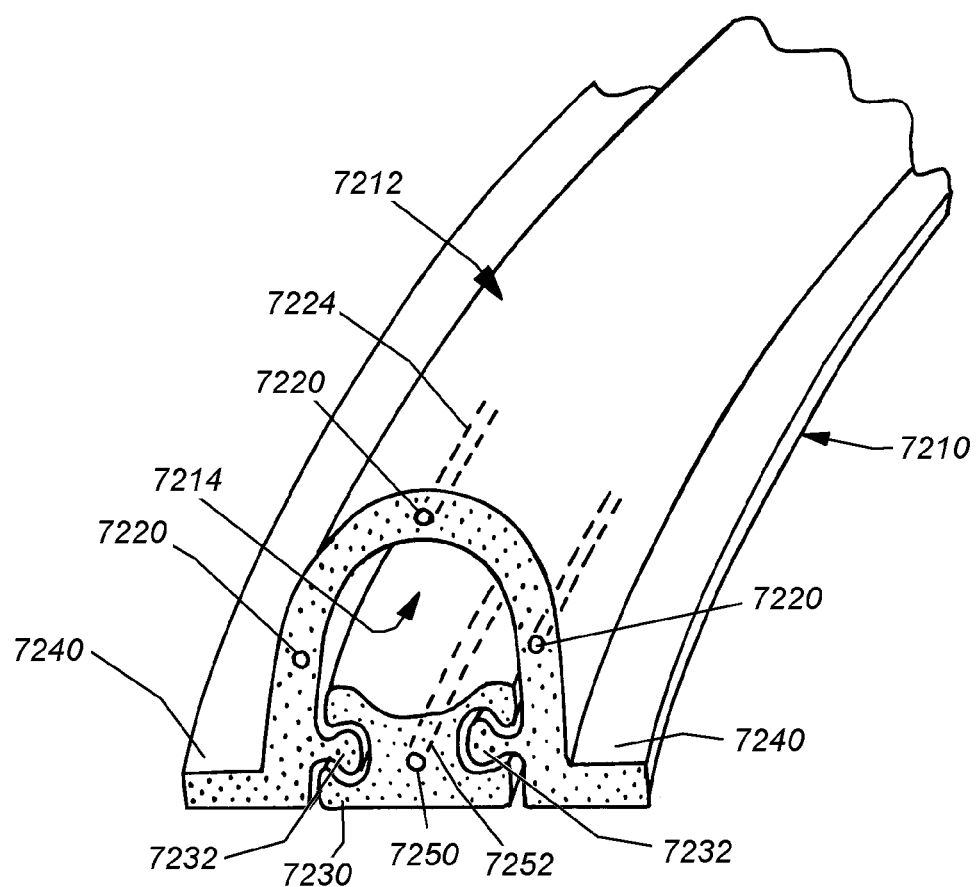
FIG. 72 is a perspective cross section of an immobilizer section of an AGE or AID including a movable floor that allows the inner lumen to become exposed.

As shown in FIG. 72, a moving-floor embodiment of an AID (or AGE) 7210 includes an outer omega-shaped/arched body 7212 with a lumen 7214 for receiving a catheter. The arch-shaped upper structure of the AID includes three cable anchors 7220 for steering cables that extend through associated lumens 7224 (shown in phantom) within the structure of the AID body 7212. A sliding floor 7230 is provided at the base of the lumen 7214. The sliding floor rides on ribs 7232, which are keyed so the Omega arched structure 7212 cannot separate and dislodge the floor 7230, face each other near the base (suction base) 7240 of the AID 7210. In order to affect better steering, the base also includes a steering cable anchor 7250. An associated steering cable (lumen 7252 shown in phantom) extends back through the floor. The steering cable exerts tension on the floor when steered. As the floor is pulled away, the table is drawn out with it as steering is no longer needed while the AID is immobilized. By sliding away the floor it is allows the bottom of the lumen to be exposed to the tissue so the catheter can be more closely brought into proximity with the tissue. In an alternate embodiment, an internal catheter lumen-mounted hold-down balloon or bladder can be provided—such as the balloon (1670) shown and described with reference to FIGS. 16 and 17.

Figure 73:
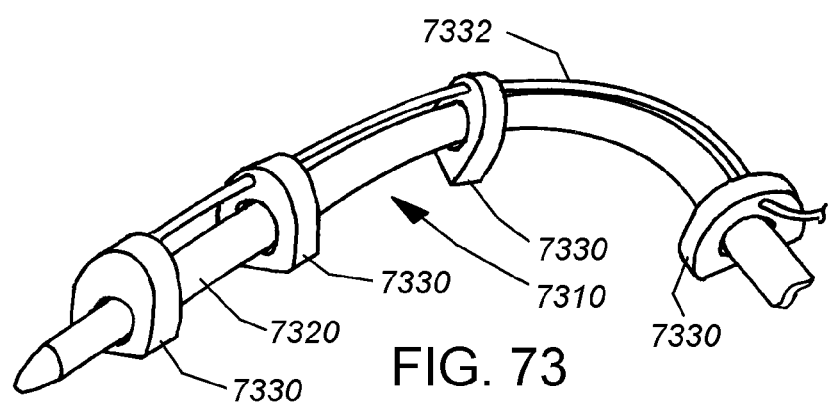
FIG. 73 is a top perspective view of an AID according to an alternate embodiment, featuring independent immobilization segments disposed along an exposed catheter.
Figure 74:
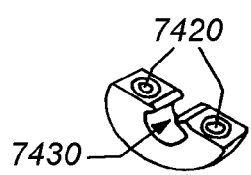
FIG. 74 is a bottom perspective view an exemplary immobilization segment of the AID of FIG. 73.

Reference is now made to another embodiment of an AID 7310 shown in FIGS. 73 and 74. The AID encases a therapeutic (typically microwave-ablation) catheter 7320, and includes a series of open hold-down segments 7330 that are separated by a predetermined distance, and are each connected by a portion of a vacuum line 7332. The vacuum line 7332 places each segment 7330 into communication with the vacuum source, and also into communication with a more distal vacuum-line segment that transmits the vacuum along the segment line (except for the most-distal segment, which is sealed at the end). The spacing between segments 7330 is highly variable. While not shown, independent steering cables can be provided between cables to steer the unit. Alternatively, it can be steered into position using a steerable guide catheter that has been removed, allowing the segments to be held in place by vacuum. Alternate hold-down mechanisms as described above, such as the needles/microneedles or the compressing balloon can also be used with, or instead, of vacuum.

As shown further in FIG. 74, a pair of vacuum ports 7420 are provided on the base of each segment near the respective outer edges thereof. The lumen 7430 is opened, defining a somewhat horseshoe-shape in each of the segments 7330. This relatively open base allows the full area of the catheter to be exposed to the underlying tissue. Each segment's vacuum ports 7420 can be constructed in a variety of ways. They can be constructed as a plurality of small ports, suction cups, or any of the other types of vacuum immobilizer base structures described herein.

Figure 75:
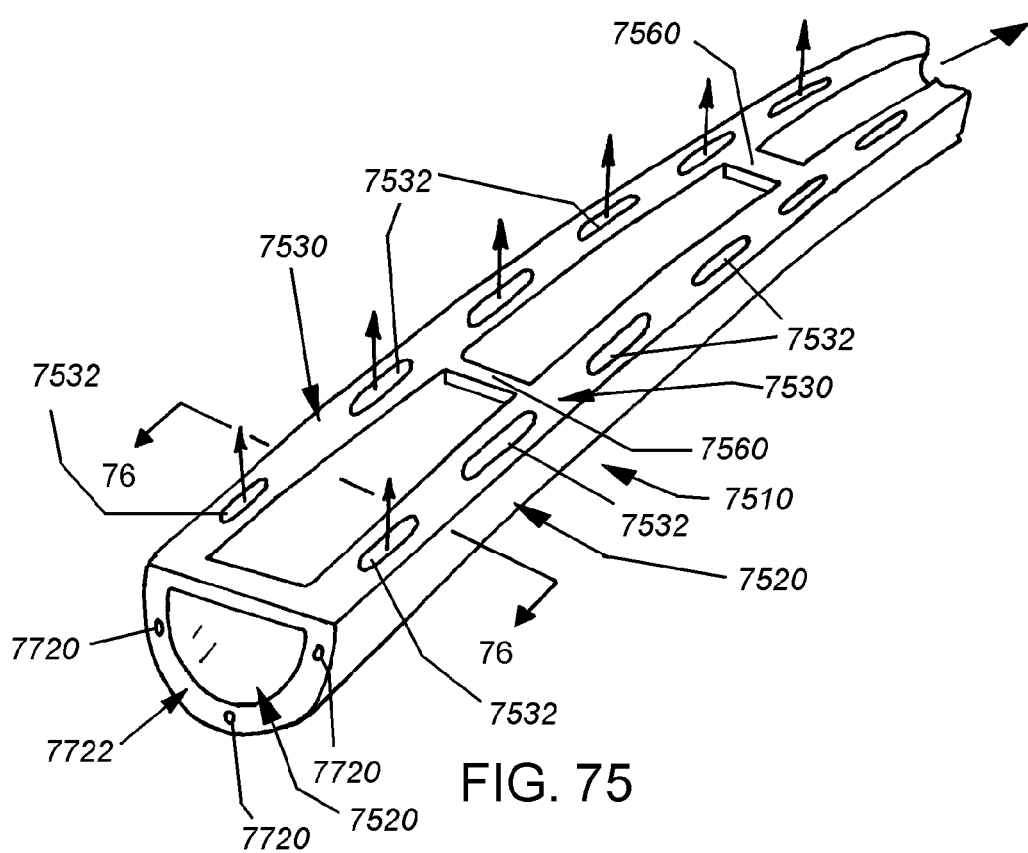
FIG. 75 is a bottom perspective view of an AID according to an alternate embodiment, featuring lateral vacuum ports along its bottom surface.
Figure 76:
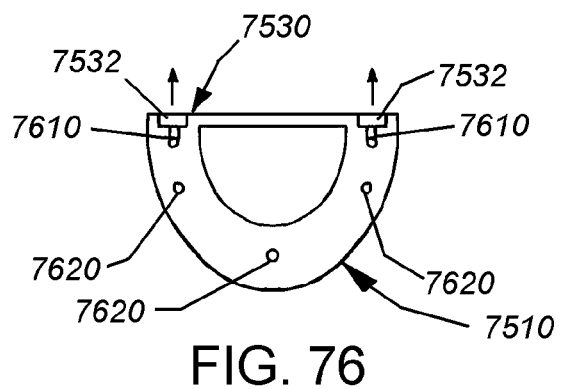
FIG. 76 is a front cross section of the AID taken along line 76-76 of FIG. 75.
Figure 77:
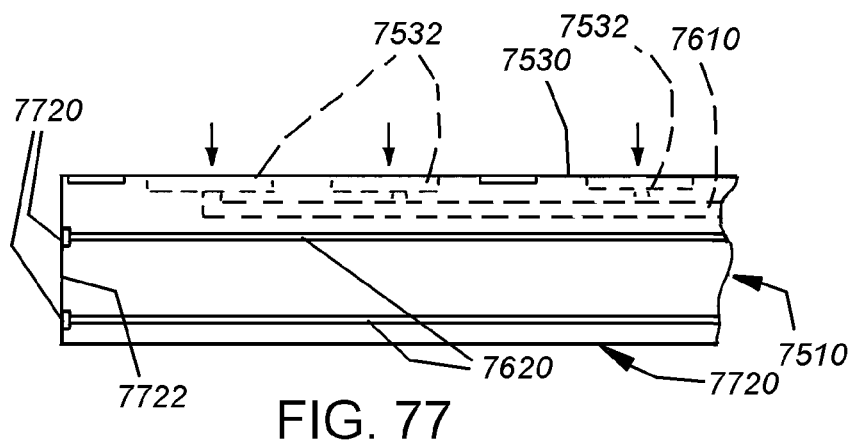
FIG. 77 is a partially exposed side cross section of the AID of FIG. 75.

Another embodiment of an AID 7510 is shown in FIGS. 75-77. In the bottom view of FIG. 75, the AID comprises a semi-circular-cross-section (or D-shaped) housing 7520 with an internal lumen sized and arranged to receive a catheter. The elongated side bases 7530 of the AID bottom each include a series of elongated ports 7532 in communication with a vacuum lumen 7610 as shown further in FIG. 76. A set of steering wire lumens 7620 are provided around the semi-circular portion of the housing 7520. Associated steering wire anchors 7720 (FIG. 77) are provided at the distal end 7722 of the AID housing 7720. The steering wires 7620 extend proximally from these anchors, and eventually terminate at the control system. At various locations along the length of the AID bottom, a strengthening rib 7560 ties the two sides 7530 of the bottom together. This prevents the opposing elongated side bases 7530 of the AID from splaying apart along the AID's midsection. However, this ribbed bottom configuration still allows this sufficient area for the enclosed catheter to be exposed to the underlying tissue.

Figure 78:
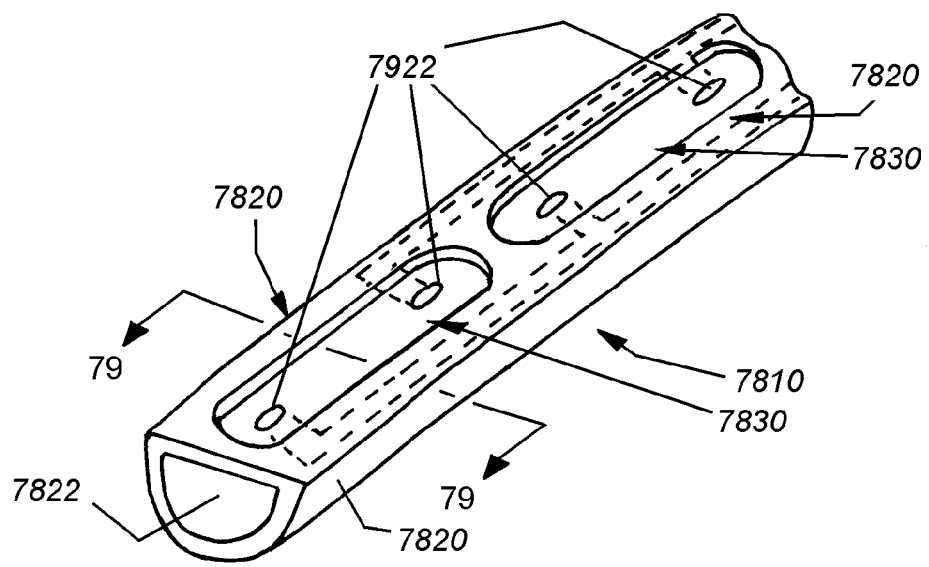
FIG. 78 is a bottom perspective view of an AID according to an alternate embodiment, featuring central vacuum ports along its bottom surface.
Figure 79:
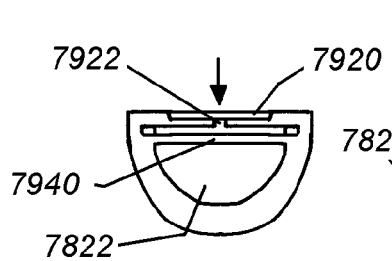
FIG. 79 is a front cross section of the AID taken along line 79-79 of FIG. 78.
Figure 80:
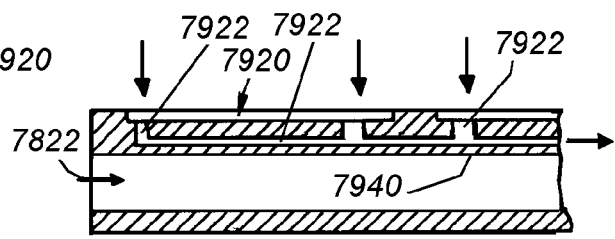
FIG. 80 is a partially exposed side cross section of the AID of FIG. 78.

With reference now to FIGS. 78-80, another embodiment of an AID 7810 is shown. This AID includes a tissue-engaging bottom with side edges 7820 and a semi-circular or D-shaped structure 7820 that defines an open lumen 7822 for receiving a therapeutic (for example, ablation) catheter. A series of openings 7830 are provided along the center of the bottom. These openings 7830 define vacuum ports 7920 that communicate with a set of lumens 7922 extending from the side edges of the structure. The ablation catheter transmits energy through the bottom wall 7940. The wall 7940 is constructed from material having sufficient resistance, or sufficient transmissivity to microwave energy so that the energy passes efficiently into the underlying tissue. This structure has the advantage of maximizing hold-down engagement in the area of the tissue in which the microwave energy actually emits.

IX. Distal Immobilizer-Mounted Minimally Invasive Surgical Tools

While the various AGEs described herein are contemplated for use with ablation procedures, other forms of minimally invasive surgery can be undertaken using, for example, the AGE immobilization, steering and/or actuation mechanisms described herein. It is contemplated that the distal immobilizer (or the proximal immobilizer in certain embodiments) can be adapted to carry a variety of surgical tools for performing procedures other than ablation.

Figure 81:
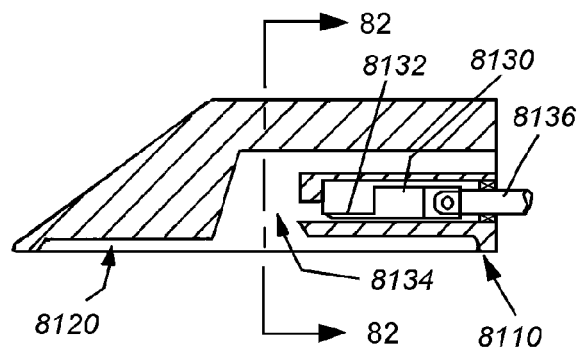
FIG. 81 is a side cross section of a distal immobilizer according to an alternate embodiment, featuring a biopsy cutting tool.
Figure 82:
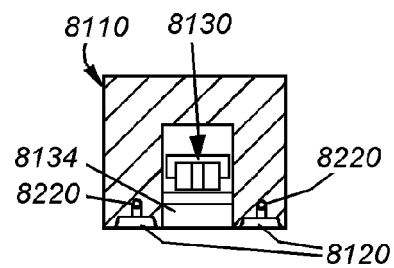
FIG. 82 is a front cross section of the distal immobilizer taken along line 82-82 of FIG. 81.

FIGS. 81 and 82 show an embodiment of the distal immobilizer 8110 of an AGE (or AID in some implementations) that contains a vacuum immobilizer channel 8120 according to any embodiment herein. Another type of immobilizer mechanism, such as a microneedle-based, hold-down system, can be employed in an alternate embodiment.

The exemplary immobilizer 8110 is adapted for performing biopsy procedure on internal tissues. The immobilizer 8110 includes a pneumatic, hydraulic, electromechanical or mechanically operated cutter assembly 8130 within its housing. The cutter assembly 8130 with a cutter blade 8132 that extends into a vacuum extraction port 8134 upon activation of a linkage 8136. The cutter can be operated alternatively, by pressure and/or vacuum, a mechanical linkage or electromechanical energy, such as a solenoid. As shown in the front cross section, the dissection channel is, in fact, located along the center of the body while the two immobilizer channels 8120 are located on opposing side basis so as to remain separated from the dissection channel. Vacuum lumens 8220 are provided for each hold-down. In operation, the immobilizer is placed over an area to be separated from a drawn-in bolus of tissue, and the severed tissue is drawn into the tissue-extraction port 8134. The blade 8132 moves forward when the tissue is in place to cut it off and draw it to the port 8134.

Figure 83:
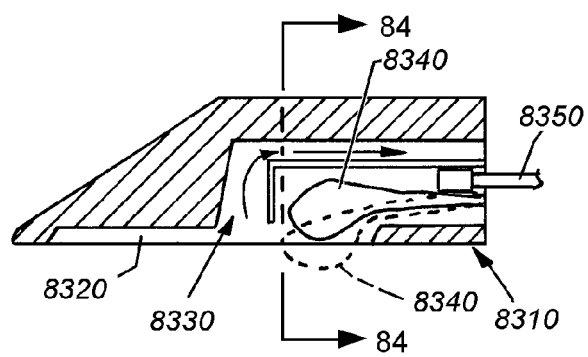
FIG. 83 is a side cross section of a distal immobilizer according to an alternate embodiment, featuring a dissection tool.
Figure 84:
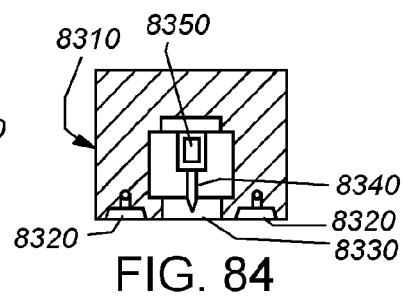
FIG. 84 is a front cross section of the distal immobilizer taken along line 84-84 of FIG. 83.

Another embodiment of a distal immobilizer 8310, which can be used in conjunction with minimally invasive surgery, is shown in FIGS. 83-84. The distal immobilizer 8310 in this embodiment is adapted to perform tissue-dissection procedures. It also includes immobilization vacuum channels 8320 that are disposed along the sides of the base. A central vacuum tissue channel 8330 is located to extract tissue that is acted upon by a cutting knife 8340. The knife moves downwardly (as shown in phantom in FIG. 83) under operation of an actuator 8350. In one embodiment, the actuator is a pneumatic actuator. Alternatively, the actuator can be implemented as a mechanical actuator, joined by a push-pull linkage to the control system, for engagement by the user, or an electromechanical actuator such as a solenoid. The dissection knife 8340 moves downwardly below the plane of the base (as shown in phantom) to slice underlying tissue. Any detritus can then be extracted though the vacuum tissue port 8330. This distal immobilizer 8310 is effective in any dissection operation to be performed minimally invasively.

Figure 85:
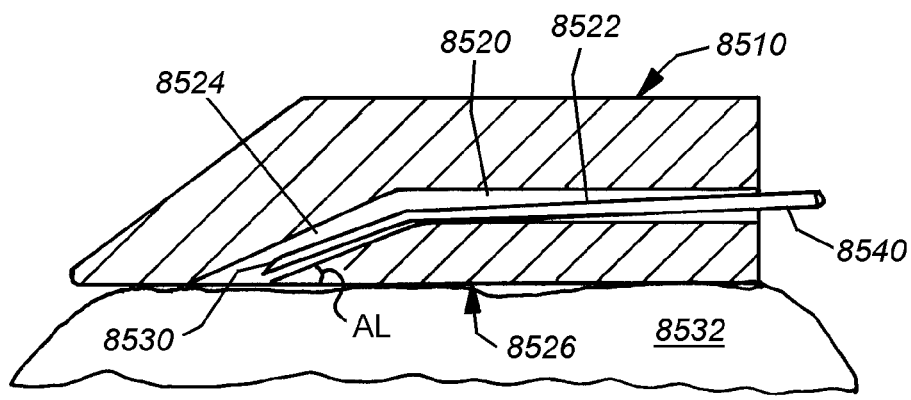
FIG. 85 is a side cross section of a distal immobilizer according to an alternate embodiment, featuring an acute-angled-entry deployable fluid-delivery hypodermic needle in a retracted position.
Figure 86:
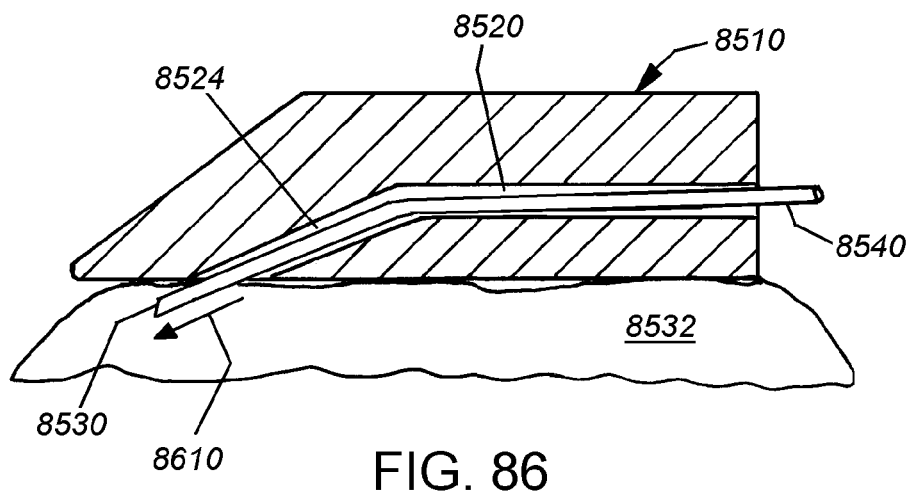
FIG. 86 is a side cross section of the distal immobilizer of FIG. 85, showing the needle in a deployed position, engaging adjacent tissue.

FIGS. 85 and 86 detail another type of minimally invasive instrument constructed within a distal immobilizer 8510. The associated vacuum immobilization, and other mechanisms, have been omitted for simplicity. Any of the above-described immobilization structures can be employed, as well as any appropriate actuation and/or steering mechanism. The instrument of this embodiment can also be used in conjunction with AID, which omits an actuation and/or steering function.

The depicted immobilizer 8510 includes a needle-guide lumen 8520 into which is mounted an elongated, flexible needle 8522 with a central lumen for delivery of fluid. The distal end 8524 of the lumen 8520 is angled at an acute angle AL with respect to the base 8526. The angle AL can be between approximately 10 degrees and 75 degrees in an illustrative embodiment, but the angle can be highly varied in alternate embodiments. The needle 8522 is also angled to a conventional chisel point at its distal end to assist entry into tissue. The needle 8522 can be constructed from any biocompatible material including a resilient polymer or a memory metal such as Nitinol. It includes an appropriate tip 8530 for incursion into tissue 8532. The needle 8522 communicates with a proximal fluid lumen 8540 that can be connected to a conventional fluid-introduction coupling outside the patient. Alternatively an array of microneedles could be used instead of a single needle to deliver fluids as described in the embodiment below.

Once the immobilizer 8510 is held down to the tissue 8532, as shown in FIG. 86, the needle can be driven forwardly (arrow 8610) into the tissue 8532. The bend in the needle-guide lumen 8520 causes the needle 8522, which is constructed from flexible metal, to also bend as shown that it enters the skin at the approximate angle AL. In this manner, the needle 8522 does not pierce at a normal (perpendicular) angle to the tissue, which may cause it to puncture a thin membrane. Rather, the needle 8522 extends sideways into the tissue, with less chance of puncturing completely through an underlying membrane. In the case of the pericardium, this undesirable effect could cause a needle to puncture the heart. Once the tissue is pierced by the needle 8522, an appropriate fluid can be delivered through the fluid lumen 8540 to exit the hollow tip 8530.

Figure 87:
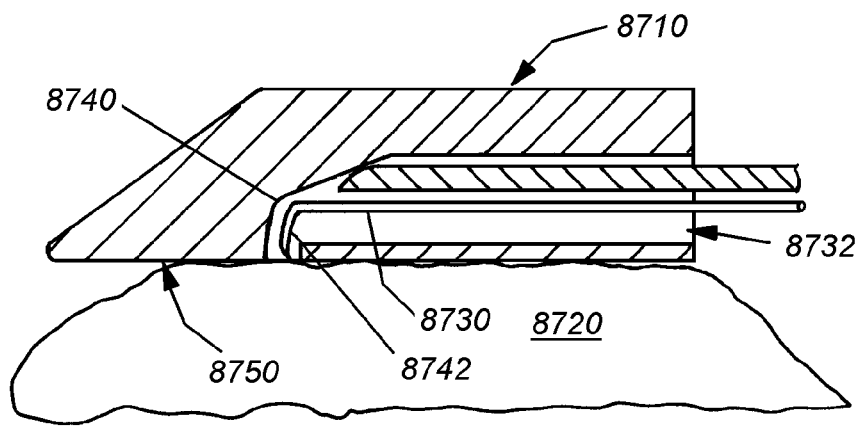
FIG. 87 is a side cross section of a distal immobilizer according to an alternate embodiment, featuring an perpendicularly angled-entry deployable fluid-delivery hypodermic needle in a refracted position.
Figure 88:
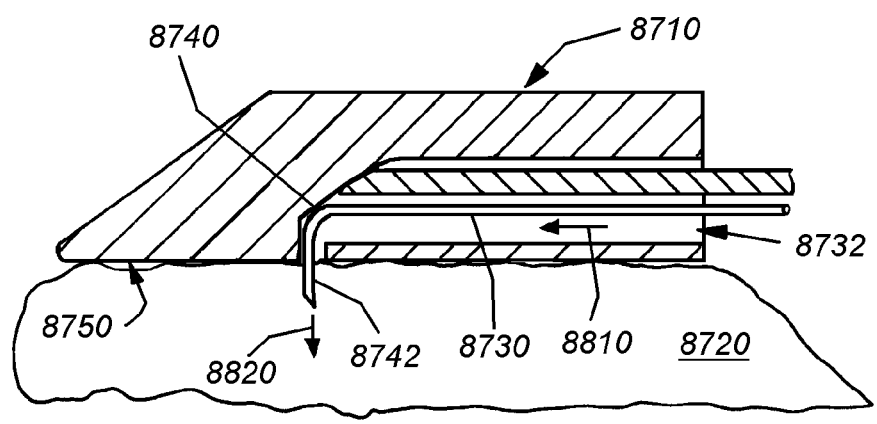
FIG. 88 is a side cross section of the distal immobilizer of FIG. 87, showing the needle in a deployed position, engaging adjacent tissue.

In FIGS. 87 and 88, another distal immobilizer 8710 is shown immobilized on tissue 8720. The needle 8730 resides within a lumen 8732 that includes a rounded distal-most wall 8740. The needle end 8742 is normally directed downwardly (being formed from a memory metal, or similar-property material) so that is substantially normal to the base 8750 and underlying tissue. When the needle is driven distally (arrow 8810 in FIG. 88) the needle drives downwardly (arrow 8820 in FIG. 88), substantially normal/perpendicular into the underlying tissue 8720 as shown. Hence, the axial, distally directed movement of the needle 8522 causes it to engage the curved wall 8740 and drive downwardly into the tissue 8720 as shown in FIG. 88. Fluid can, thus, be delivered deeper into a tissue in this embodiment when such deeper distribution of a medicament is appropriate. A variety of other geometries and structures for allowing hypodermic needles to be deployed into tissue for delivery of medicaments or other diagnostic purposes (at an appropriate entry angle) can be employed in accordance with alternate embodiments.

Figure 88A:
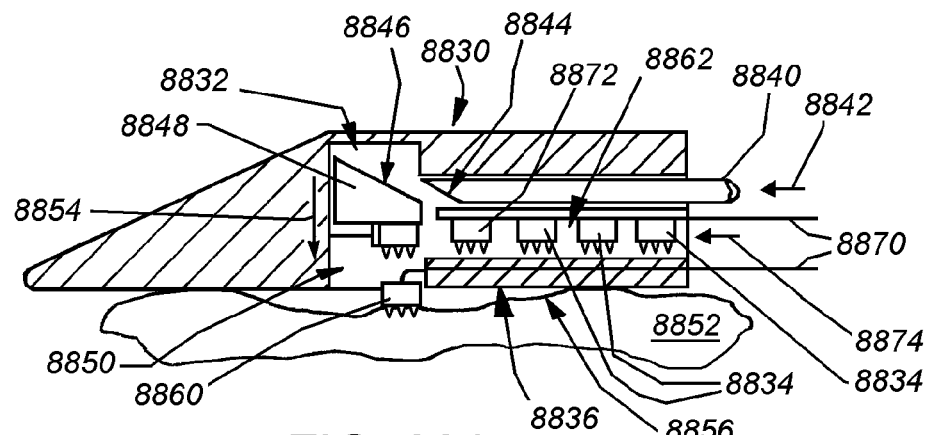
FIG. 88A is a side cross section of a distal immobilizer for an AGE that enables the deployment/implantation of microneedle and microspike implants to tissue for interconnection by wires or tubes to a remote system.
Figure 88B:
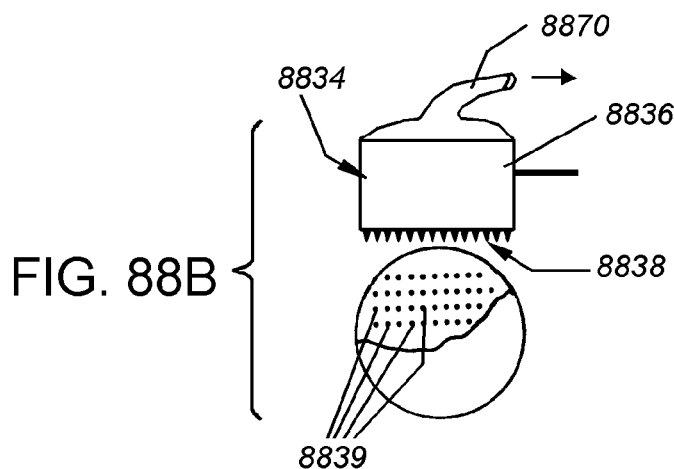
FIG. 88B is a side and partial bottom view of an exemplary microspike or microneedle implant assembly for use with the immobilizer of FIG. 88A.

As described above, rather than a single needle, an array of microneedles can be specially adapted to deliver fluid to tissue according to an alternate embodiment. This arrangement is advantageous in that is combines hold-down and fluid-delivery functions, limits over-penetration into thin-walled tissue and spreads the medicament over a wider area with better dilution so as to limit overmedication of a single point. FIG. 88A shows a distal immobilizer 8830 that is part of an AGE having actuation and steering mechanisms in accordance with any of the above-described embodiments herein. The immobilizer 8830 includes a cavity 8832 that is adapted to store a plurality of microneedle or microspike assemblies 8834. A vacuum or other immobilization mechanism is provided along part of the base 8836 of the immobilizer 8830. In this embodiment, the microneedles are designed for implantation to tissue, rather than use as an immobilization mechanism. However, the teachings herein can be applied to fixed, hold-down immobilizers as described above. In other words, the electronic interconnections and fluid interconnections used in association with these immobilizers can be modified to operate with a fixed, hold-down embodiment of a microneedle array.

Figure 88C:
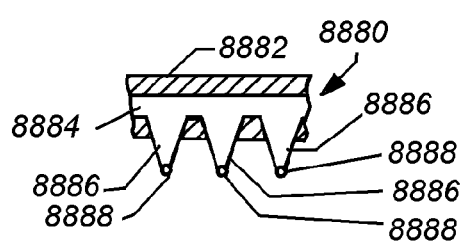
FIG. 88C is a partial cross section of an exemplary fluid-delivery microneedle structure that can be employed in the assembly of FIG. 88B.
Figure 88D:
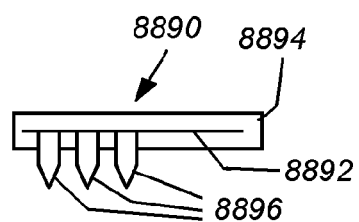
FIG. 88D is a partial cross section of an exemplary electronic sensor microspike structure that can be employed in the assembly of FIG. 88B.

As shown further in FIG. 88D, a typical microneedle assembly 8834 is further detailed. In this embodiment, the assembly 8834 includes a base 8836 that can be constructed from a biocompatible and/or biodegradable material. Biodegradable materials allow for eventual reabsorbtion of the array without need to surgically remove it when no longer needed. On the tissue-engaging bottom 8838 of the assembly 8834 is formed a microneedle or microspike arrangement 8839. In accordance with FIG. 88A, a driveshaft 8840 is driven distally (arrow 8842) so that its ramped face 8844 engages an opposing ramped face 8846 on an anchoring shaft 8848 that rides within a vertical guideway 8850 that opens onto the underlying tissue 8852. When moved distally 8842, the engagement of the faces 8844 and 8846 causes the anchoring shaft to move downwardly (arrow 8854) into the underlying tissue surface. 8856. As shown, a distal-most micro needle or micro spike assembly 8860 has been deposited in the tissue surface 8856. This, and other discrete assemblies 8834, are stored within a chamber 8862 beneath the shaft 8840. Each assembly includes a wire or tube 8870 that communicates through the cannula with the control system. These tubes allow delivery of electrical signals or fluid as appropriate. When the assembly 8834, 8860 is implanted in the tissue 8856, it remains embedded therein with its needles 8839 in engagement with the tissue surface. This interconnection allows the delivery of fluid and/or electrical signal transmission with respect to the tissue surface from a remote location at the control system. Appropriate interfaces at the control system can be employed according to those of ordinary skill for each form of interconnection. When an assembly 8860 is deposited, the next assembly in line (microneedle assembly 8872 in this example) can be moved distally (arrow 8874) to locate it beneath the anchoring shaft 8848 for implantation. An appropriate advancing mechanism (such as a push-rod activated at the control system and extending though the cannula—not shown) can be placed behind the proximal-most assembly to drive the group of assemblies distally.

It is contemplated, that the implanting distal immobilizer (or proximal immobilizer in alternate embodiments) comes prepackaged with the appropriate microneedle assemblies. Briefly, a fluid-delivery assembly 8880 is shown in further detail in FIG. 88C. Beneath the assembly's housing 8882 is provided a hollow fluid reservoir region 8884. This reservoir 8884 communicates with hollow microneedle tubules 8886 having open tips 8888. An appropriate channel within the housing 8882 allows fluid to be transferred from the attached tube (8870) to the reservoir 8884. The structure of the microneedle assembly 8880 can be fabricated in a variety of ways. For example, the microneedles can be constructed on a substrate of metal, silicon or another material using conventional photolithography processes.

A conductive, signal-transmitting microspike assembly 8890 is shown in FIG. 88D. This structure consists of a conductive metal base 8892 that is provided within the housing 8894. The spikes 8896 are individual segments of the metal plate 8892 that have been etched or otherwise cut into the pointed shape as shown, and then folded along their remaining connection with the metal base 8892 into the downwardly directed orientation as shown. The spikes 8896 can be cut on three sides as shown using photochemical-etching or laser-cutting techniques, among other forms of known manufacturing processes. It should be clear that a variety of manufacturing techniques and structures can be used to form either micro needles or micro spikes according to further embodiments.

In accordance with the teachings of this invention an AID or AGE can be provided with an integral ablation mechanism, or any other therapeutic device, rather than a removable catheter positioned in a conforming lumen. The distal end, for example, can include an integral ablative tip that moves across the subject tissue with any power leads that energize the tip extending through the cannula to the control system.

Figure 89:
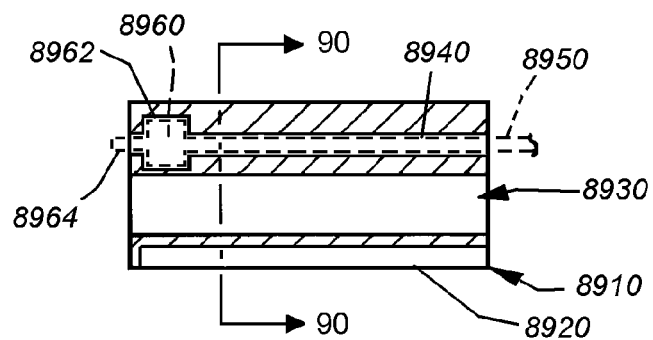
FIG. 89 is a side cross section of a proximal immobilizer for use in rotating/helix drive embodiments showing the location of a flexible joint therefor.
Figure 90:
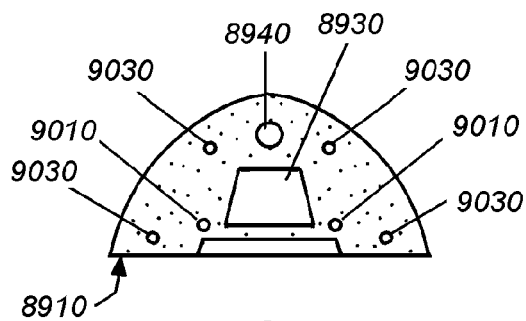
FIG. 90 is a front cross section taken through line 90-90 of FIG. 89.
Figure 91:
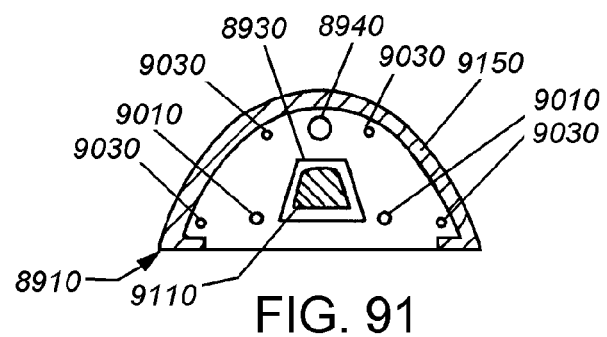
FIG. 91 is a front cross section taken through the interconnecting bellows between the distal immobilizer and the proximal immobilizer of FIG. 89, facing the distal end of the proximal immobilizer.

Reference is now made briefly to FIGS. 89-91, which show a generalized proximal immobilizer for use with a drive helix-actuating arrangement. The proximal immobilizer 8910 includes a central vacuum chamber 8920 that communicates with vacuum lumens 9010 (FIG. 90) a central lumen 8930 receives the catheter 9110 (FIG. 91). Another lumen 8940, above the central lumen 8930 receives the drive shaft 8950 (shown in phantom) and a flexible joint 8960 that resides within an enlarged chamber 8962. The helical drive extends outwardly from the chamber on the shaft 8964 (also shown in phantom). As shown in the cross section 90, four steering lumens 9030 are also provided around the structure. In FIG. 91, the assembled proximal end of the immobilizer 8910 is shown with the bellows cannula flange seal 9150 in place.

FIGS. 92-95 show a distal immobilizer 9210 according to an alternate embodiment. The immobilizer includes a vacuum chamber 9220 having a plurality of vacuum ports 9222 beneath a lumen 9230 for a microwave or other catheter. Each vacuum port 9222 interconnects with a vacuum lumen 9240. A set of steering cables are provided within steering wire lumens 9250. In this embodiment, there are three steering wire lumens 9250. However any appropriate number of lumens and associated wires can be employed in connection with the teachings of this invention.

Figure 92:
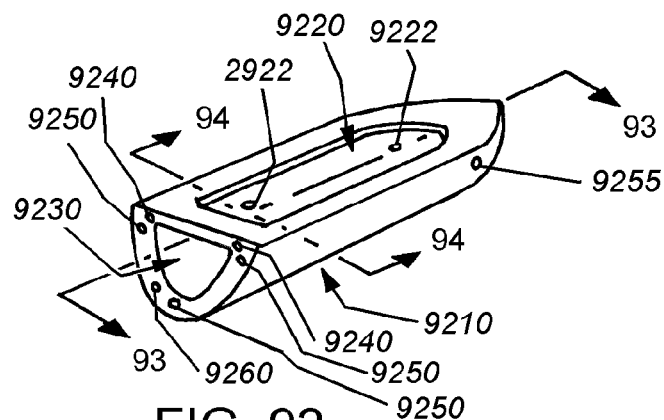
FIG. 92 is a bottom perspective view of an exemplary distal immobilizer according to an alternate embodiment having an inflatable balloon within the inner lumen for locking a catheter in place therein external steering cable tie-down locations and two vacuum ports according to an embodiment of the invention.
Figure 93:
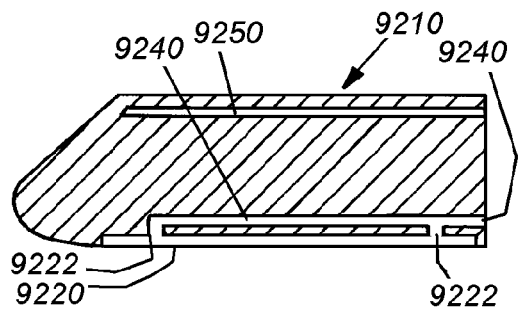
FIG. 93 is a side cross section of the distal immobilizer taken along line 93-93 of FIG. 92.
Figure 94:
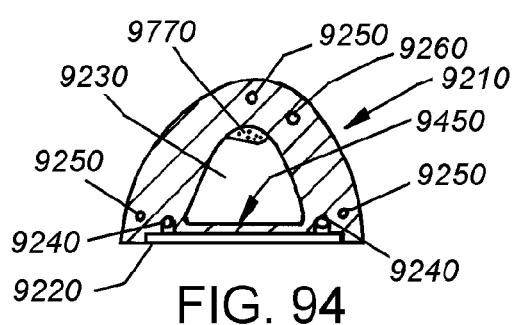
FIG. 94 is a front cross section of the distal immobilizer taken along line 94-94 of FIG. 92.
Figure 95:
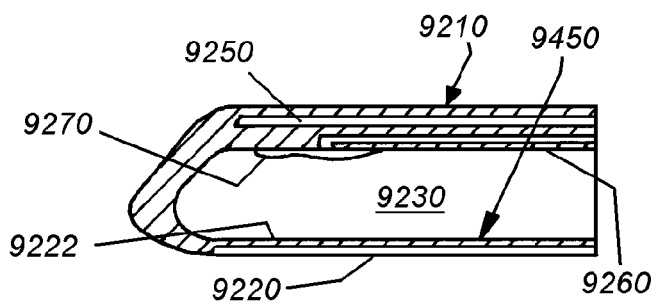
FIG. 95 is a side cross section of the distal immobilizer in accordance with FIG. 92.

An external anchor 9255 for one of the steering wires can be viewed in FIG. 92. In this embodiment, three string cables are used, but fewer or more can be employed in alternate embodiments. Notably, another lumen 9260 is located beside the top steering cable lumen. This lumen 9260 communicates with a pressure source located at the control system. The lumen 9260 attached to a bladder or balloon 9270 located within the top of the catheter lumen 9230. When the catheter is positioned within the lumen, the balloon 9270 can be inflated to secure the catheter in place against the bottom surface 9450 of the catheter lumen 9230. In this manner, the distal immobilizer 9210 provides an effective hold-down mechanism for a catheter or other device inserted into a body cavity.

It should be clear that the foregoing devices provide a wide variety of mechanisms for control, immobilization, manipulation and application of a microwave ablation catheter and other therapeutic devices. It should also be clear that any of the concepts described herein can be combined with other concepts to construct further embodiments that are not expressly shown or described herein. It should also be clear that the AGE, AID and related components described herein can be constructed from a variety of commercially available materials with biocompatible characteristics where appropriate. These materials can be rigid, semi-rigid or flexible/pliable as appropriate to those of ordinary skill in designing such components. The wall thickness for various structures are highly variable and depend, in part upon the size of any lumens passing therethrough, the strength of the chosen material and the overall size/diameter of the device. Such thicknesses can be in the range of one millimeter or less, up to several millimeters. Structures can be formed using a variety of techniques including machining of stock material, molding and rapid-prototyping.

The foregoing has been a detailed description of illustrative embodiments of the invention. Various modifications and additions can be made without departing from the spirit and scope if this invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. For example, the materials employed for the various components herein are highly variable, and can be combined in many ways to provide appropriate characteristics adapted to the particular therapeutic goal. The shape and size of a contained catheter can be highly variable, and the AID or AGE can include a lumen particularly sized and shaped to accommodate the catheter. The external perimeter shape of the AID or AGE can be adapted to the desired delivery system, including a trocar, guiding catheter or guidewire. Also, these devices herein can be fitted with a variety of devices and sensors for measuring characteristics of the contacted tissue and body cavity including, but not limited to heart sensors, temperature sensors and miniature (fiber optic) cameras, which can be placed in conjunction with the catheter or surgical tool to provide appropriate readings of the surrounding area. Also, it is expressly contemplated that any of the devices described herein can be adapted to be employed on any internal organ or tissue structure. Variations in size, shape and other characteristics needed to adapt a device to such a task should be apparent to those of ordinary skill. Likewise the introduction system and location can be adapted to reach such an organ or internal location using techniques known to those of ordinary skill. Accordingly, this description is meant to be taken only by way of example, and not to otherwise limit the scope of this invention.

What is claimed is:

1. A method for ablating a target tissue in a patient's body, the method comprising:
providing a device comprising an ablation catheter comprising an ablation element; and an immobilizer mechanism coupled to the ablation catheter, wherein the immobilizer mechanism is distal to the ablation element, and is configured such that a first portion of the immobilizer mechanism anchors the catheter and a second portion of the immobilizer mechanism axially pulls the ablation element after the first portion of the immobilizer mechanism is anchored to a tissue;
inserting the device into a patient's body
immobilizing the device within the patient's body;
axially pulling, via the immobilizer mechanism, the ablation element to contact to a target tissue while the immobilizer mechanism is engaged; and
ablating a surface of the target tissue.

2. The method according to claim 1, wherein the target tissue is cardiac tissue.

3. The method according to claim 1, wherein the ablation catheter is a radiofrequency ablation catheter.

4. The method according to claim 1, wherein the device is steerable.

5. The method according to claim 1, wherein the immobilizer mechanism comprises an electrical conductivity sensor.

6. The method according to claim 5, wherein the electrical conductivity sensor can verify that a therapeutic ablation has been delivered.

7. The method according to claim 1, further comprising a locking mechanism that is configured to lock the ablation catheter axially in place.

8. The method according to claim 7, wherein when the locking mechanism is engaged, the ablator maintains contact with the target tissue during ablation.

9. The method according to claim 1, wherein the device further comprises a control system operably coupled to the device.

10. The method according to claim 9, wherein the control system controls an amount of energy transmitted to the ablation catheter.

* * * * *